US009554799B2

(12) United States Patent
Belson et al.

(10) Patent No.: US 9,554,799 B2
(45) Date of Patent: Jan. 31, 2017

(54) SURGICAL INCISION AND CLOSURE APPARATUS

(71) Applicant: Zipline Medical, Inc., Campbell, CA (US)

(72) Inventors: Amir Belson, Los Altos, CA (US); Eric Storne, Menlo Park, CA (US); Alan Schaer, San Jose, CA (US); Pankaj Rathi, Mountain View, CA (US); Keiichiro Ichiryu, Campbell, CA (US); Peter D'Aquanni, Murrieta, CA (US); Luke Clauson, Redwood City, CA (US)

(73) Assignee: Zipline Medical, Inc., Campbell, CA (US)

( * ) Notice: Subject to any disclaimer, the term of this patent is extended or adjusted under 35 U.S.C. 154(b) by 0 days.

(21) Appl. No.: 15/081,550

(22) Filed: Mar. 25, 2016

(65) Prior Publication Data
US 2016/0206312 A1 Jul. 21, 2016

Related U.S. Application Data

(63) Continuation of application No. 14/625,366, filed on Feb. 18, 2015, which is a continuation of application (Continued)

(51) Int. Cl.
*A61B 17/08* (2006.01)
*A61B 17/02* (2006.01)
(Continued)

(52) U.S. Cl.
CPC ............. *A61B 17/085* (2013.01); *A61B 17/08* (2013.01); *A61B 17/02* (2013.01); *A61B 17/0466* (2013.01);
(Continued)

(58) Field of Classification Search
CPC ... A61B 17/0466; A61B 17/08; A61B 17/083; A61B 17/085; A61B 2017/081; A61B 2017/086; A61B 2017/088
(Continued)

(56) References Cited

U.S. PATENT DOCUMENTS 2,012,755 A 8/1935 Muth
2,371,978 A 3/1945 Perham
(Continued)

FOREIGN PATENT DOCUMENTS

CN 1126430 A 7/1996
CN 1442119 A 9/2003
(Continued)

OTHER PUBLICATIONS

Merriam-Webster Dictionary, definition of "lateral", http://www.merriam-webster.com/dictionary/lateral as accessed on May 5, 2016.*
(Continued)

*Primary Examiner* — Todd J Scherbel
(74) *Attorney, Agent, or Firm* — Wilson, Sonsini, Goodrich & Rosati

(57) ABSTRACT

An apparatus for closing a surgical incision comprises left and right base panels, a plurality of closure components, and a plurality of left and right axial supports coupled to the respective base panels. The closure components couple the left and right base panels to each other laterally and have left and right ends coupled to the respective base panels. The closure components are positioned laterally across the left and right panels, the left axial supports are disposed between pairs of left closure component ends, the right axial supports are disposed between pairs of right closure component ends, and the left and right axial supports are offset from one another such that a serpentine arrangement of consecutive
(Continued)

closure components and axial supports is formed. The apparatus can be made of antimicrobial materials or materials impregnated with antimicrobial agents. A flexible adhesive cover can be provided over the apparatus when in use.

24 Claims, 36 Drawing Sheets

Related U.S. Application Data

No. 14/180,564, filed on Feb. 14, 2014, now Pat. No. 9,089,328, which is a continuation-in-part of application No. 13/665,160, filed on Oct. 31, 2012, which is a continuation-in-part of application No. 13/286,757, filed on Nov. 1, 2011, now Pat. No. 8,323,313.

(60) Provisional application No. 61/889,569, filed on Oct. 11, 2013, provisional application No. 61/958,259, filed on Jul. 24, 2013, provisional application No. 61/958,254, filed on Jul. 24, 2013.

(51) Int. Cl.
A61B 17/04 (2006.01)
A61B 17/00 (2006.01)

(52) U.S. Cl.
CPC .... A61B 17/083 (2013.01); A61B 2017/00407 (2013.01); A61B 2017/00884 (2013.01); A61B 2017/081 (2013.01); A61B 2017/086 (2013.01); A61B 2017/088 (2013.01)

(58) Field of Classification Search
USPC ........................................ 606/213, 215–218
See application file for complete search history.

(56) References Cited

U.S. PATENT DOCUMENTS

| | | |
|---|---|---|
| 2,747,248 A | 5/1956 | Mercer |
| 3,118,201 A | 1/1964 | Beghetto, Jr. |
| 3,487,836 A | 1/1970 | Benjamin et al. |
| 3,516,409 A | 6/1970 | Robert |
| 3,698,395 A | 10/1972 | Harrith |
| 3,863,640 A | 2/1975 | Haverstock |
| 3,926,193 A | 12/1975 | Hasson |
| 3,933,158 A | 1/1976 | Haverstock |
| 3,971,384 A | 7/1976 | Hasson |
| 3,972,328 A | 8/1976 | Chen |
| 4,038,989 A | 8/1977 | Romero-Sierra et al. |
| 4,114,624 A | 9/1978 | Haverstock |
| 4,222,383 A | 9/1980 | Schossow |
| 4,224,945 A | 9/1980 | Cohen |
| 4,526,173 A | 7/1985 | Sheehan |
| 4,531,521 A | 7/1985 | Haverstock |
| 4,535,772 A | 8/1985 | Sheehan |
| 4,539,990 A | 9/1985 | Stivala |
| 4,576,163 A | 3/1986 | Bliss |
| 4,605,005 A | 8/1986 | Sheehan |
| 4,676,245 A | 6/1987 | Fukuda |
| 4,702,251 A | 10/1987 | Sheehan |
| 4,780,168 A | 10/1988 | Beisang et al. |
| 4,871,367 A | 10/1989 | Christensen et al. |
| 4,881,546 A | 11/1989 | Kaessmann |
| 4,905,694 A | 3/1990 | Will |
| 4,950,282 A | 8/1990 | Beisang et al. |
| 4,966,605 A | 10/1990 | Thieler |
| 4,976,726 A | 12/1990 | Haverstock |
| 5,176,703 A | 1/1993 | Peterson |
| 5,306,236 A | 4/1994 | Blumenfeld et al. |
| 5,336,219 A | 8/1994 | Krantz |
| 5,377,695 A | 1/1995 | An Haack |
| 5,514,155 A | 5/1996 | Daneshvar |
| 5,562,705 A * | 10/1996 | Whiteford ............ A61B 17/085 606/213 |
| 5,665,108 A | 9/1997 | Galindo |
| 5,725,507 A | 3/1998 | Petrick |
| 5,788,660 A | 8/1998 | Resnik |
| 5,843,123 A | 12/1998 | Brazeau |
| 6,007,564 A | 12/1999 | Haverstock |
| 6,074,965 A | 6/2000 | Bodenschatz et al. |
| 6,126,615 A | 10/2000 | Allen et al. |
| 6,176,868 B1 | 1/2001 | Detour |
| 6,194,629 B1 | 2/2001 | Bernhard |
| 6,689,100 B2 | 2/2004 | Connelly et al. |
| 6,726,706 B2 | 4/2004 | Dominguez |
| 7,066,182 B1 | 6/2006 | Dunshee |
| 7,361,185 B2 | 4/2008 | O'Malley et al. |
| 7,455,681 B2 | 11/2008 | Wilke et al. |
| 7,511,185 B2 | 3/2009 | Lebner |
| 7,641,682 B2 | 1/2010 | Palmaz et al. |
| 7,645,285 B2 | 1/2010 | Cosgrove et al. |
| 7,799,042 B2 | 9/2010 | Williamson, IV et al. |
| 8,246,590 B2 | 8/2012 | Hu et al. |
| 8,313,508 B2 | 11/2012 | Belson et al. |
| 8,323,313 B1 | 12/2012 | Belson et al. |
| 8,439,945 B2 | 5/2013 | Belson et al. |
| 8,592,640 B2 | 11/2013 | Zepeda et al. |
| 9,050,086 B2 | 6/2015 | Belson et al. |
| 9,089,328 B2 | 7/2015 | Belson et al. |
| 9,179,914 B2 | 11/2015 | Belson et al. |
| 9,474,529 B2 | 10/2016 | Belson et al. |
| 2002/0099315 A1 | 7/2002 | Lebner |
| 2003/0108352 A1 | 6/2003 | Hellman |
| 2003/0120198 A1 | 6/2003 | Barkell et al. |
| 2003/0163160 A1 | 8/2003 | O'Malley et al. |
| 2003/0220596 A1 | 11/2003 | Dunshee |
| 2004/0072964 A1 | 4/2004 | Udding et al. |
| 2004/0204740 A1 | 10/2004 | Weiser |
| 2004/0210176 A1 | 10/2004 | Diana |
| 2005/0020956 A1 | 1/2005 | Lebner |
| 2005/0020957 A1 | 1/2005 | Lebner |
| 2005/0070956 A1 | 3/2005 | Rousseau |
| 2005/0080453 A1 | 4/2005 | Lebner et al. |
| 2005/0085757 A1 | 4/2005 | Santanello |
| 2005/0153090 A1 | 7/2005 | Marchitto et al. |
| 2005/0234485 A1 | 10/2005 | Seegert et al. |
| 2005/0277959 A1 | 12/2005 | Cosgrove et al. |
| 2005/0284801 A1 | 12/2005 | Tacklind |
| 2006/0200198 A1 | 9/2006 | Riskin et al. |
| 2006/0259033 A1 | 11/2006 | Nesbitt |
| 2007/0026078 A1 | 2/2007 | Almarsson et al. |
| 2007/0038247 A1 | 2/2007 | Lebner et al. |
| 2007/0078366 A1 | 4/2007 | Haggstrom et al. |
| 2007/0088339 A1 | 4/2007 | Luchetti et al. |
| 2007/0141130 A1 | 6/2007 | Villanueva et al. |
| 2007/0179419 A1 | 8/2007 | Simpson |
| 2007/0260278 A1 | 11/2007 | Wheeler et al. |
| 2008/0033334 A1 | 2/2008 | Gurtner et al. |
| 2008/0069855 A1 | 3/2008 | Bonutti |
| 2008/0081951 A1 | 4/2008 | Frasier et al. |
| 2008/0103550 A1 | 5/2008 | Wenzel et al. |
| 2008/0114396 A1 | 5/2008 | Cory et al. |
| 2008/0147115 A1 | 6/2008 | O'Malley et al. |
| 2008/0228219 A1 | 9/2008 | Weiser |
| 2008/0287864 A1 | 11/2008 | Rosenberg |
| 2009/0036922 A1 | 2/2009 | Riskin et al. |
| 2009/0099496 A1 | 4/2009 | Heegaard et al. |
| 2009/0149869 A1 | 6/2009 | Dolhun |
| 2009/0158131 A1 | 6/2009 | Choi et al. |
| 2009/0162531 A1 | 6/2009 | Nesbitt |
| 2009/0177225 A1 | 7/2009 | Nunez et al. |
| 2009/0177227 A1 | 7/2009 | Warren |
| 2009/0264709 A1 | 10/2009 | Blurton et al. |
| 2009/0299255 A1 | 12/2009 | Kazala, Jr. et al. |
| 2009/0299257 A1 | 12/2009 | Long et al. |
| 2009/0299303 A1 | 12/2009 | Seegert |
| 2010/0100022 A1 | 4/2010 | Greener et al. |
| 2010/0121286 A1 | 5/2010 | Locke et al. |
| 2010/0228287 A1 | 9/2010 | Jeekel et al. |
| 2010/0280545 A1 | 11/2010 | Fridman |
| 2011/0077667 A1 | 3/2011 | Singhatat et al. |

(56) References Cited

U.S. PATENT DOCUMENTS

| | | | |
|---|---|---|---|
| 2012/0016410 A1 | 1/2012 | Belson et al. |
| 2012/0029266 A1 | 2/2012 | Holmes et al. |
| 2012/0046691 A1 | 2/2012 | Belson et al. |
| 2012/0116279 A1 | 5/2012 | Munro et al. |
| 2012/0203273 A1 | 8/2012 | Riskin et al. |
| 2012/0221044 A1 | 8/2012 | Archibald et al. |
| 2012/0226214 A1 | 9/2012 | Gurtner et al. |
| 2012/0232587 A1 | 9/2012 | Burke et al. |
| 2013/0066365 A1 | 3/2013 | Belson et al. |
| 2013/0072969 A1 | 3/2013 | Zhang |
| 2013/0108352 A1 | 5/2013 | Ruiz, Sr. et al. |
| 2013/0178897 A1 | 7/2013 | Wu et al. |
| 2013/0281981 A1 | 10/2013 | Shamir |
| 2013/0282049 A1 | 10/2013 | Peterson et al. |
| 2013/0296930 A1 | 11/2013 | Belson et al. |
| 2013/0331757 A1 | 12/2013 | Belson |
| 2014/0074156 A1 | 3/2014 | Belson et al. |
| 2015/0216527 A1 | 8/2015 | Belson et al. |
| 2016/0095597 A1 | 4/2016 | Belson et al. |
| 2016/0106931 A1 | 4/2016 | Belson et al. |
| 2016/0114146 A1 | 4/2016 | Belson et al. |
| 2016/0206311 A1 | 7/2016 | Belson et al. |
| 2016/0206313 A1 | 7/2016 | Belson et al. |
| 2016/0220252 A1 | 8/2016 | Belson et al. |
| 2016/0249924 A1 | 9/2016 | Belson et al. |
| 2016/0310140 A1 | 10/2016 | Belson et al. |

FOREIGN PATENT DOCUMENTS

| | | |
|---|---|---|
| CN | 1524507 A | 9/2004 |
| CN | 1234327 C | 1/2006 |
| CN | 101938944 A | 1/2011 |
| EP | 1600108 A2 | 11/2005 |
| GB | 1401877 A | 8/1975 |
| JP | 2001149485 A | 6/2001 |
| JP | 2013515417 A | 5/2013 |
| JP | 2013538603 A | 10/2013 |
| WO | WO-8401805 A1 | 5/1984 |
| WO | WO-9629013 A1 | 9/1996 |
| WO | WO-03053296 A1 | 7/2003 |
| WO | WO-2006124671 A2 | 11/2006 |
| WO | WO-2007044647 A2 | 4/2007 |
| WO | WO-2008019051 A2 | 2/2008 |
| WO | WO-2008060532 A2 | 5/2008 |
| WO | WO-2009066116 A1 | 5/2009 |
| WO | WO-2011019859 A2 | 2/2011 |
| WO | WO-2011019859 A3 | 4/2011 |
| WO | WO-2011043786 A1 | 4/2011 |
| WO | WO-2011139912 A1 | 11/2011 |
| WO | WO-2011159623 A1 | 12/2011 |
| WO | WO-2013067024 A1 | 5/2013 |
| WO | WO-2014066879 A2 | 5/2014 |

OTHER PUBLICATIONS

Co-pending U.S. Appl. No. 14/958,803, filed Dec. 3, 2015.
Co-pending U.S. Appl. No. 14/958,818, filed Dec. 3, 2015.
Co-pending U.S. Appl. No. 15/081,526, filed Mar. 25, 2016.
Co-pending U.S. Appl. No. 15/081,595, filed Mar. 25, 2016.
European search report and opinion dated Jan. 7, 2014 for EP Application No. 11778067.6.
European search report and opinion dated Jan. 7, 2014 for EP Application No. 11796253.0.
"European search report and opinion dated Apr. 29, 2015 for EP Application No. 10822334.8."
"European search report and written opinion dated Aug. 12, 2015 for EP Application No. 12844746.3."
Hasson, et al. A new sutureless technique for skin closure. Arch Surg. Jan. 1976;111(1):83-4.
"International search report and written opinion dated Jan. 12, 2016 for PCT Application No. US2015/049671."
International search report and written opinion dated Feb. 6, 2014 for PCT/US2013/067563.
International search report and written opinion dated Mar. 19, 2013 for PCT/US2012/062820.
"International search report and written opinion dated Apr. 29, 2015 for PCT/US2015/010188."
International search report and written opinion dated Jul. 29, 2011 for PCT/US2011/034649.
International search report and written opinion dated Jul. 30, 2010 for PCT/US2010/000430.
International search report and written opinion dated Sep. 10, 2014 for PCT/US2014/016587.
"International search report and written opinion dated Sep. 30, 2015 for PCT Application No. US2015/28066."
International search report and written opinion dated Oct. 21, 2011 for PCT Application No. US11/40213.
"K984204, 510(k) Premarket Notification Summary, Silverlon™ Direct Pressure Wound Closure Strip, May 19, 2007."
Notice of allowance dated Jan. 17, 2013 for U.S. Appl. No. 13/096,602.
Notice of allowance dated Feb. 10, 2015 for U.S. Appl. No. 14/180,524.
Notice of allowance dated Sep. 17, 2012 for U.S. Appl. No. 13/286,378.
Notice of allowance dated Sep. 20, 2012 for U.S. Appl. No. 13/286,757.
"Notice of allowance dated Sep. 22, 2015 for U.S. Appl. No. 13/414,176."
Notice of allowance dated Dec. 19, 2014 for U.S. Appl. No. 14/180,564.
Office action dated Feb. 26, 2015 for U.S. Appl. No. 13/414,176.
Office action dated Mar. 4, 2016 for U.S. Appl. No. 13/874,046.
Office action dated Mar. 21, 2012 for U.S. Appl. No. 13/286,378.
Office action dated Mar. 21, 2014 for U.S. Appl. No. 13/414,176.
Office action dated Mar. 22, 2012 for U.S. Appl. No. 13/286,757.
"Office action dated Apr. 7, 2015 for U.S. Appl. No. 13/685,909."
Office action dated May 2, 2012 for U.S. Appl. No. 13/096,602.
"Office action dated Jun. 5, 2015 for U.S. Appl. No. 13/874,046."
Office action dated Jun. 17, 2014 for U.S. Appl. No. 13/414,176.
Office action dated Jul. 23, 2012 for U.S. Appl. No. 13/286,378.
Office action dated Jul. 23, 2012 for U.S. Appl. No. 13/286,757.
Office action dated Aug. 18, 2014 for U.S. Appl. No. 14/180,564.
Office action dated Aug. 28, 2014 for U.S. Appl. No. 14/180,524.
Office action dated Sep. 19, 2014 for U.S. Appl. No. 13/685,909.
"Office action dated Oct. 14, 2015 for U.S. Appl. No. 13/685,909."
"Office action dated Oct. 23, 2015 for U.S. Appl. No. 13/665,160."
Office action dated Nov. 19, 2012 for U.S. Appl. No. 13/096,602.
Office action dated Dec. 29, 2014 for U.S. Appl. No. 13/685,909.
Co-pending U.S. Appl. No. 15/130,149, filed Apr. 15, 2016.
Co-pending U.S. Appl. No. 15/096,083, filed Apr. 11, 2016.
International search report and written opinion dated Aug. 30, 2016 for PCT/US2016/028297.
Co-pending U.S. Appl. No. 15/201,088, filed Jul. 1, 2016.
European search report and opinion dated Jul. 12, 2016 for EP Application No. 13851258.
Office action dated Jul. 20, 2016 for U.S. Appl. No. 15/130,764.
Zip® Surgical Skin Closure. Fast, non-invasive alternative to staples, sutures and glue. Accessed Aug. 17, 2016. http://www.ziplinemedical.com/products/zip-surgical-skin-closure/.
Co-pending U.S. Appl. No. 15/130,764, filed Apr. 15, 2016.
Notice of allowance dated Jun. 21, 2016 for U.S. Appl. No. 15/081,526.
Office action dated May 3, 2016 for U.S. Appl. No. 13/665,160.
Office action dated May 11, 2016 for U.S. Appl. No. 15/081,595.
Office action dated May 26, 2016 for U.S. Appl. No. 15/081,526.
Office action dated May 31, 2016 for U.S. Appl. No. 15/096,083.
Office action dated Jun. 17, 2016 for U.S. Appl. No. 15/130,149.
Co-pending U.S. Appl. No. 15/337,768, filed Oct. 28, 2016.
Notice of allowance dated Sep. 30, 2016 for U.S. Appl. No. 15/130,149.
Notice of allowance dated Oct. 5, 2016 for U.S. Appl. No. 15/096,083.

(56) References Cited

OTHER PUBLICATIONS

Office action dated Nov. 17, 2016 for U.S. Appl. No. 15/081,595.
Office action dated Dec. 1, 2016 for U.S. Appl. No. 13/665,160.

* cited by examiner

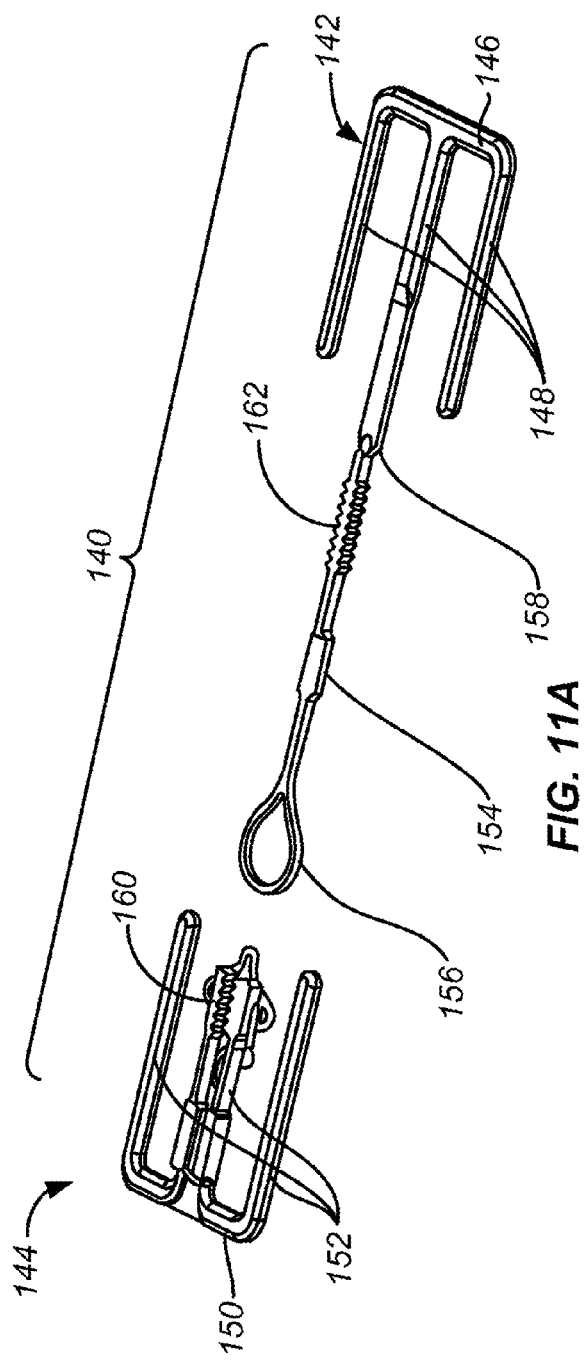
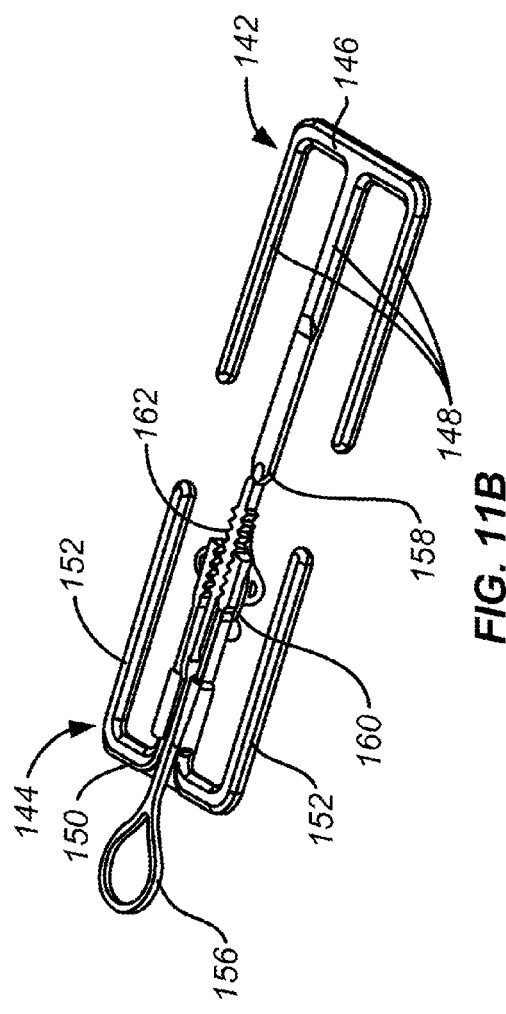
FIG. 11A
FIG. 11B

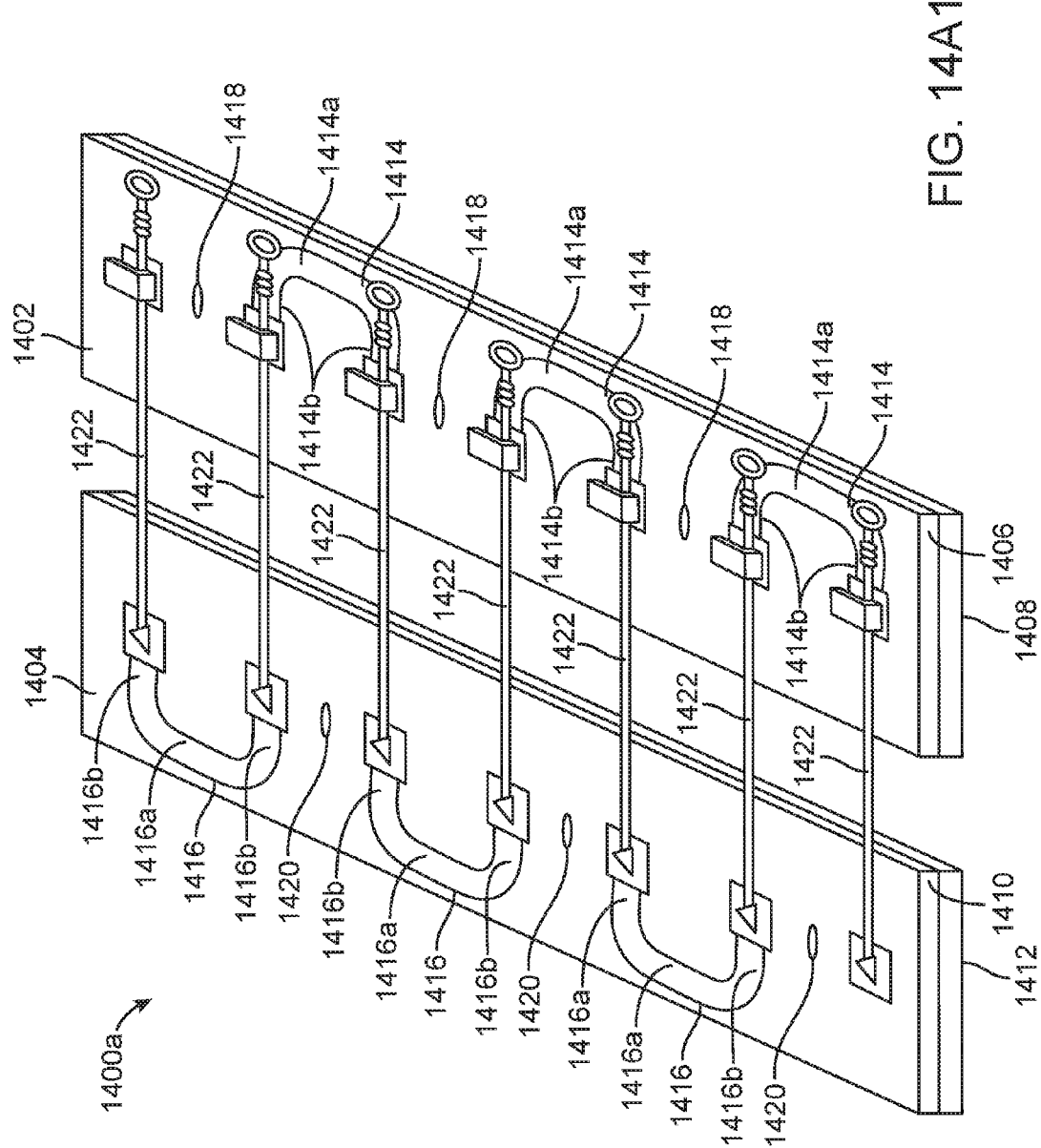
FIG. 14A1

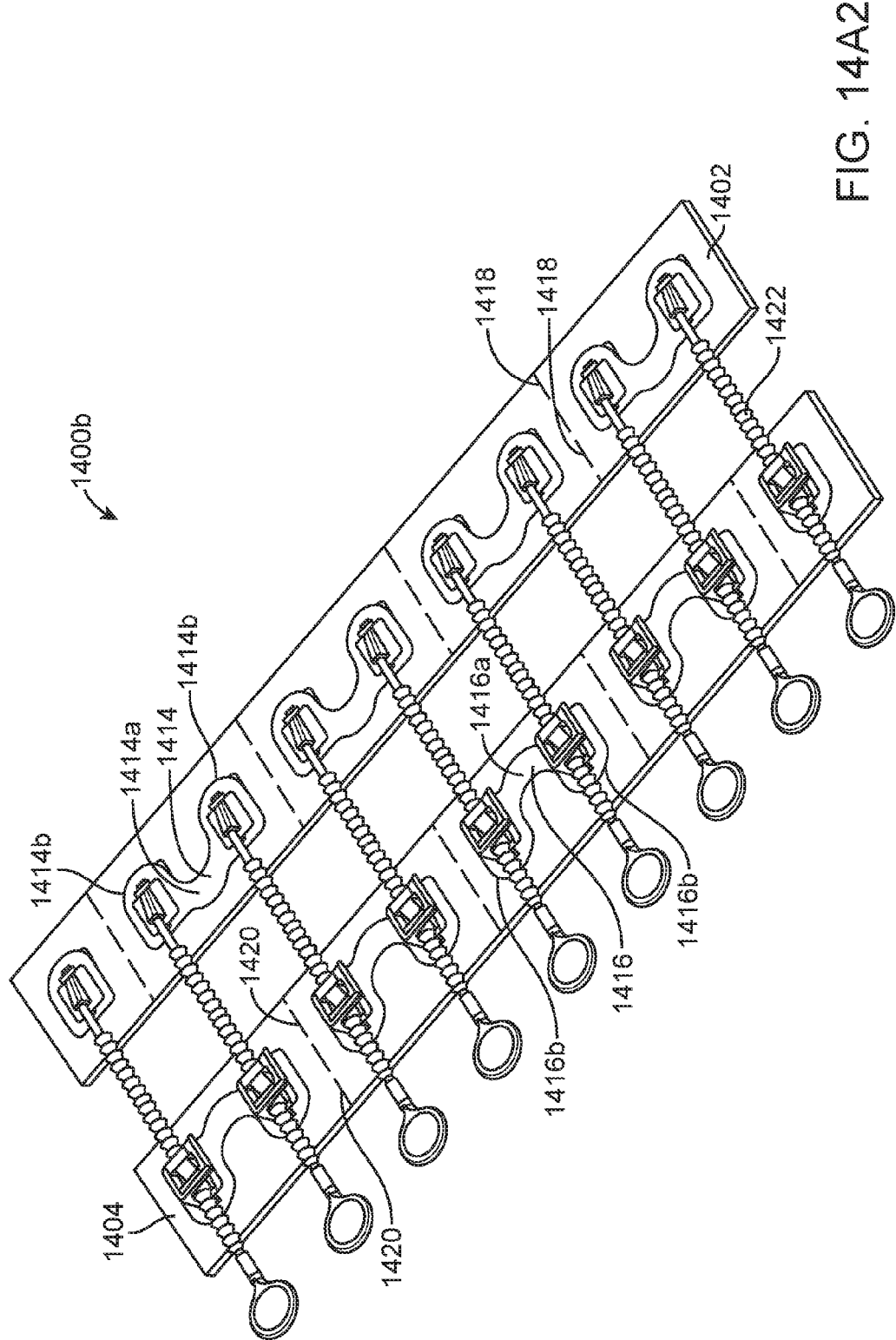
FIG. 14A2

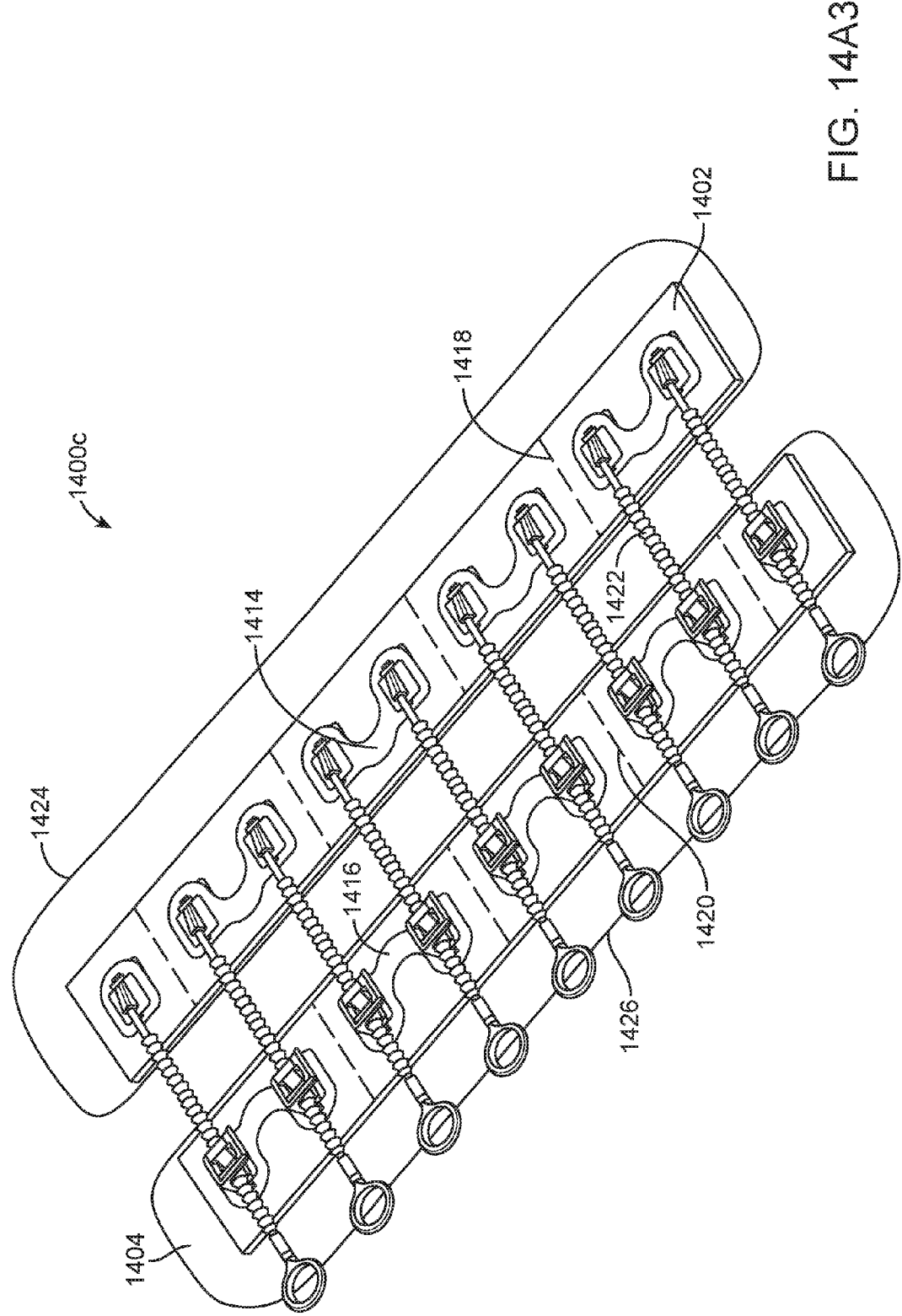

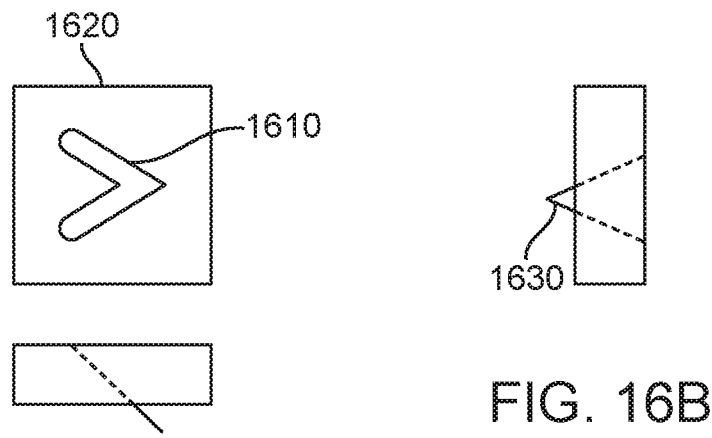
FIG. 16A
FIG. 16B
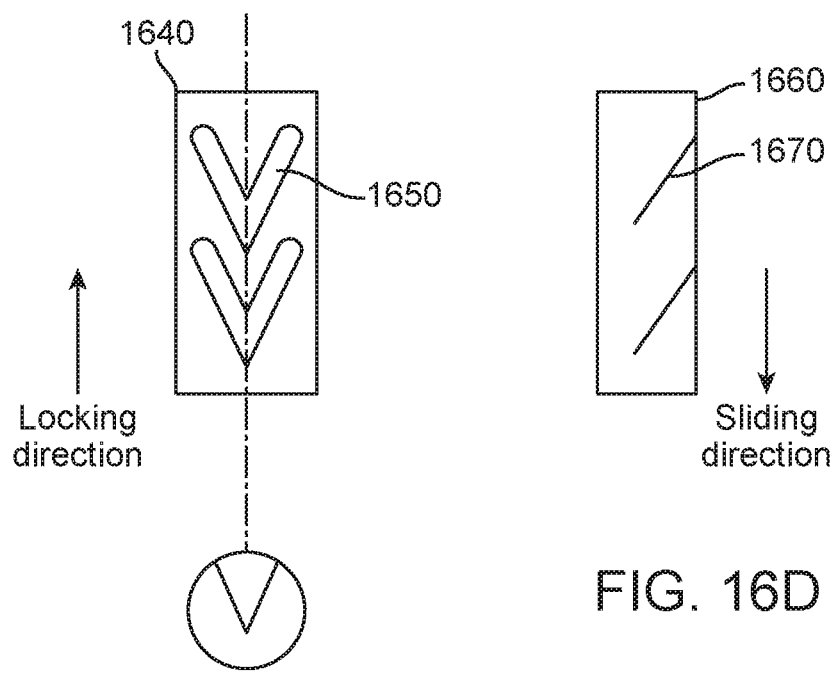
FIG. 16C
FIG. 16D

SURGICAL INCISION AND CLOSURE APPARATUS

CROSS-REFERENCE TO RELATED APPLICATIONS

This application is a continuation of U.S. patent application Ser. No. 14/625,366, filed Feb. 18, 2015, which is a continuation of U.S. patent application Ser. No. 14/180,564, now U.S. Pat. No. 9,089,328, filed Feb. 14, 2014, which is a continuation-in-part of U.S. patent application Ser. No. 13/665,160, filed Oct. 31, 2012, which is a continuation-in-part of U.S. patent application Ser. No. 13/286,757, now U.S. Pat. No. 8,323,313, filed Nov. 1, 2011, and also claims the benefit of U.S. Provisional Applications Nos. 61/889,569, filed Oct. 11, 2013, 61/958,259, filed Jul. 24, 2013, and 61/958,254, filed Jul. 24, 2013, the full disclosures of which are incorporated herein by reference.

The subject matter of this application is related to co-pending U.S. patent application Ser. No. 14/180,524, filed Feb. 14, 2014, the full disclosures of which are incorporated herein by reference.

BACKGROUND OF THE INVENTION

1. Field of the Invention

The present invention relates generally to medical apparatus and methods. More particularly, present invention relates to apparatus and methods for forming and closing surgical incisions.

Surgical closure devices including an adhesive based patch with right and left panels are known. Of particular interest of the present invention, such devices are described in co-pending, commonly owned PCT application US 2010/000430, full disclosure which is incorporated herein by reference. As described in the PCT application, an adhesive patch is placed over a patient's skin at a site where it is desired to form a surgical incision. After the patch is placed, an incision is formed along an axial line extending through the middle of the patch. After it is formed, the incision can be opened to perform a desired procedure, and after the procedure is completed the incision may be closed by drawing the inner edges of the panels together with a clip, zipper, or other closure member.

The principal objective of such surgical closure devices is to improve healing and reduce scarring from the incision. This objective, however, has been inhibited by certain characteristics of the presently available devices. For example, the tissue edges are not always brought together along a line evenly, which can increase the eventual scarring. Many such closure devices do not have the ability to adjust the closure force or distance on the tissue edges, limiting the ability to slightly "pucker" tissue which has been found to reduce scarring. Other shortcomings of the available incision and wound closure devices include difficulty of use and inability to conform to tissue manipulation during subsequent surgical protocols, i.e. those devices which are sufficiently rigid to securely close the tissue are often unable to conform to the tissue movement during the surgical procedure.

A particular problem arises with self-adhesive wound closure patches when they're used beneath an adherent surgical incision drape. Such drapes are used to help maintain the sterility of a tissue surface during a surgical procedure, and the drapes may be placed over a previously positioned tissue closure patch. As the surgical incision drape has an adhesive lower surface which adheres to the tissue, the drape will adhere to an upper surface of an underlying tissue closure patch. Removal of the surgical incision drape will thus often remove or at least displace a previously placed tissue closure patch. If any significant portion of the tissue closure patch is removed or displaced, the patch will no longer be useful for closing a surgical wound.

For these reasons, it would be desirable to provide improved surgical incision closure devices and methods for their use. It would be particularly desirable to provide incision closure devices which are able to adhere to the tissue, allow formation of the incision, conform to the deformation of the tissue during a subsequent surgical procedure, and provide controlled closure of the adjacent tissue edges subsequent to the procedure. In particular, it would be desirable if the incision closure devices were able to provide for the control and the uniform distribution of closure forces on the tissue edges while causing minimum restraint or stretching of the tissue during the surgical procedure. It would be still further desirable to provide improved surgical incision closure devices and methods for their use where the devices will resist removal and dislocation when used beneath a surgical incision drape. At least some of these objectives will be met by the inventions described below.

2. Description of the Background Art

Surgical closure devices are described in U.S. Pat. Nos. 2,012,755; 3,516,409; 3,863,640; 3,933,158; 4,114,624; 3,926,193; 4,535,772; 4,676,245; 4,881,546; 4,905,694; 5,377,695; and 7,455,681; and U.S. Patent Publication Nos. 2005/0020956 and 2008/0114396. Further surgical closure devices are described in commonly owned U.S. Pat. Nos. 8,313,508, 8,323,313, and 8,439,945; U.S. Patent Publication No. 2013/0066365; and PCT Publication nos. WO 2011/139912, WO 2011/159623, WO 2011/043786, and WO 2013/067024, the full disclosures of which are incorporated herein by reference. Commercial incision closure devices available from Ethicon, a division of Johnson & Johnson, under the trade name Ethizip™ temporary abdominal wound closure device.

SUMMARY OF THE INVENTION

The present invention provides improved apparatus and methods for closing wounds, particularly wounds resulting from incisions performed during surgical procedures. The incisions would usually be formed in a patient's skin, such as through the abdomen, but in some cases could also be on internal organs, within the oral cavity, within body cavities, or alike.

The devices and methods of the present invention will present minimum disruption of or interference with the surgical procedure which is performed after the incision is made. In particular, the devices and methods will permit the opposed edges of the incised tissue to be opened, stretched, and freely deformed with minimal restraint resulting from the presence of the closure device. Once the procedure has been completed, however, the devices and methods of the present invention will provide for a uniform distribution of closure forces to draw the tissue edges together in a manner which minimizes scarring. In particular, the closure devices can draw the tissue edges together at a slightly closer spacing than initially present at the forming of the incision in order to upwardly evert the tissue edges and cause a "pucker" which can reduce scarring.

The devices and methods of the present invention will also be able to avoid or reduce disruption when an incision closure appliance is used beneath surgical incision drape which must be removed from over the closure appliance. A sacrificial layer is provided over at least part of the upper surface of the closure appliance, where the sacrificial cover is held in place while the surgical incision drape is placed over the incision closure appliance. After the incision and surgical procedure have been completed, the surgical incision drape will be pulled from the patient's skin. Instead of adhering to and dislodging the tissue closure appliance, the surgical drape adheres to the sacrificial cover, and only the sacrificial cover is pulled from the patient with the drape, leaving the remainder of the incision closure appliance in place.

In a first aspect of the present invention, an incision closure appliance comprises a base including a left panel and a right panel. Each panel has a tissue adherent lower surface, an upper surface, an inner edge, and an outer edge. The lower tissue adherent surface will typically be coated at least partially with a common tissue-adherent adhesive such as those used in surgical bandages and patches.

The incision closure appliance further includes a force distribution structure coupled to each panel (i.e. each panel will have at least one force distribution structure coupled thereto), where each force distribution structure is adapted to allow axial expansion of the panel along the inner edge while limiting lateral expansion over the entire length and axial expansion along the outer edge. By permitting axial expansion of the panel along the inner edge, the tissue edges are minimally constrained to allow the tissue to deform when stretched during the surgical procedure. Conversely, by limiting both lateral expansion and axial expansion along the outer edge, the panel will be able to apply a controlled and distributed closure force when the panels are drawn together after the surgical procedure is complete, as described in more detail below.

The incision closure appliance still further includes a closure component or assembly which attaches to the force distribution structure to draw the inner edges of the panels together after they had been adhered to the tissue on opposite sides of an incision site and the surgical procedure completed. Each panel of the base will typically comprise an at least partially elastic matrix, typically having an isotropic elasticity (i.e. the panel stretches evenly in all directions) but optionally having an anisotropic elasticity (where the matrix stretches preferentially in one direction or over a portion thereof). The elastic matrix may comprise an elastomeric membrane or sheet (for example Polyurethane sheet or Thermo Plastic Elastomers (TPE)), a woven fabric (typically woven at least partially from elastomeric filaments, threads, or fibers), a spun fabric, or the like. In certain embodiments, the elastomeric matrix may comprise a fabric woven from both elastic elements (typically threads, filaments, fibers, or the like) and having inelastic elements disposed along the outer edge and extending laterally there across in order to provide the expansion characteristics described above with respect to the force distribution structure. That is, in some cases, the force distribution structure may include or consist of inelastic elements woven or otherwise incorporated within a fabric membrane.

Typically, the force distribution structure will comprise a separate component of the incision closure appliance, for example including a spine disposed axially adjacent to the outer edge of the panel and a plurality of axially spaced-apart lateral supports disposed laterally and extending from the spine toward the inner edge of the panel. Such a "comb-like" structure will typically be formed from flexible but non-distensible materials so that the elements can flex together with the tissue deformation but will not stretch along their lengths so that they may provide dimensional stability in the lateral direction as well as along the outer edge of the panel. Examples of such materials include Nylon, Polypropylene, Polyethylene and Polycarbonate or other thermoplastic polymers. Notably, the force distribution structure will not limit the axial stretching of the inner edge of the panel in order to provide the desired expansibility and conformability to the tissue during the surgical procedure. Such separate force distribution structures may be attached to the upper surface of the panel, or alternatively may be embedded in or laminated within the panel. Typically, the force distribution structure will not extend into or past the lower surface of the panel so that it will not interfere with adherence of the panel to the skin or other tissue.

The assembly of the base panels and the force distribution structures will typically be carried on a removable backing which covers and protects the adherent surface of the panels prior to use. The backing may be removed in order to apply the base to the skin or other tissue at the site of the surgical intervention. Additionally, the right and left panels will typically be held together by removable tabs, an axial strip, or other removable covers or structures in order to hold the inner edges of the panel at a pre-determined distance or spacing as they are being adhered to the tissue. For example, removable tabs may be placed at each axial end of the base to temporarily secure the two base panels together. Alternatively, a removable strip or tape may be placed over an axial gap between the right and left panels to hold the panels in place relative to each other as the base is being adhered to the tissue surface. Such tabs or strips will typically be self-adhesive so that they may be secured to the panels and then removed by simply pulling off after the panels are properly placed on the tissue. The cover, tabs, or strip may then be removed to leave the panels in place but unconnected prior to forming the surgical incision therebetween.

A first exemplary construction of the closure component or assembly comprises a right engagement member, a left engagement member, and a plurality of lateral struts holding the engagement members laterally apart by a pre-determined distance. The right engagement member is adapted to releasably engage the supports of the right panel along an inner edge thereof, and the left engagement member is adapted to releasably engage the supports of the left panel along an inner edge thereof. In the specific embodiments, at least some of the supports of the force distribution component will have cleats near their inner edges, and the engagement members will have slots which receive the cleats. After the surgical intervention is complete, the closure component may then be placed over the force distribution structure with the cleats on one side first being engaged by an engagement member and then the opposite engagement member being pulled over the cleats on the opposite side.

Alternatively, the closure component or assembly may comprise a plurality of independent lateral ties attached to at least some of the lateral supports. Such lateral ties are configured to be secured between the lateral supports, typically being fixed to one panel and being adjustably attachable to the other panel. For the exemplary embodiments, the adjustably attachable end may comprise a ratchet tightening mechanism or similar structure which allows each lateral tie to be independently adjusted at a different spacing between the right and left panels. In this way, the right and left panels may be differentially tensioned along their inner edges in order to control and optimize the forces applied to the adjacent tissue edges which are being drawn together.

Optionally, the closure appliance of the present invention may further comprise a securing layer which is adapted to be placed over the assembly of the base and the closure component after the assembly has been secured over an incision on a patient's skin and the surgical procedure has been completed. A securing layer will typically have a self-adhesive lower surface which can be placed over the assembly of the base and closure component to help secure it in place and to maintain cleanliness. The securing layer may optionally have openings to permit access to the wound for observation, delivery of antiseptics, and the like.

In a further aspect of the present invention, methods for forming an incision in tissue comprise providing an incision closure appliance as described above. The right and left panels of the appliance are adhered to the patient's skin, where the inner edges of the panels are spaced-apart by a pre-selected distance typically from 0.5 mm to 15 mm. An incision (typically linear) is formed in the tissue or skin surface between the inner edges of the panels, and the edges of the incised tissue are then separated to perform a desired surgical procedure. The inner edges of the panels can stretch and conform along with movement and deformation of the tissue edges while the outer edge and lateral extent of each panel remain dimensionally stable. After the procedure is complete, the closure component is secured to the force distribution structure to draw the inner edges of the panels back together. Optionally, the closure component has dimensions (or an adjustable inter-panel spacing) which draw the tissue edges closer together than they were immediately after the incision was formed. Such drawing together of the tissue causes the edges to evert and the tissue to "pucker" which can reduce scarring.

In yet a further aspect of the present invention, an incision closure appliance is provided. The incision closure appliance may comprise left and right base panels, a plurality of closure components for coupling the left and right base panels to each other laterally, and a plurality of left and right axial supports coupled, respectively, to the left and right base panels. Each closure component comprises left and right closure component ends coupled, respectively, to the left and right base panels. The plurality of closure components may be positioned laterally across the left and right panels with (i) one or more of the left axial supports disposed between at least some axially adjacent left closure component ends and (ii) one or more of the right axial supports disposed between at least some axially adjacent right closure component ends to form a serpentine arrangement.

To form the serpentine arrangement, a left axial support couples every other axially adjacent pair of left closure component ends together on the left panel and/or a right axial support couples every other axially adjacent pair of right closure component ends together on the right panel. The left and/or right panels may have one or more perforations disposed between axially adjacent the respective left and/or right closure component ends having no axial support disposed therebetween. The one or more perforations may comprise a plurality of perforations that facilitate the separation of the base panel into base panel segments upon axial stretching of the base panel.

One or more of the left or right base panels may comprise a plurality of separate base panel segments. At least two left closure component ends or at least two right closure component ends may be coupled to each base panel segment. The left base panel may comprise a plurality of left base panel segments, and the right base panel may comprise a plurality of right base panel segments. The left base panel segments and the right base panel segments may be axially offset from one another when applied to an incision and surrounding tissue. The plurality of closure components may couple the left and right base panel segments to each other laterally to form the serpentine arrangement.

One or more of the left or right base panels may comprise a tissue adherent lower surface for adhering to the tissue adjacent the incision. One or more of the left or right base panels may comprise a lower adhesive layer comprising the tissue adherent lower surface and an upper layer comprising an upper surface. The upper layer may be more rigid than the lower adhesive layer. The lower adhesive layer may be sufficiently elastic such that blistering and adhesion loss due to movement of tissue laterally adjacent the incision closure device when covering the incision and surrounding tissue are minimized. The adhesive lower layer may comprise a hydrophilic adhesive material. The hydrophilic adhesive material may comprise one or more of a hydrocolloid, a hydrogel, an acrylic polymer, or poly (ethylene glycol). The upper layer may comprise one or more of rubber, latex, urethane, polyurethane, silicone, a thermo plastic elastomer (TPE), a woven fabric, or a spun fabric. One or more of the left closure component ends, right closure component ends, left axial supports, or right axial supports may be embedded in or laminated to the upper surfaces of the left and right base panels.

One or more of the left closure component ends, right closure component ends, left axial supports, or right axial supports may be formed from flexible, non-distensible materials.

The plurality of closure component, left axial supports, and right axial supports may together be sufficiently rigid such that movement of tissue laterally adjacent the incision closure device when covering an incision and surrounding tissue does not substantially distend the covered incision and surrounding tissue. Accordingly, movement of a first tissue region laterally adjacent a periphery of the incision closure device may substantially translate into a same movement of a second tissue region laterally adjacent the periphery and opposite the first tissue region.

One or more closure component of the plurality of closure components may comprise a tie securely coupled to the left or right closure component end and adjustably attached to the opposite closure component end. The opposite closure component end may comprise a ratchet tightening mechanism.

The plurality of closure components may be configured to draw inner edges of the left and right base panels together to compress an incision covered by the incision closure appliance.

One or more of the plurality of left axial supports or the plurality of right axial support may be C-shaped. The C-shaped left and/or right axial supports may each comprise an axial portion for limiting axial expansion of the respective base panel and a lateral portion for limiting lateral expansion of the respective base panel.

This aspect of the present invention may also provide a system for closing an incision in tissue. The system may comprise the incision closure device and a flexible cover for overlying the incision closure device and the covered incision and surrounding tissue.

The flexible cover may be configured to extend over lateral and axial edges of the left and right base panels. The cover may have one or more perforations to allow the cover to at least partially stretch axially in response to axial stretching of the incision and surrounding tissue covered by the incision closure device. The one or more perforations may be disposed along a central axial line of the cover. The cover may comprise one or more reinforcing members coupled to at least a portion of an adhesive layer of the cover. The reinforcing members may comprise one or more of rubber, latex, urethane, polyurethane, silicone, a thermo plastic elastomer (TPE), a woven fabric, or a spun fabric. The cover may comprise a hydrophilic adhesive layer which may comprise one or more of a hydrocolloid, a hydrogel, an acrylic polymer, or poly (ethylene glycol).

In yet a further aspect of the present invention, an incision closure appliance is provided. The incision closure appliance comprises a flexible adhesive bottom layer, a middle layer, and a top layer. The flexible adhesive bottom layer may have a first elasticity. The middle layer may be coupled to and cover at least a portion of the flexible adhesive layer and have a second elasticity less than the first elasticity. The top layer may be coupled to and cover at least a portion of the middle layer and have a third elasticity less than the second elasticity. An elasticity gradient between the flexible adhesive bottom layer and the top layer may provide sufficient stiffness for the incision closure appliance such that movement of tissue laterally adjacent the appliance when covering an incision and surrounding tissue does not substantially distend the covered incision and surrounding tissue.

The elasticity gradient may provide sufficient elasticity for the incision closure appliance such that blistering and adhesion loss due to movement of tissue adjacent the appliance when covering the incision and surrounding tissue are minimized.

The incision closure appliance may be axially flexible in response to axial stretching of the incision and surrounding tissue covered by the incision closure appliance. Movement of a first tissue region adjacent the periphery of the flexible adhesive bottom layer may substantially translates into a same movement of a second tissue region adjacent the periphery of the flexible adhesive bottom layer and opposite the first tissue region.

The flexible adhesive bottom layer may comprise a hydrophilic adhesive material. The hydrophilic adhesive material may comprise one or more of a hydrocolloid, a hydrogel, an acrylic polymer, or poly (ethylene glycol).

The upper layer may comprise one or more of rubber, latex, urethane, polyurethane, silicone, a thermo plastic elastomer (TPE), a woven fabric, or a spun fabric.

The flexible adhesive bottom layer may comprise first and second adhesive bottom layers. The middle layer may comprise a first upper layer coupled to the first adhesive bottom layer and a second upper layer coupled to the second adhesive bottom layer. The top layer may comprise an arrangement of a plurality of axial support structures and a plurality of lateral closure components coupled to the axial support structures for fastening the first adhesive bottom layer and the first upper layer to the second adhesive bottom layer and the second upper layer. The plurality of axial support structures and the plurality of closure components may be coupled to one another to form a serpentine pattern for allowing the one or more of the lower adhesive layer or the middle layer to at least partially stretch in the axial direction of the closure device in response to axial stretching of the incision and surrounding tissue covered by the incision closure device. The plurality of axial support structures and the plurality of lateral closure components may be coupled to one another to form a ladder pattern. One or more of the plurality of axial support structures or the plurality of lateral closure components may be formed from flexible, non-distensible materials. The plurality of lateral closure components may be configured to draw inner edges of one or more of the first or second adhesive bottom layers and the first or second upper layers together after flexible adhesive bottom layer is adhered to tissue on opposite sides of the incision. One or more of the lateral closure components may comprise a left end, a right end, and a tie securely coupled to the left or right end and adjustably attached to the opposite end. One or more of the plurality of axial support structures or the plurality of lateral closure components may be embedded in or laminated to the first and second upper layers.

This aspect of the present invention may also provide a system for closing an incision in tissue. The system comprises the incision closure appliance and a flexible cover for overlying the incision closure appliance and the covered incision and surrounding tissue.

The flexible cover may be configured to extend over lateral and axial edges of the flexible adhesive bottom layer. The cover may have one or more perforations to allow the cover to at least partially stretch in the axial direction of the cover in response to axial stretching of the incision and surrounding tissue covered by the incision closure appliance. The one or more perforations may be disposed along a central axial line of the cover. The cover may comprise one or more reinforcing members coupled to at least a portion of an adhesive layer of the cover. The reinforcing members may comprise one or more of rubber, latex, urethane, polyurethane, silicone, a thermo plastic elastomer (TPE), a woven fabric, or a spun fabric. The cover may comprise a hydrophilic adhesive layer. The hydrophilic adhesive layer may comprise one or more of a hydrocolloid, a hydrogel, an acrylic polymer, or poly (ethylene glycol).

In yet a further aspect of the present invention, an incision closure appliance is provided. The incision closure appliance may comprise a lower portion having a first elasticity, an upper portion having a second elasticity less than the first elasticity, and an elasticity gradient between the lower portion and the upper portion. The elasticity gradient may provide sufficient stiffness for the incision closure appliance such that movement of tissue laterally adjacent the appliance when covering an incision and surrounding tissue does not substantially distend the covered incision and surrounding tissue. The elasticity gradient may provide sufficient elasticity for the incision closure appliance such that blistering and adhesion loss to due to movement of tissue laterally adjacent the appliance when covering an incision and surrounding tissue is minimized.

In yet a further aspect of the present invention, an incision closure appliance is provided. The incision closure appliance may comprise a base including a left panel and a right panel, left and right force distribution structures, and a plurality of closure components. Each panel may have a tissue adherent lower surface, an upper surface, a first lateral edge, a second lateral edge. The left and right force distribution structures may be coupled to the left and right panels, respectively. Each force distribution structure may be adapted to allow axial expansion of the panel along one of the first or second lateral edges and to limit lateral expansion across the panel and axial expansion along the opposite lateral edge. The plurality of closure components may be secured to the left and right panels to draw the panels together after the panels are adhered to tissue and an incision made therebetween.

The first lateral edges of each panel may comprise inner edges of each panel. The inner edges of each panel may face toward one another.

The second lateral edges of each panel may comprise outer edges of each panel. The outer edges of each panel may face away from one another.

One or more of the left and right panels of the base may comprise an elastic matrix. The elastic matrix may comprise an elastomeric membrane, a woven fabric, or a spun fabric. The elastic matrix may comprise a fabric woven from elastic elements and having inelastic elements along the first or second lateral edge and extending laterally thereacross.

Each force distribution structure may comprise a spine disposed axially adjacent to the first lateral edge of the panel and a plurality of axially spaced-apart lateral supports disposed laterally and extending from the spine toward the first lateral edge of the panel. The spine and lateral supports may be formed from flexible, non-distensible materials. The force distribution structures may be embedded in or laminated to the upper surface of each panel.

The closure component may comprise a right engagement member, a left engagement member and a plurality of lateral struts holding the engagement members laterally spaced apart by a predefined distance. The right engagement member may be adapted to releasably engage the supports of the right panel and the left engagement member may be adapted to releasably engage the supports of the left panel. At least some of the supports may have cleats near the one or more of the first or second lateral edges and the engagement members may have slots which receive the cleats. The lateral struts may be adjustably connected to at least one of the engagement members to permit adjustment of the predefined distance. The closure component may comprise a plurality of independent lateral ties attached to at least some of the lateral supports. The lateral ties may be configured to be secured between lateral supports. The independent lateral ties may each have one end fixed to a panel and a second end adjustably attached to the other panel. The second end may comprise a ratchet tightening mechanism.

The incision closure appliance may further comprise a securing layer adapted to be placed over an assembly of the base and the closure components after the assembly has been secured over an incision on a patient's skin. The securing layer may have an inner self-adhesive surface.

BRIEF DESCRIPTION OF THE DRAWINGS

FIGS. 11A and 11B illustrate an alternative lateral tie construction which can be used in the appliances of either FIG. 1 or FIG. 9.

FIGS. 14A1-14A3 are perspective views of further embodiments of an incision closure appliance constructed in accordance with the principles of the present invention.

FIGS. 16A-16D show various locking mechanisms in accordance with the principles of the present invention.

DETAILED DESCRIPTION OF THE INVENTION

The apparatus and methods of the present invention will be used during both the formation and the closure of surgical incisions made to a patient's skin or other tissue during surgical procedures. As described hereinafter, the direction of the incision will define both "axial" and "lateral" directions as those terms are used herein. Most incisions will be made along a generally straight line which will define the axial direction. The lateral direction will generally be across the axial direction, typically but not necessarily being perpendicular or normal to the axial direction. Most incisions will be generally linear but in some cases the incisions could be curved or have other geometries. The term "axial" will then apply to the direction of the incision at any particular location, resulting in lateral directions which could also vary.

Figure 1:
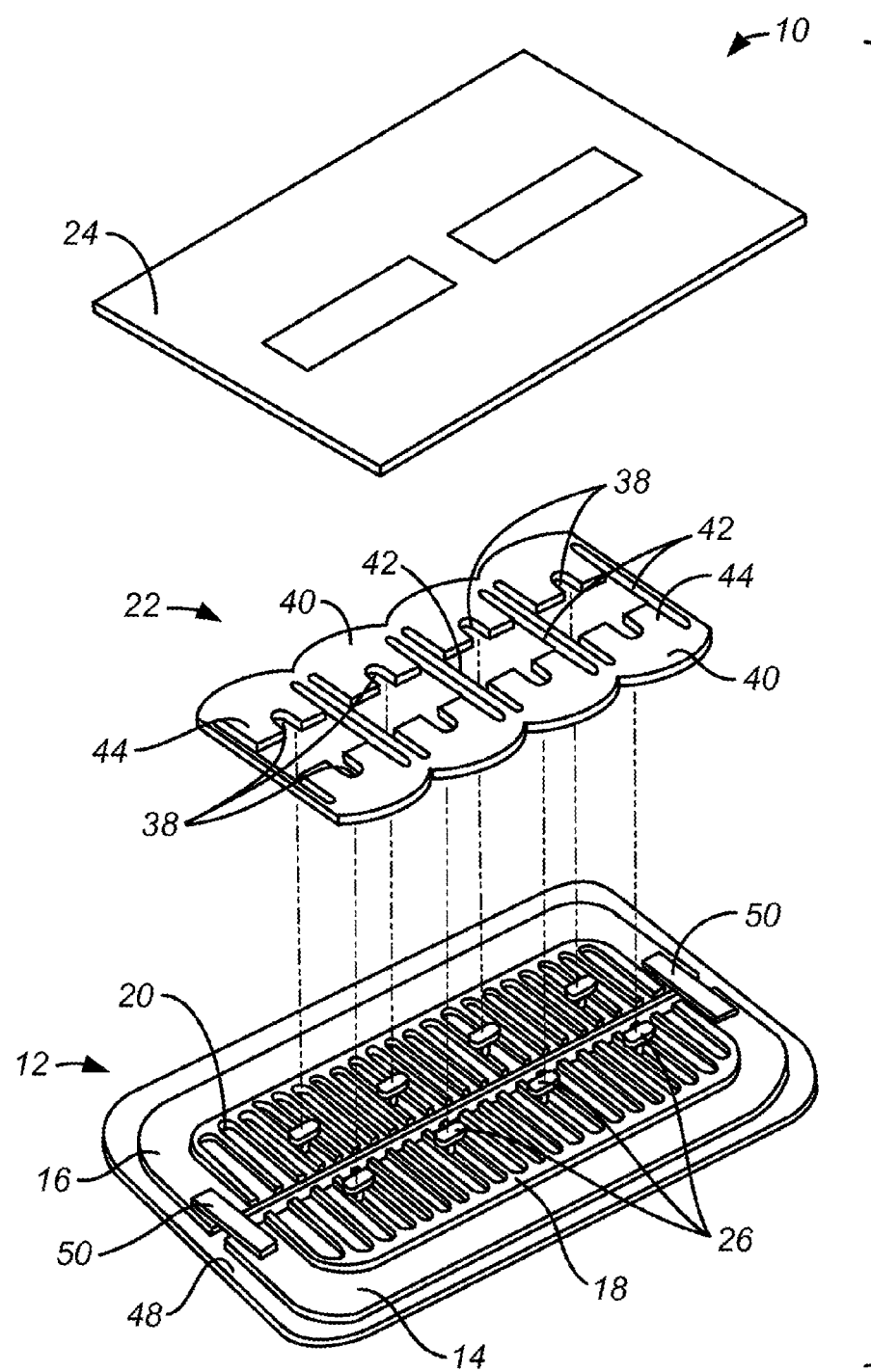
FIG. 1 is an exploded view of an incision closure appliance constructed in accordance with the principles of the present invention.
Figure 2:
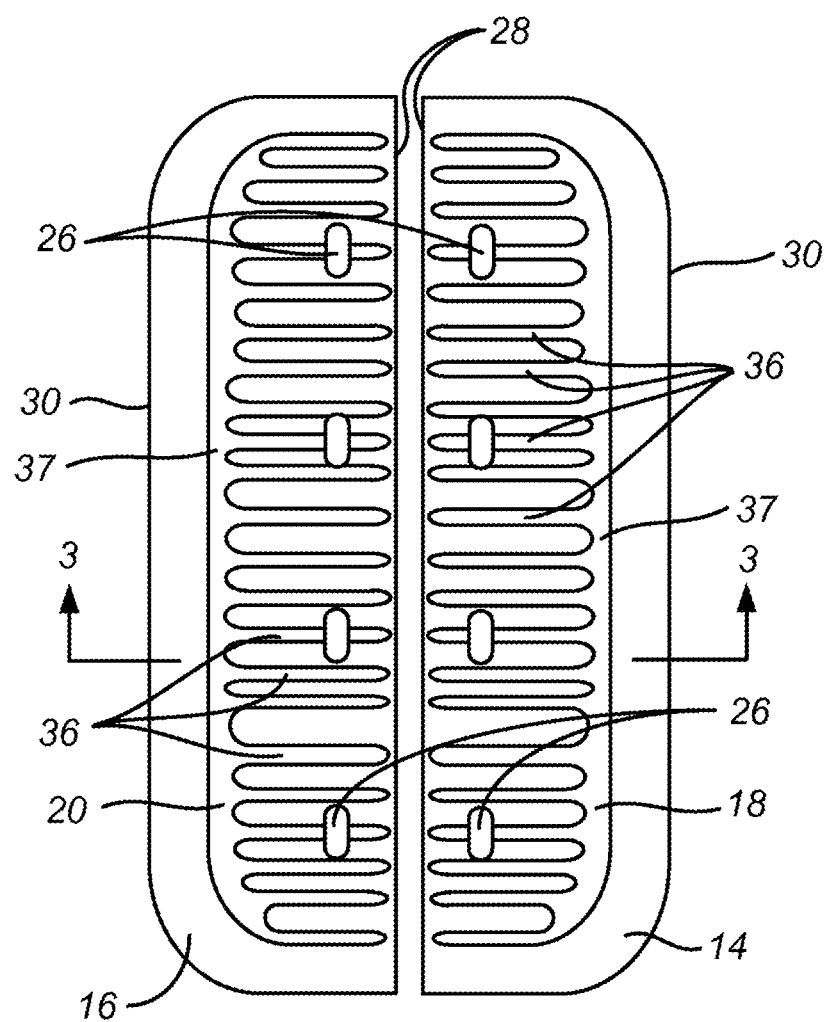
FIG. 2 is a top view of the assembly of a base and a force distribution structure which is part of the incision closure appliance.
Figure 3:
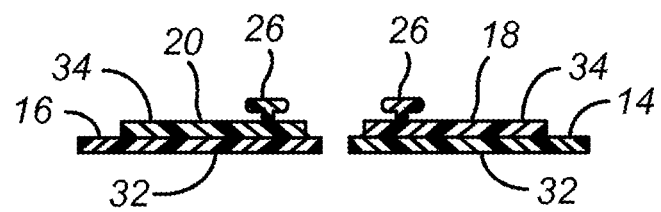
FIG. 3 is a cross-sectional view taken along line 3-3 of FIG. 2.

Referring now to FIGS. 1-3, an incision closure appliance 10 comprises a base assembly 12 including a right panel 14 and a left panel 16. A right force distribution structure 18 is secured to the right panel 14, typically by laminating the force distribution structure to an upper surface of the panel, and a left force distribution structure 20 is similarly attached to an upper surface of the left panel 16. The incision closure appliance further comprises a closure component 22 which is removably attachable to the right and left forced distribution structures 18 and 20 in order to close an incision, as described in more detail below, and the appliance is completed with an optional securing layer 24 which may be placed over the combined base assembly 12 and closure component 22 after they have been secured to the patient and the incision has been closed by drawing the panels together using the closure component.

The closure component 22 is intended and adapted to draw the inner portions of the force distribution structures 18 and 20 inwardly toward each other to close a surgical incision which has been formed therebetween. In the illustrated embodiment, a plurality of cleats 26 are formed on lateral supports 36 which are held axially by spine 37 of the force distribution structures 18 and 20. The cleats 26 are received in slots 38 formed along inner edges of opposed engagement members 40 of the closure component 22. The opposed engagement members 40 are held together by lateral struts 42 so that the engagement members are held at a fixed, laterally spaced-apart distance (in other embodiments the spaced-apart distance may be adjustable). The slots 38 are preferably formed on flexible tab-like structures 44 which allow the slots to be pulled upwardly over the corresponding cleats in order to secure the closure component 22 over the force distribution structures 18 and 20.

The lower surfaces 32 of each panel 18 and 20 will typically be covered with a pressure-responsive adhesive, where the adhesive is initially covered with a protective layer 48 which may be peeled away immediately prior to use. Additionally, pull-away tabs 50 or other similar structures may be provided in order to hold the right and left panels 14 and 16 together at a pre-determined spaced-apart distance after the layer 48 has been removed but prior to adhering the panels to a patient's skin or other tissue surface. It is important that the distance between the inner edges 28 of each panel 14 and 16 be maintained as close as possible to the original target spacing so that the tissue edges, when closed by the closure component 22, will be precisely brought together, typically with a slight eversion.

Figure 4:
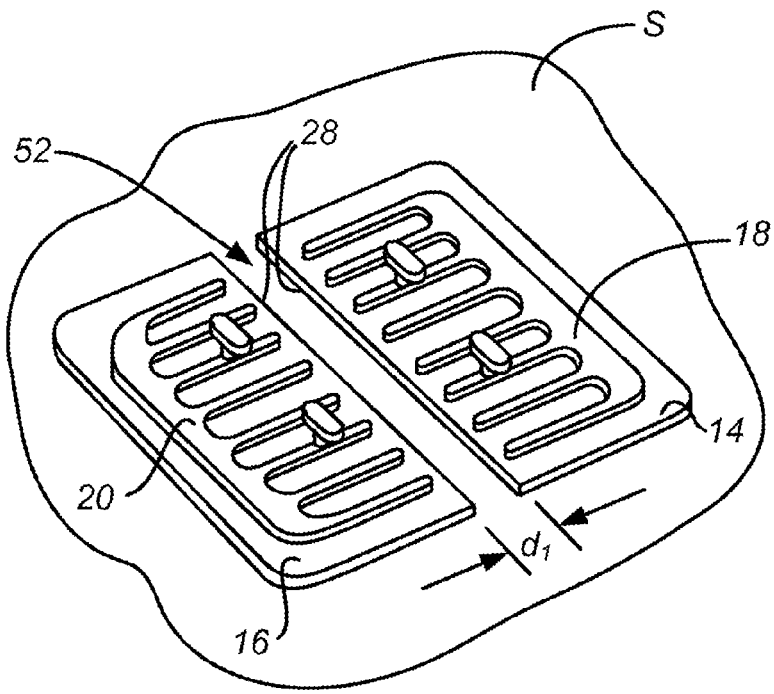
FIGS. 4-7 illustrate use of the incision closure appliance of the present invention for forming and closing an incision in a patient's skin.

Referring now to FIGS. 4 through 7, a protocol for both forming an incision and subsequently closing the incision in accordance with the principles of the present invention will be described. Initially, the right and left panels 14 and 16 are placed on the patient's skin followed by reference letter S, as shown in FIG. 4. The panels 14 and 16 are applied by first pulling away the protective layer 18 and placing the panels onto the tissue, after which time the tabs 50 may be removed, leaving an incision path 52 defined between the inner edges 28. The spacing of the inner edges 28 will be selected to provide a fixed, pre-determined distance $d_1$.

Figure 5:
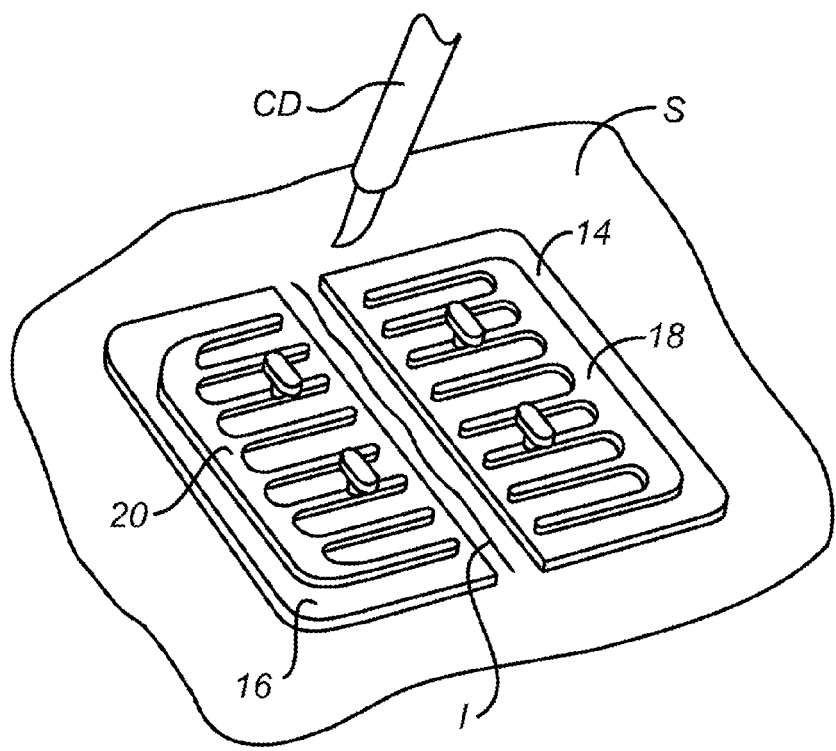

After the right and left panels 14 and 16 are in place, an incision I can be formed in the space between the panels using a scalpel or other surgical cutting device CD, as shown in FIG. 5.

Figure 6:
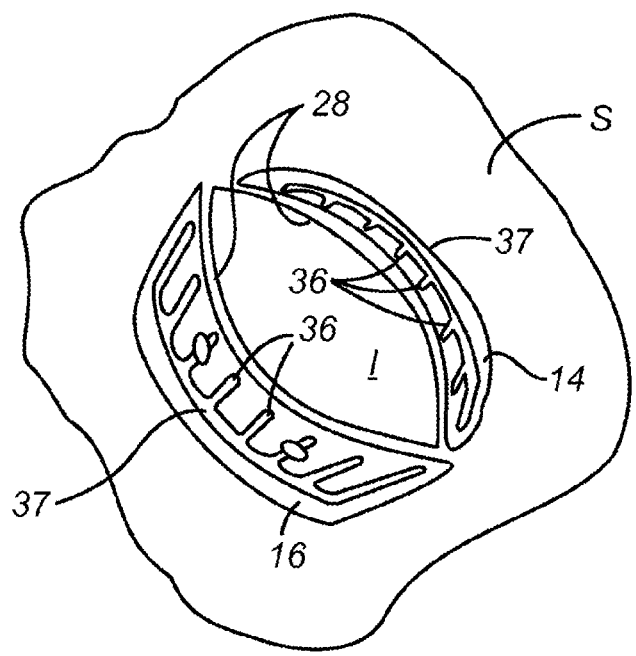

After the incision I is made, a surgical procedure may be performed by opening the inner edges of the incision which in turn deforms the inner edges 28 of the right and left panels 14 and 16, as shown in FIG. 6. As the inner most ends of the supports 36 are not connected, they are free to separate and allow the elastic matrix of the right and left panels 14 and 16 to expand, as clearly in FIG. 6. The dimensional stability of the remainder of the panels, however, will be preserved by the lateral supports 36 as well as the axial spines 37 which do not elongate under the influence of the force applied by stretching opening the incision.

Figure 7:
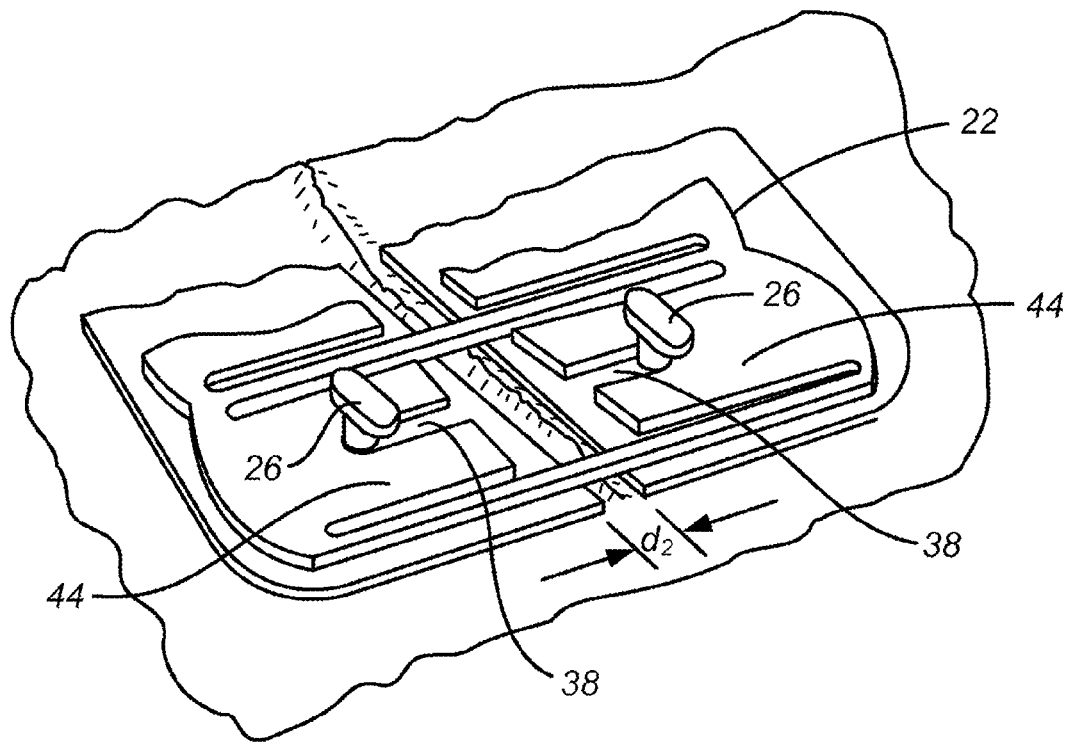

After the surgical procedure is complete, the closure component 22 will be secured over the force distribution structures 18 and 20, as illustrated in FIG. 7. In particular, the slots 38 in the tab-like structures 44 are engaged over opposed cleats 26 in order to draw opposed edges of the panels as well as of the tissue incision together. By properly spacing the depth of the slots 38, the closure component 22 can be tailored so that the panels 14 and 16 are brought together by a pre-selected distance $d_2$. Typically, the distance $d_2$ will be less than the initial separation $d_1$ so that the inner edges of the tissue are brought together to cause the tissue edges along the incision to slightly evert (pucker upwardly) which can improve healing and reduce scarring.

Figure 8:
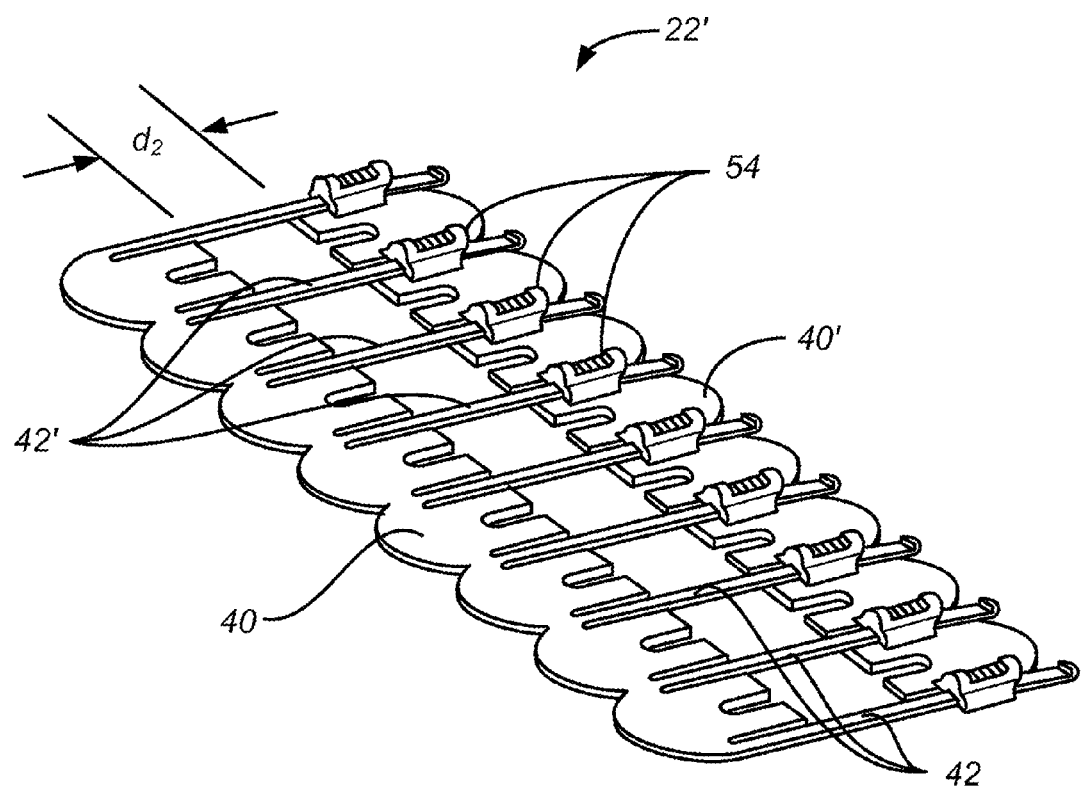
FIG. 8 illustrates an alternative construction of a closure component for the closure appliance of the present invention.

Optionally, as shown in FIG. 8, a closure component 22' may include engagement members 40', where one end of each lateral strut 42' is joined by an adjustable clasp or other mechanism 54 so that the distance between the inner edges of the opposed engagement members 40' can be adjusted in order to increase or lessen the distance $d_2$ therebetween.

Figure 9:
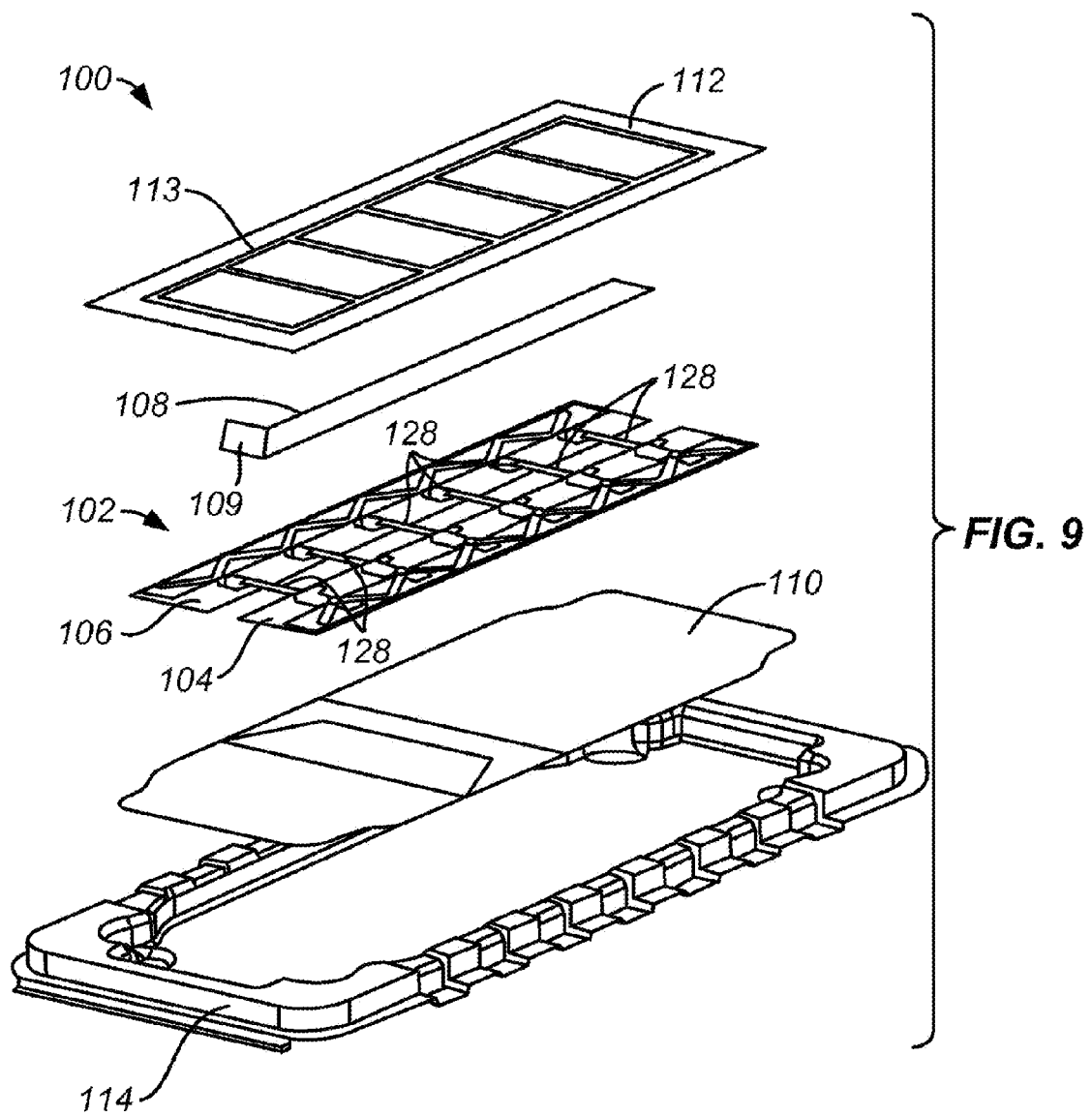
FIG. 9 is an exploded view of a further embodiment of an incision closure appliance constructed in accordance with the principles of the present invention.
Figure 10:
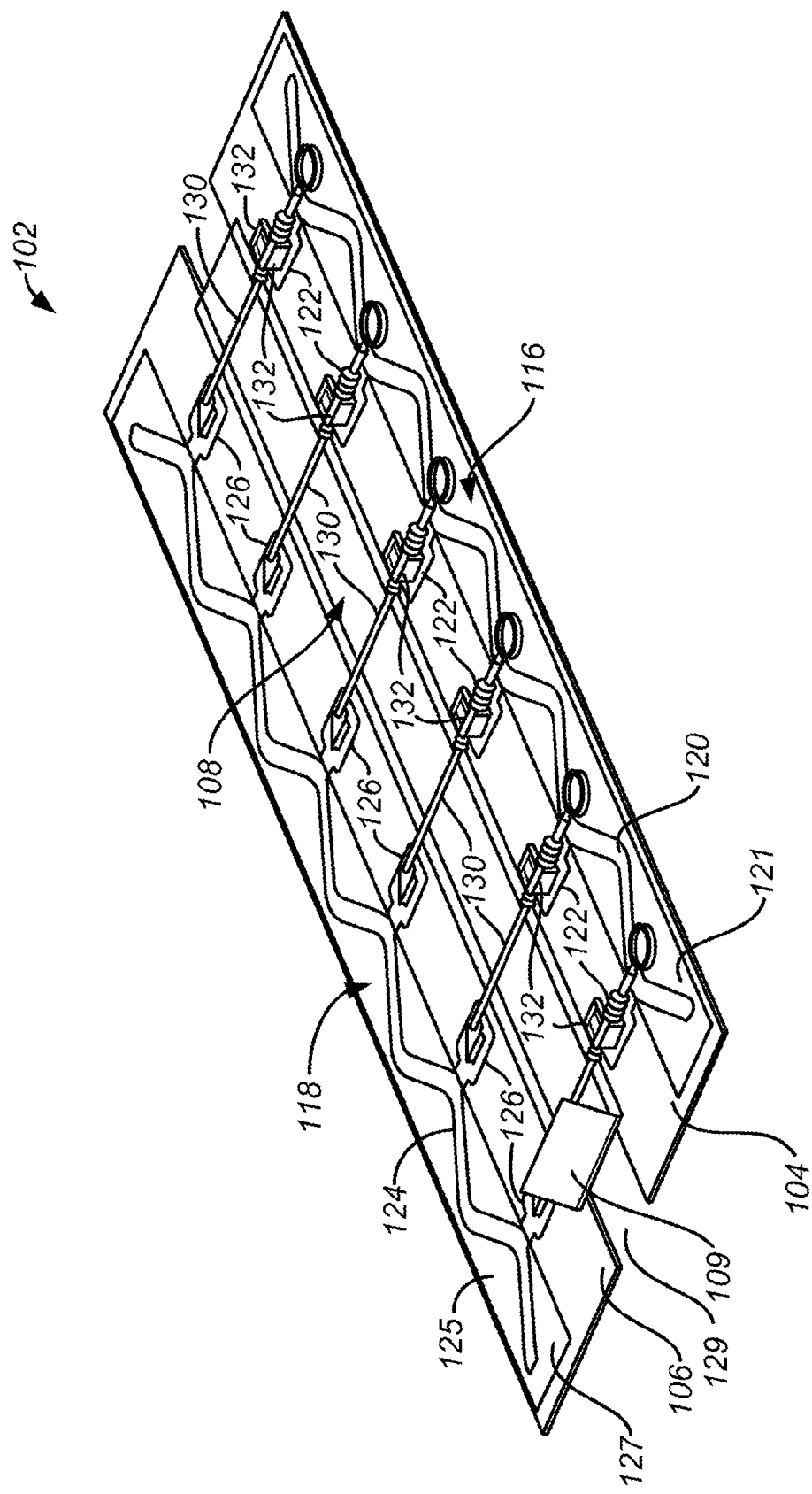
FIG. 10 is an enlarged isometric view of the base and force distribution structure of the system of FIG. 9.

An alternative embodiment 100 of the incision closure appliance of the present invention is illustrated in FIGS. 9 and 10. The appliance 100 includes a base assembly 102 having a right panel 104 and a left panel 106. A positioning or alignment strip 108 is provided to secure the inner edges of each panel together, as shown best in FIG. 10 and includes an end tab 109 that allows the user to pull the strip from the panels 104 and 106 after the panels have been put in place on a tissue surface.

The incision closure appliance 100 further includes a backing 110 having an end which may be partially folded back to expose an underlying adhesive backing on the panels and allow that end of the base assembly 102 to be adhered to the tissue while the remainder of the base assembly is still covered by the backing. A securing layer 112 which includes a reinforcement frame 113 is provided for placement over the right panel 104 and left panel 106 after the base assembly 102 has been closed over an incision, generally is described in connection with the previous embodiment. Usually, a holding tray 114 will be provided for maintain the components of the appliance together in a sterilized condition where the tray 114 will be covered with conventional medical packaging cover.

As illustrated in FIGS. 9 and 10, a right force distribution structure 116 and a left force distribution structure 118 are provided on the upper surfaces of the right panel 104 and the left panel 106, respectively. The right force distribution structure 116 includes a right axial spine 120 and a plurality of lateral supports 122. Typically, the right axial spine 120 comprises a serpentine or zig-zag number which is embedded in or laminated to a base strip 121. The serpentine axial spine 120 would typically be formed from a flexible, resilient plastic, typically a hard plastic, while the base strip 121 will be comprised of a polyurethane or similar plastic layer. The lower surface of the polyurethane layer will be covered with a hydrocolloid layer for tissue adhesion. The structure of the left forced distribution structure 118 will be the same including a left axial spine 124, left lateral supports 126, and a left base strip 127.

The incision closure appliance 100 will include a closure mechanism comprising a plurality of lateral tie assemblies 128 as shown on FIG. 9. As best seen in FIG. 10, each lateral tie assembly 128 will include a rod which is secured at one end to the left lateral support 126 and a ratchet mechanism 132 which is secured to the right lateral support 122. Each rod 130 will usually be aligned with the axis of the left panel 106 parties so that a gap 129 between the right panel 104 and left panel 106 will be left open so that an incision can be made there between. After the incision is made, each rod 130 will be pulled over to the associated ratchet 132 on the right panel 104. A series of ratchet rings on each rod will be pulled into the associated ratchet mechanism 132, and the rod then pulled laterally until the desired closing tension is applied at that point along the base assembly 102. It is a particular advantage that each of the lateral tie assemblies 128 may be individually adjusted to supply the desired closing tension across the tissue along the length of the incision being closed. Once the desired closing tension has been provided along the entire incision, the securing layer 112 may be placed over base assembly 102 to hold the appliance and tissue in place.

Referring now to FIGS. 11A and 11B, an alternative design for the lateral tie assemblies 140 of the present invention is illustrated. These lateral tie assemblies 140 may be utilized with either of the incision closure appliances 10 or 100 described previously. Each lateral tie assembly 140 includes a right force distribution structure 142 and a left force distribution structure 144. The right force distribution structure includes a right spine 146 and a plurality of lateral supports 148. Although three are shown, it will be appreciated that four, five, six or more lateral supports could be included. The left force distribution structure 144 similarly includes a left spine 150 and a plurality of left lateral supports 152. To provide closure, the right force distribution structure 142 includes a rod 154 which extends from the center lateral support 148. Typically, the rod 154 is joined to the support by a live or passive joint 158. A pull loop 156 is provided at the free end of the rod 154, and a plurality of ratchet teeth 162 are provided along the midsection of the rod 154.

The left force distribution structure 144 includes a ratchet mechanism 160 adapted to receive the teeth 162 on the rod 154 of the right force distribution structure. In this way, the rod 154 can be lowered into the ratchet 160 to engage teeth 162, allowing the rod to be pushed forward in order to draw the right and left force distribution structures 142 and 144 together in order to apply tension to the right and left panels.

Figure 12:
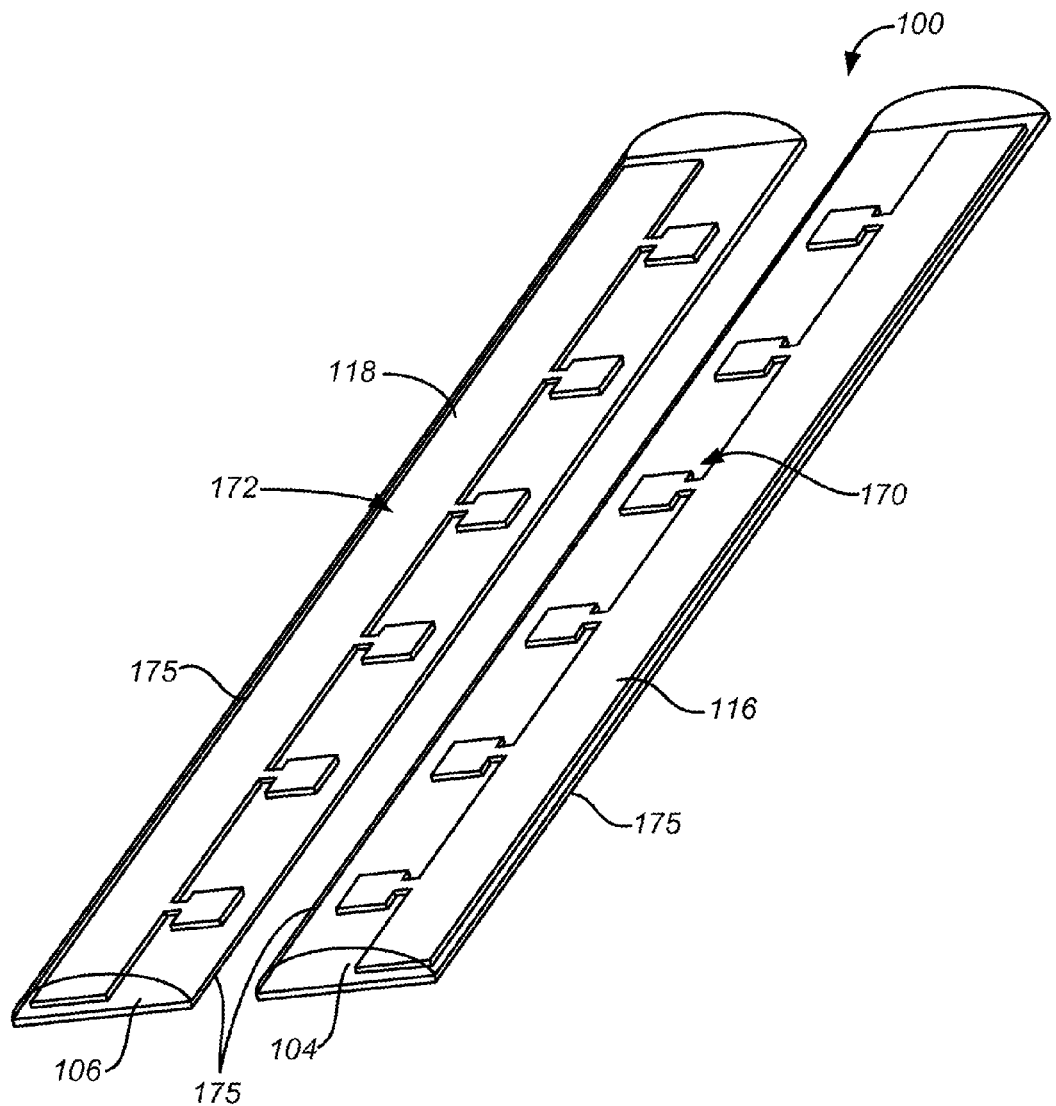
FIG. 12 illustrates a sacrificial cover positioned over an incision closure appliance in accordance with the principles of the present invention.

As illustrated in FIG. 12, a further aspect of the present invention is illustrated. The incision closure appliance 100 is illustrated schematically with only the right and left panels 104 and 106 and the right and left force distribution structures 116 and 118 being illustrated. The remaining system components are not shown for ease of illustration.

The right panel 104 is covered by a right sacrificial cover 170 and the left panel 106 is covered by a left sacrificial cover 172. The right and left panels 104 and 106 may define a region 175 where the right and left sacrificial covers 170 and 172 separates from the right and left panels 104 and 106. Each cover 170 and 172 is detachably secured along each edge of the associated base panel so that the covers remain in place during normal handling and placement of the incision closure appliance 100 over the tissue surface to be incised. The use and purpose of these sacrificial covers 170 and 172 is described with reference to FIGS. 13A and 13E.

Figure 13A:
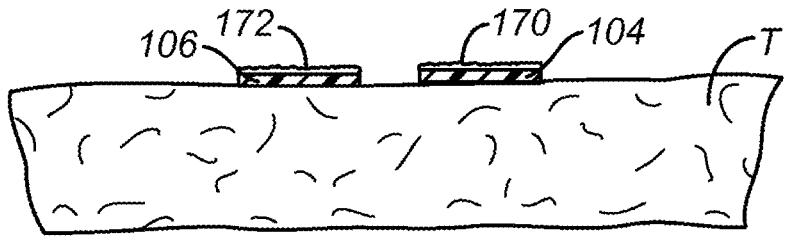
FIGS. 13A through 13E illustrate the principle of operation of the sacrificial cover illustrated in FIG. 12 when used together with a surgical incision drape and performing methods according to the present invention.
Figure 13B:
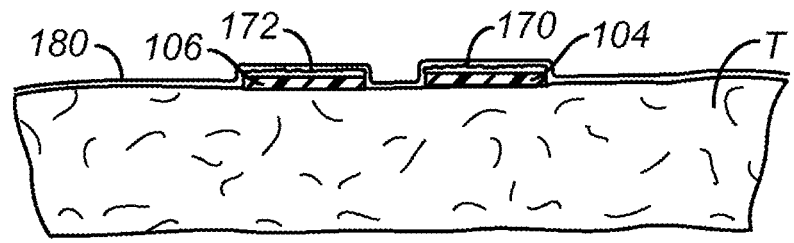
Figure 13C:
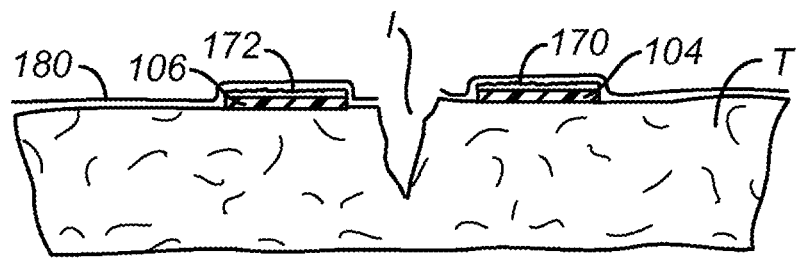

FIG. 13A illustrates the right and left panels 104 and 106 in place on a tissue surface T prior to an incision being made. The right panel 104 is covered by right sacrificial cover 170 and the left panel 106 is covered by left sacrificial cover 172. As is common in many surgeries, an adherent surgical incision drape 180 is placed over the tissue surface T. Any conventional drape may be used such as the Ioban™ antimicrobial incise drape, available from 3M, St. Paul, Minn.

Figure 13D:
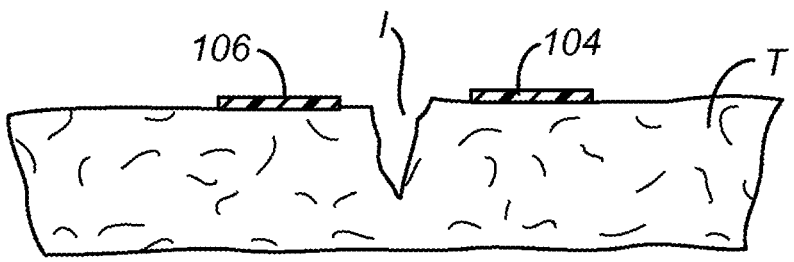
Figure 13E:
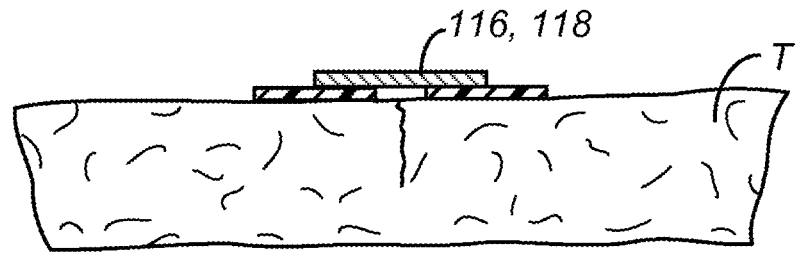

After the incision drape 180 is in place over the incision closure appliance, a surgical incision I may be made for performing a desired surgical intervention. As can be seen, the incision I will cut through the surgical drape 180 between the right and left panels 104 and 106, respectively. After the surgical procedure is completed, the surgical drape 180 will be removed from the tissue surface T. As the surgical drape has a lower adherent surface, prior to the present invention, removal of the drape might have displaced either or both of the right panel 104 and left panel 106. Presence of the sacrificial layers 170 and 172, however, prevents such displacement. Removal of the surgical drape 180 will remove the sacrificial layer 170 and 172, but as each of these layers is configured to break off with a relatively low separation force, removal of the sacrificial layers will not cause the underlying panels 104 or 106 to be displaced. Thus, the panels 104 and 106 will be left in place, as shown in FIG. 13D, and the force distribution structures 116 and 118 can be used as described previously for closing the panels together to close the incision as shown in FIG. 13E.

Figure 29:
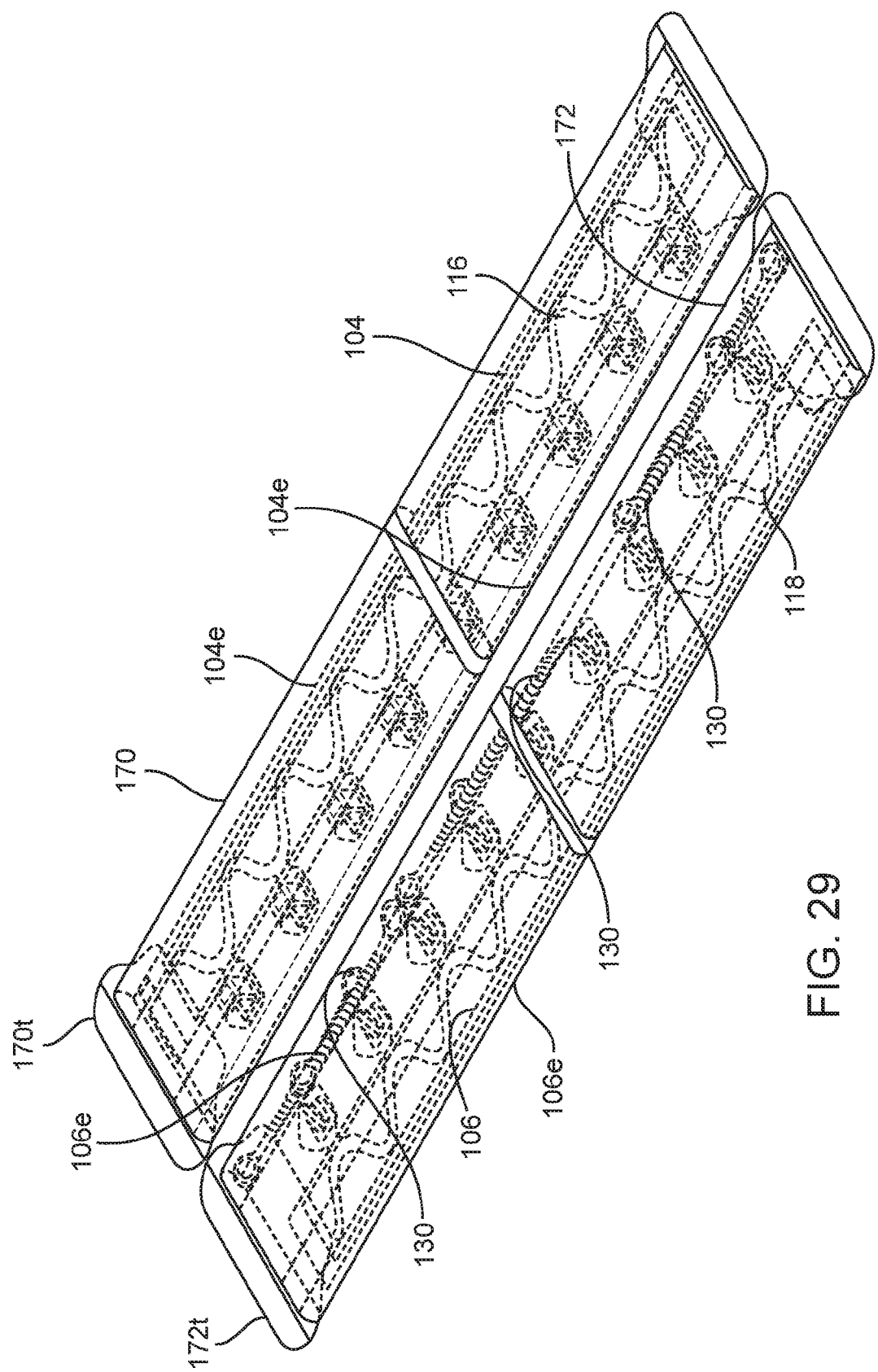
FIG. 29 illustrates another sacrificial cover positioned over an incision closure appliance in accordance with the principles of the present invention

Referring to FIG. 29, the right and left sacrificial cover layers 170 and 172 may each be constructed from a thin sheet of urethane (e.g., 0.001" thick). The middle of the urethane sheets may be adhered to the top of the right and left panels 104 and 106, with the force distribution structures 116, 118 as well as any straps 130 and locks 132, assembled on top of the urethane sheets. The urethane sheets may then wrapped around the force distribution structures 116, 118 (and the straps 130 may be bent inward as shown in FIG. 29 such that they are contained over the panel 106) with the free ends of the urethane laminated to one another along their length. Thus, the urethane sheet may wrap over the force distribution structures 116, 118 and closure elements 130, 132 to protects them from the surgical drape 180. The urethane sheet may preferably comprise a plurality of perforations disposed along its length and aligned adjacent with the inner and outer edges 104e, 106e of each panel 104, 106. The perforations may allow the urethane sheet to tear away with the surgical drape 180 in a controlled manner when a surgical drape, e.g., the surgical drape 180 described herein, is removed. The perforations may preferably be constructed of a 3 mm cut and 1 mm tie, though exact dimensions may be varied to control the desired tear force. The perforations may be formed along a single longitudinal line, or a plurality of lines. A plurality of longitudinal perforation lines may allow for reliable separation despite variations in which the surgical drape adheres to the sacrificial layers 170, 172. The perforations could be made to release more easily near the edge of the panels 104, 106 to help improve the likelihood of separation near the edges 104e, 106e of the panels 104, 106 and minimize excess urethane being left behind. To aid in the lift of the sacrificial layers 170, 172, tabs 170t, 172t may be adhered to each end of the urethane wrap comprising the sacrificial layers 170, 172. The tabs 170t, 172t may preferably be adhered to the inside of the upper surface of the urethane wrap. The tabs 170t, 172t may be shaped to prevent adhesion of the urethane to itself or to any exposed adhesive from the ends of each panel 104, 106. Pre-breaking of the perforations at the end of each panel 104, 106 may aid in the initial lift of the tab 170t, 172t and initiation of the tear by the user.

Referring now to FIGS. 14A1-14A3, further embodiments of incision closure appliances are illustrated. The base assemblies 1400a (FIG. 14A1), 1400b (FIG. 14A2), and 1400c (FIG. 14A3) may each comprise a right base panel 1402 and a left base panel 1404. The right base panel 1402 may comprise an upper layer 1406 and a lower layer 1408. Similarly, the left base panel 1404 may comprise an upper layer 1410 and a lower layer 1412. The upper layers 1406, 1410 will typically be flexible but stiff enough securely close tissue and minimize disruption of the incision and surrounding tissue. The upper layers 1406, 1410 may comprise a plastic layer made of rubber, latex, polyurethane, silicone, a thermoplastic elastomer, a woven fabric, a spun fabric, or similar materials. The adhesive bottom layers 1408, 1412 will typically be flexible and more elastic than the upper layers 1406, 1410 to follow any movement of the underlying skin and tissue to maintain adhesion, minimize blistering, and otherwise reduce irritation. The adhesive bottom layers 1408, 1412 may comprise a hydrophilic adhesive material such as a hydrocolloid, a hydrogel, an acrylic polymer, poly (ethylene glycol), and the like.

The right and left base panels 1402, 1404 may comprise structures to facilitate and limit axial and lateral stretching of the base assembly 1400. These structures may also evenly distribute the closure force exerted on an incision and may be disposed on the base assemblies 1400a, 1400b, and 1400c along their axial length. The right base panel 1402 may comprise one or more right force distribution structures or axial supports 1414. Each right axial support 1414 may comprise an axial support portion or spine 1414a and two lateral support portions 1414b coupled to the axial ends of the spine 1414a. Together, the spine 1414a and the two lateral support portions 1414b form a C-shape which in some embodiments can open axially to a degree to facilitate axial stretching of the right base panel 1402 between two laterally adjacent lateral support portions 1414b of adjacent supports 1414 while limiting the axial stretching between the two lateral support portions 1414b of a single support 1414. In many embodiments, the C-shaped axial support 1414 is only flexible enough to allow flexing vertically but is stiff to minimize axial and lateral stretching. As shown in FIG. 14A1, the right axial supports 1414 may be inward facing. As shown in FIGS. 14A2 and 14A3, the right axial supports 1414 may be outward facing which may help to distribute any mechanical load against the tissue closure to the incision I between the right and left base panels 1402, 1404. Similarly, the left base panel 1404 may comprise one or more left force distribution structures or axial supports 1416. Each left axial support 1416 may comprise an axial support portion or spine 1416a and two lateral support portions 1416b coupled to the axial ends of the spine 1416a. Together, the spine 1416a and the two lateral support portions 1416b form a C-shape which in some embodiments can open axially to a degree to facilitate axial stretching of the left base panel 1402 between two laterally adjacent lateral support portions 1416b of adjacent supports 1416 while limiting the axial stretching between the two lateral support portions 1416b of a single support 1416. In many embodiments, the C-shaped axial support 1416 is only flexible enough to allow flexing vertically but is stiff to minimize axial and lateral stretching. As shown in FIG. 14A1, the left axial supports 1416 may be inward facing. As shown in FIGS. 14A2 and 14A3, the left axial supports 1416 may be outward facing which may help to distribute any mechanical load against the tissue closure to the incision I between the right and left base panels 1402, 1404.

As shown in FIG. 14A3, the base panel assembly 1400c may further comprise skirts 1424 and 1426. The skirts 1424, 1426 may be similar to the thin base assembly covers described below. For example, each skirt 1424, 1426 may comprise a 0.001 inch thick urethane film coupled to a 0.002 inch thick acrylic adhesive. The adhesive may be applied to the whole under-surface of the skirts 1424, 1426 or may just to the region of the skirts 1424, 1426 beyond the base panels 1402 or 1404. During construction of the base panel assembly 1400c, the skirts 1424, 1426 may be applied directly over all or a portion of the adhesive layers 1408, 1412, respectively. The skirts 1424, 1426 may be applied in place of, or in addition to, the thin film upper layers 1406, 1410, respectively. Release liners as described herein may further be provided to line the adhesive under-surface of the skirts 1424, 1426. The skirts 1424, 1426 may extend beyond the outer border of the base panels 1402, 1404, respectively, by 8 mm or in a range of 1 to 20 mm, for example, but does not span across the lateral area between the base panels 1402, 1404 to improve the ability to visualize and/or clean the incision site. Thus, the skirts 1424, 1426 may help provide additional adhesive support and/or creep reduction to the adhesive layers 1408, 1412 of the base panels 1402, 1404 without having to align and place a separate cover or cover sheet over the base panel assembly 1400. After manufacturing, the skirts 1424, 1426 are typically already precisely aligned relative to the base panels 1402, 1404. A separate cover or cover sheet as described herein may still be used to prevent tampering of the incision site and components of the base panel assembly 1400c. As the skirts 1424, 1426 already laterally extend over the base panels 1402, 1404, respectively, such a separate cover or cover sheet may not require precise placement relative to the base panel assembly 1400c and could be more narrow compared with other covers or cover sheets described herein.

One or more perforations 1418 may be provided in-between axially adjacent right axial supports 1414 on right panel 1402 to facilitate the axial and/or lateral stretching of the right base panel 1402. The perforations 1418 may be all the way through the upper and lower layers 1406, 1408 to provide aeration to the underlying tissue or may only be present on the upper layer 1406. Similarly, one or more perforations 1420 may be provided in-between axially adjacent left axial supports 1416 on left panel 1404 to facilitate the axial and/or lateral stretching of the base panel 1402. The perforations 1420 may be all the way through the upper and lower layers 1410, 1412 to provide aeration to the underlying tissue or may only be present on the upper layer 1410. As shown in FIG. 14A1, there may only be a single perforation 1418 or 1420 between the axial supports 1414 or 1418. As shown in FIGS. 14A2 and 14A3, there may be a plurality of perforations 1418 or 1420 in a lateral line between the axial supports 1414 or 1418. The perforations 1418, 1420 may also reduce the stress incurred as the skin stretches radially outward from the incision I such as during joint articulation and swelling.

Figure 14B:
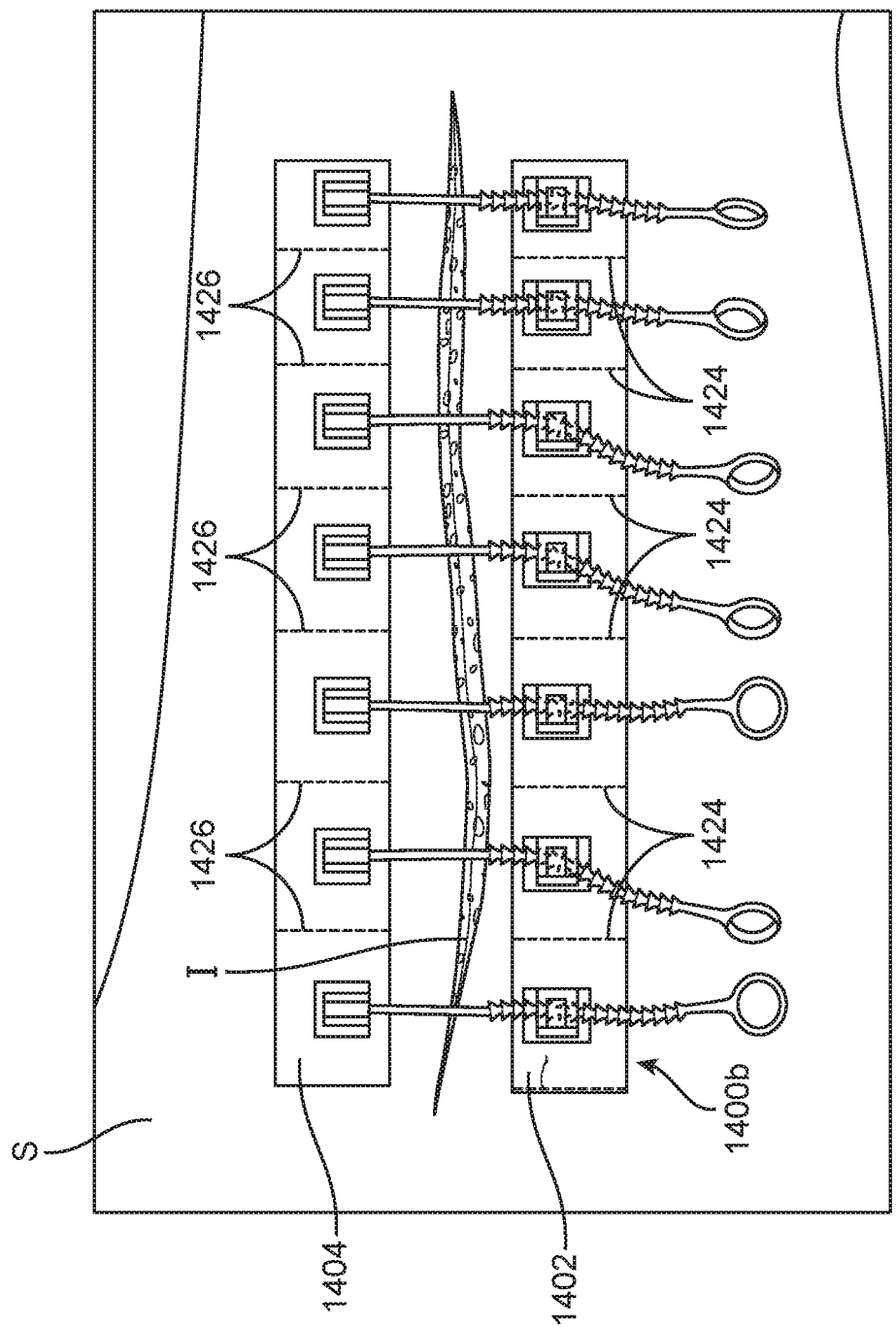
FIG. 14B is a top view of an incision closure appliance similar to that of FIGS. 14A-14A3 and which is placed on the knee of a subject according to the present invention.

A plurality of perforations 1418, 1420 may, for example, be provided in-between the axial ends of the right and/or left axial supports 1414, 1416 along the right and left lines 1424, 1426 shown in FIG. 14B. A plurality of axially-aligned perforations may be provided on each line segment 1424 or 1426 such that at least the upper and lower layers 1410, 1412 of the base panels 1402, 1404, respectively, may break into separate segments when axially stretched as further described below. In some instances, during the wear duration of the device 1400, the perforations 1418, 1420 may allow the layers 1406 and 1408 of right panel 1402 and the layers 1410 and 1412 of left panel 1404 to completely divide and separate at the perforation line, which is shown in FIGS. 14A2 and 14A3. The ability to completely divide and separate further allows the skin to stretch axially as needed, with the elongation allowed (and limited) by the linkages of axial supports 1414 and 1416 and closure components 1422 discussed below. As discussed herein, a flexible, compliant cover may be applied over the base panels 1402, 1404 after the incision I is closed. The cover may further serve to provide (and limit) axial and lateral movement of the base structure 1400b. Alternatively or in combination, one or more of the right or left base panels 1402, 1404 may be laterally cut and separated in-between the force distribution structures or axial supports 1414, 1416 to facilitate the axial and/or lateral stretching of the right and/or left base panels 1402, 1404.

To couple the right and left base panels 1402, 1404 laterally together and optionally to tighten the right and left base panels 1402, 1404 against one another, the base assembly 1400 may further comprise a plurality lateral closure components or tie assemblies 1422. The lateral closure components or tie assemblies 1422 may comprise a ratchet mechanism similar to that of lateral tie assemblies 128 and 140 described above. The lateral tie assemblies 1422 may couple laterally adjacent right and left axial supports 1414, 1416 together, typically at their axial ends. As shown in FIGS. 14A1-14A3, the placement of the right and left axial supports 1414, 1416 on the right and left panels 1402, 1404, respectively, may be staggered or axially offset, and the right and left axial supports 1414, 1416 may be C-shaped structures with lateral end portions 1414b, 1416b that laterally face and align with one another (and are connected to one another by a lateral tie assembly 1422). For example, the far end lateral portion 1414b of a first right axial support 1414 may be laterally aligned with the near end lateral portion 1416b of a first left axial support 1416, the far end lateral portion 1416b of the first left axial support 1416 may be laterally aligned with the near end lateral portion 1414b of a second right axial support 1414, and so forth. Thus, the lateral tie assemblies 1422 and right and left axial supports 1414, 1416 may be connected to one another to form a line of consecutive lateral tie assemblies 1422 and right and left axial supports 1414, 1416, and this line may have a serpentine arrangement that laterally spans the right and left base panels 1402, 1404 (i.e., goes across the distance between the right and left base panels 1402, 1404) as shown in FIGS. 14A1-14A3. The serpentine arrangement of lateral tie assemblies 1422 and right and left axial supports 1414, 1416 may one or more of evenly distribute the closure forces provided by the base assembly 1400 on an incision, provide (and limit) axial flexibility of the base assembly 1400, and provide rigidity or stiffness to the base assemblies 1400a, 1400b, and 1400c to sufficiently close an incision and allow it to heal with minimized disruption and distension (i.e., provide lateral and axial stability). In many embodiments, the lateral supports 1414, 1416 are stiff so that the areas of the base panels 1402, 1404 that are not covered with the lateral supports 1414, 1416 stretch. Because these uncovered areas are offset from one another from the right base panel 1402 to the left base panel 1404, the tie assemblies 1422 may pivot axially from their anchor points as the incision I is axially stretched. Such axial pivoting of the tie assemblies 1422 may bring the left and right panels 1402, 1404 closer together to maintain the closure of the incision I.

The material of the lateral tie assemblies 1422 and the right and left axial supports 1414, 1416 may include, for example, a flexible, resilient plastic, typically a hard plastic, such as Nylon, Polypropylene, Polyethylene, Poly carbonate, and other thermoplastic polymers. Often, the lateral tie assemblies 1422 and the right and left axial supports 1414, 1416 may comprise a material less elastic than that of the right and left base panels 1402, 1404. Thus, as with many other base assemblies of incision closure appliance disclosed herein, greater stiffness (and less elasticity) may be provided toward the top of base assemblies 1400a, 1400b, and 1400c. In other words, there may be an elasticity gradient between the top and bottom of the base assemblies 1400a, 1400b, and 1400c. The tops of the base assemblies 1400a, 1400b, and 1400c may be sufficiently rigid or stiff so that the incision closure appliance, when applied to an incision and surrounding tissue, prevents movement of tissue laterally adjacent the appliance to not substantially distend the covered incision and surrounding tissue. That is, movement of at least a portion of the applied incision closure appliance (e.g., a portion below the more stiff layers) is collective and does not disrupt the underlying incision. And, the bottoms of the base assemblies 1400a, 1400b, and 1400c may be sufficiently elastic such that blistering and adhesion loss due to movement of tissue adjacent the applied incision closure appliance are minimized. While a primary function of lateral tie assemblies 1422 may be to apply tension to each base panel 1402, 1404 to hold the incision I closed, in many embodiments, the lateral tie assemblies 1422 may also serve to provide columnar strength so as to isolate the incision I by minimizing effects of compression on (or bending/creasing along) the incision I from distraction forces that could disrupt the incision edge alignment and apposition. The axial spacing, material property, and dimension of the lateral ties 1422 may be optimized for sufficient axial bending flexibility and lateral compression and bending support. In preferred embodiments, the spacing between ties 1422 is 10 mm, the material of the ties 1422 is nylon, and the dimension is a round cross-section of 0.030 inch.

Referring now to FIG. 14B, the base assembly 1400b may be placed over an incision in the skin of a patient or subject's joint, such as the knee. In incisions placed in proximity to articulating joints, the knee in particular, closure device or closure appliance integrity is often challenged by a number of factors. These factors include longitudinal elongation, circumferential swelling, opening of the wound as articulation occurs, skin damage such as blistering, adhesion loss, and passage of wound exudates. Joints such as knee, elbow, ankle, and shoulder may undergo a movement which can sometimes result in articulation covering more than 135° movements, leading to the challenges noted above.

In a bent position, the skin around the knee can stretch up to 50% axially (i.e., parallel to the incision) and laterally (i.e., transverse or perpendicular to the incision). An incision closure appliance adhered to the skin in this area may preferably be able to provide enough tension to close the incision yet accommodate the stretch with minimal local stress. Minimizing the local stress may prevent local skin adhesion loss or damage to the skin if the adhesive loss does not occur. An important property for many incision closure appliances disclosed herein is the ability of the tension load of the appliance's closure elements to be distributed across an area larger than that of the tension element attachment point itself. Furthermore, the structure comprising the adhesive to which the tensioning elements are attached may in many cases have the ability to distribute the compliance of the structure across the region of skin stretch such that the appliance holds the incision in place while the skin moves around it. Embodiments described herein may include a composite design of non-stretching tension elements (commonly referred to as "straps") that are linked to "locks" that hold the straps in place. For example, such elements may include the lateral tie assemblies 128, 140, and 1422 described above. These elements may be mounted over skin adhesives with elastic polymeric materials that help distribute the tension load. Such elastic polymers may in many cases have high elongation before yielding or permanently deforming and may include thermoplastic elastomers such as polyurethane as well as various grades of silicone. Such materials may also be easily formed into thin films necessary for maintaining a low profile and sufficient compliance.

The skin adhesive used in the appliance may also need to withstand the elongation of the skin and be able to retract/recoil when the skin is returned to an un-stretched condition (e.g., in the fully extended knee position). Hydrocolloid adhesives may provide such properties and may be preferably suited for this application. Other adhesives such as acrylic may also be used to provide this property. In general, such adhesives may need to be attached to an elastic thin film such as that described above in order to hold their structure during expansion and recoil. Without such support, the adhesive may tear and separate with repeated elongation.

Incision closure appliances constructed as a sequence of short segments may accommodate higher overall elongation without loss of adhesion or skin damage. Each individual segment may be subjected to the local stretching of the skin under it. The space between two adjacent segments may act as stress relieving space allowing the skin to stretch in that space. The segmentation may be achieved in number of ways: (1) by laying down individual segments along the incision line, or (2) allowing the device to divide into short segments as it is applied to the skin or after applying to the skin.

A preferred means of achieving segmentation after application to the skin comprises creating perforations (e.g., a lateral line of perforations to facilitate tearing) in the polyurethane layer (i.e., the upper layer 1406, 1410 of a base panel 1402, 1404) as described above and leaving the underlying adhesive intact, as shown in FIG. 14B. The perforations may result in tearing of at least the upper layers (e.g., upper layers 1406, 1410) of the base panels along the perforated lines (e.g., lines 1424, 1426) when it undergoes stretching as the knee flexes (i.e., is articulated). In preferred embodiments, the adhesive panel on each side of the incision may be 12 mm wide, and the perforations within a given panel are spaced about 12-20 mm apart. Experimentation was performed and showed that a perforation of 3 mm cut and 1 mm tie distances are effective in achieving segmentation in 0.001 inch thick urethane base panels when the knee flexes. As the knee flexes, the skin may elongate in axial (along the incision) and lateral directions up to 50% in some locations. Separation of the polyurethane can thus relieve stress in the device as it undergoes stretch.

As an example, a surgically repaired knee may be inflamed for a number of days, which may result in approximately 30% radial swelling of the joint after closure. Elastic materials like polyurethane may allow the incision closure appliance (for example, including the base assembly 1400b adhered to the resulting incision I in FIG. 14B) to expand with this circumferential swelling. Minimizing the width of the appliance (e.g., 12 mm or less for each base panel segment 1402, 1404) may minimize the amount of the appliance subject to expansion in a direction perpendicular to the incision I, and may thus preserve adhesion while minimizing potential for skin damage. FIG. 14B shows perforations in adhesive segments running in the lateral direction to the incision along lines 1424, 1426 to allow easier stretch axially. Perforations or other fenestrations could also be made near the outer edges of the adhesive segments parallel to the incision in order to reduce the stress incurred as the skin stretches radially outward from the incision such as during articulation and swelling.

Figure 15A:
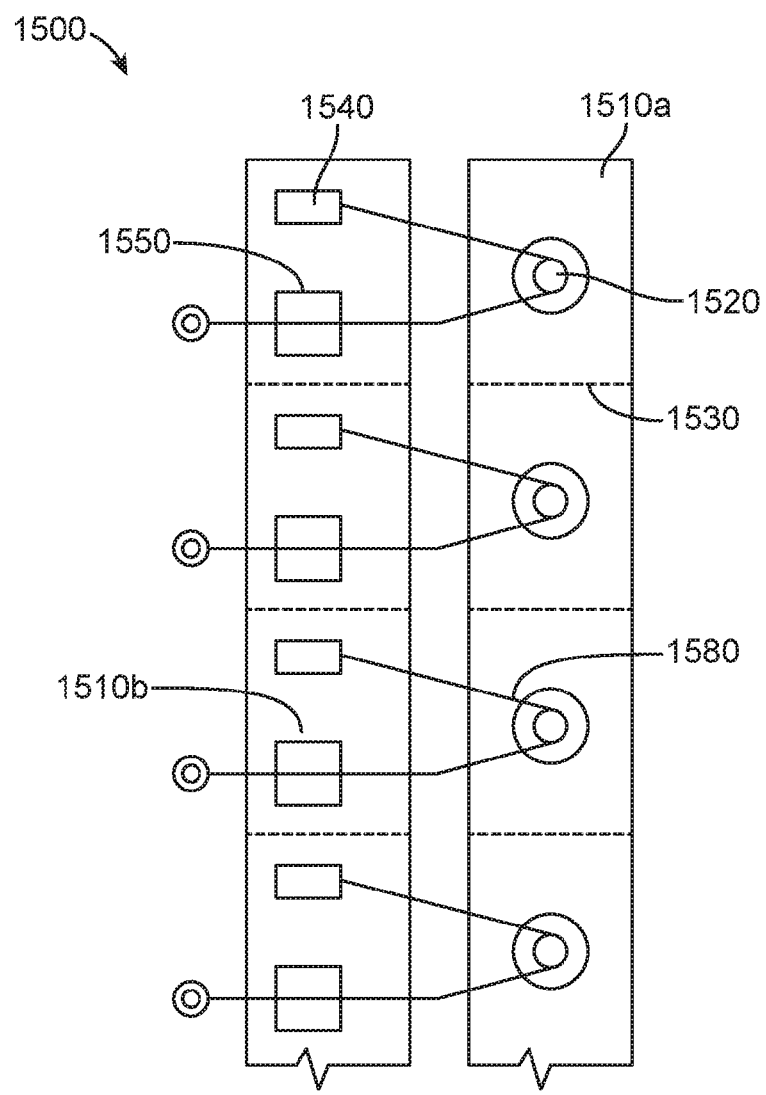
FIG. 15A shows a schematic of an incision closure appliance having a pulley system to laterally couple two adjacent base panels in accordance with the principles of the present invention.
Figure 15B:
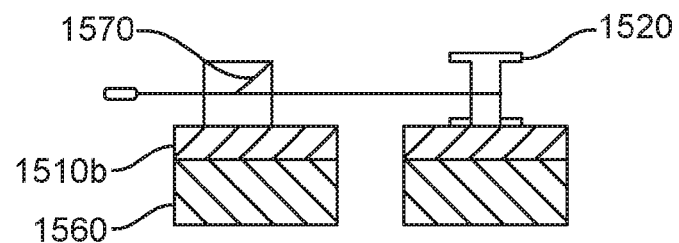
FIG. 15B shows a sectional view of the incision closure appliance of FIG. 15A.
Figure 15C:
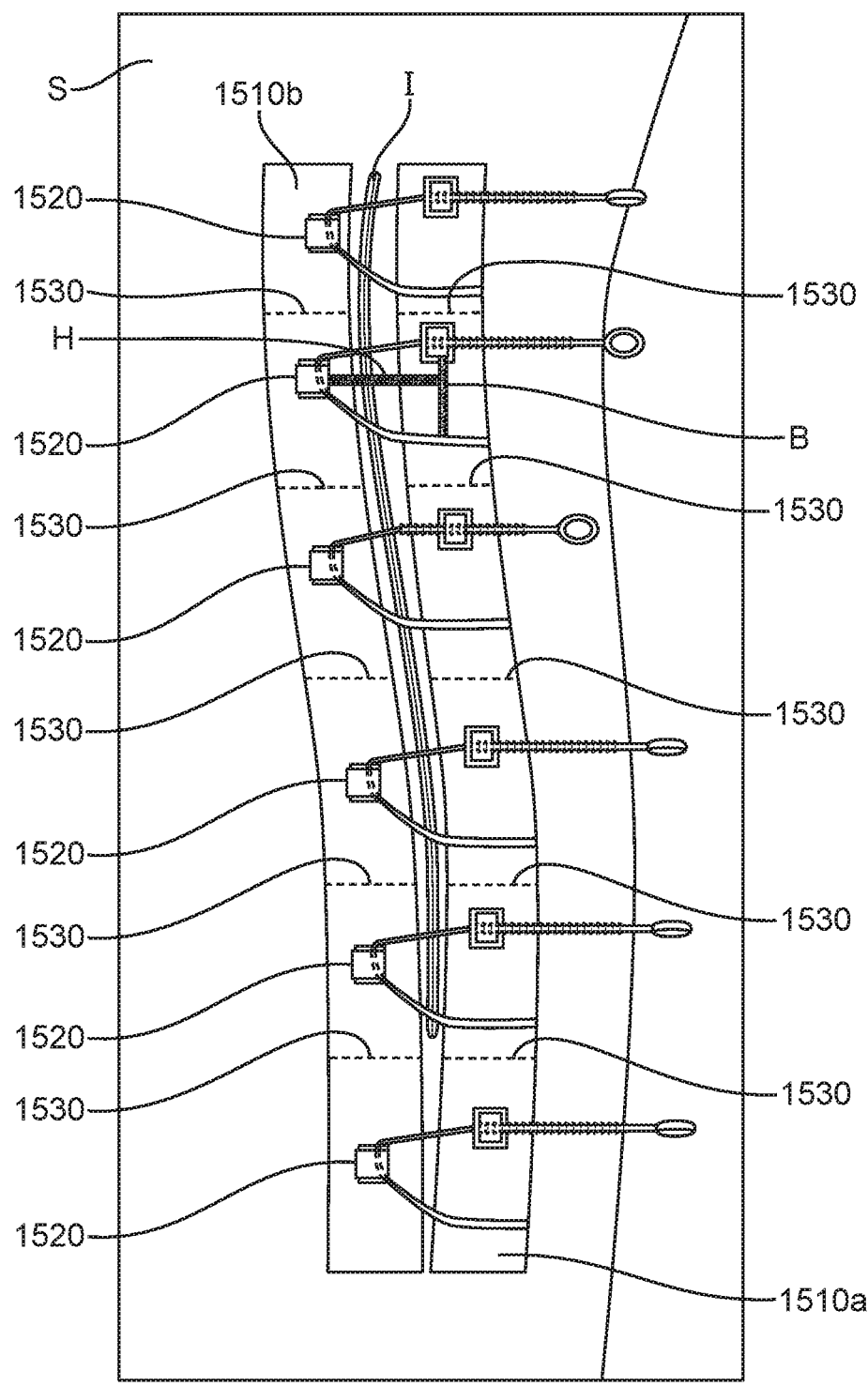
FIG. 15C shows the incision closure appliance of FIG. 15A placed on a model knee according to the present invention.

Referring now to FIGS. 15A-15D, an incision may often experience forces that tend to open the incision due to the flexion of the knee or other joint. In many embodiments, an incision closure appliance is provided with a locking mechanism that counters the opening forces by closing tightly during flexion to assist in keeping the incision closed. FIGS. 15A and 15B shows a base assembly 1500 of an incision closure appliance that comprises a mechanism that leverages the pulley effect, i.e., when the skin stretches along the incision, the distance between the locking points on either side of the incision shortens. In preferred embodiments, the adhesive panels 1510a, 1510b on each side of the incision between the base panel 1510a, 1510b pairs is 12 mm wide, and the lined perforations 1530 within a given panel 1510 are spaced about 18 mm apart. Typically, all the members of the locking mechanism are non-stretching. The triangle formed by the anchor 1540, pulley 1520, lock 1550, and flexible locking element 1580 (e.g., a tether or a strap) has its base B axially along the incision and its height H laterally across the incision, as shown in FIG. 15C. As the knee flexes the triangle base length increases. Typically, all the members of the triangle are non-stretching, which requires that the height must decrease in order to preserve the length of individual elements connecting between any two points, resulting in additional closure forces across the incision. FIGS. 15A and 15B further show that the lower surfaces of the base panels 1510a, 1510b may comprise a hydrocolloid adhesive 1560 and one of the panels 1510a or 1510b may comprise a locking arm 1570 for locking the strap 1580 in place. While the base of the triangle is shown in FIG. 15A on the left base panel 1510*b*, it is contemplated that the base of the triangle may instead be on the right base panel 1510*a*.

Figure 15D:
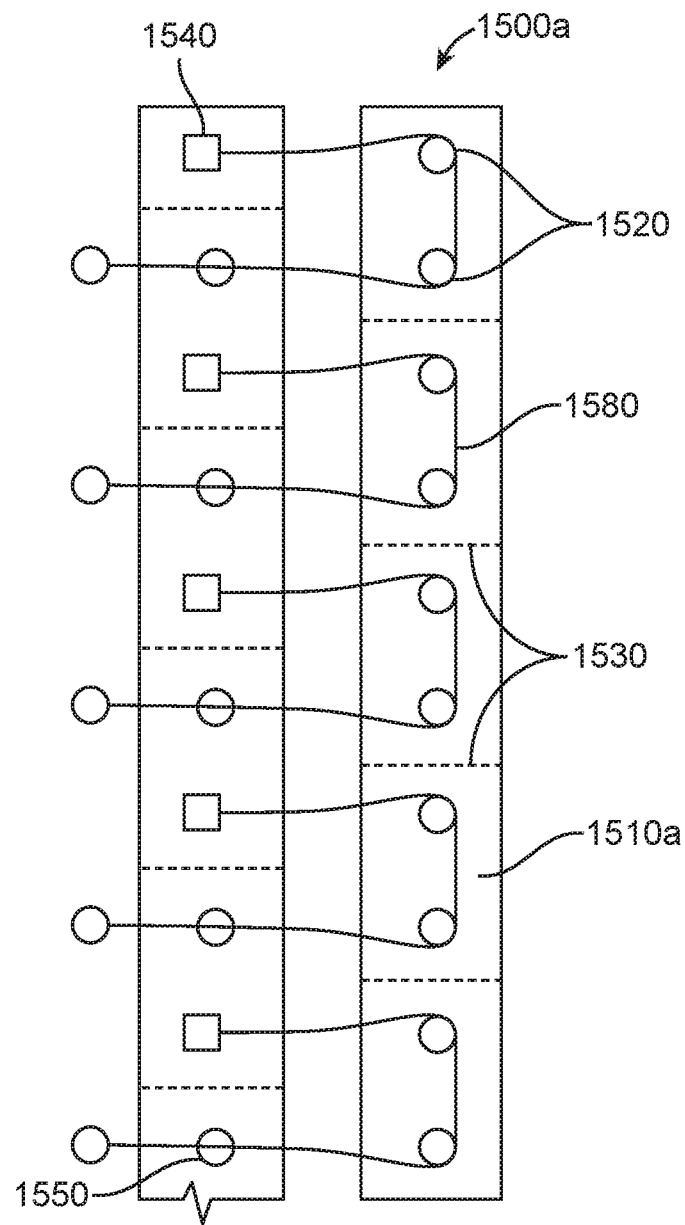
FIG. 15D shows a schematic of an incision closure appliance similar to that of FIG. 15A.

While a triangle is formed by the anchor 1540, pulley 1520, lock 1550, and flexible locking element 1580 other shapes are also contemplated. For example, the pulley 1520 may be wrapped around two anchors 1540 to form a square or rectangular shape, or the pulley 1520 may be wrapped around three or more anchors 1540 to form a trapezoid shape. Referring to FIG. 15D, a base assembly 1500*a* of an incision closure appliance which is similar to the base assembly 1500 is shown. In the base panel 1500*a*, the anchor 1540, the two pulleys 1520, the lock 1550, and the flexible locking element 1580 form a rectangle to provide additional closure at the incision I when the underlying skin stretches. In the rectangular configuration shown in FIG. 15D, the spacing between the two fixed points on either side of the incision I will typically be the same. Whereas in the triangular configuration shown in FIGS. 15A and 15C, the fixed points on the pulley 1520 side may be spaced further apart than the other side of the incision I. While the rectangle is shown as "open" on the left base panel 1510*b*, it is contemplated that the rectangle may be "open" on the right base panel 1510*a* instead.

In the incision closure appliance base assemblies 1400*a*, 1400*b*, and 1400*c* shown in FIGS. 14A1-14A3 and other described herein, individual straps 1422 may be used to engage individual locks on the opposite side of the incision I. In FIGS. 15A-15D, each flexible locking element or strap 1580 is typically anchored on one side of the incision I, wraps around the other side, and then engages a lock 1550 on the same side of the incision I as the location of anchor 1540. In the embodiment shown by FIG. 15D, the flexible locking element or strap 1580 wraps around two fixed spools (bobbin/pulley 1520) on the other side of the incision I before engaging the lock 1550 on the same side. The spools 1520 around which the flexible strap 1580 are wrapped may preferably be linked with a rigid member so that the distance between them does not increase when the closure device base panel assembly 1500 is elongated in the axial direction. In alternative embodiments, allowing expansion between the pulleys or spools 1520 may be desirable. It should be noted that the flexible locking element 1580 may be anchored in one base panel segment while locked in the adjacent segment separated by perforations 1530 in the base panel 1510*a* or 1510*b*. Such anchoring and locking may create a connection among three segments of the base strips—two on the same side and one on the other. When taken together across the length of the incision closure device or base assembly 1500 or 1500*a*, the attachment mechanism forms a continuous 'S' shaped (i.e., serpentine) connections across the incision I.

Figure 15E:
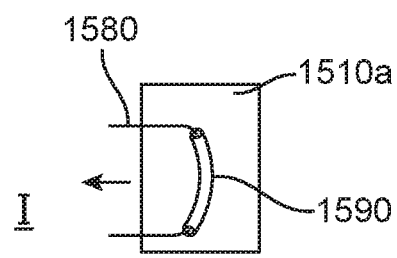
FIGS. 15E and 15F show various lateral tie assembly structures for use with the incision closure appliance of FIGS. 15A and 15D, respectively.
Figure 15F:
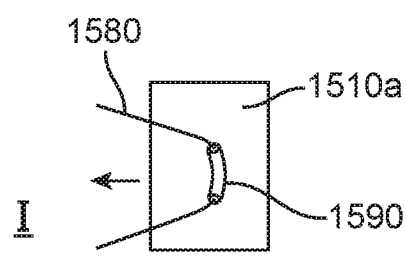

The tensioned flexible connectors 1580 which wrap around the spindles, spools, or pulley 1520 may be configured to provide extra compression of the incision I when the distraction forces attempt to open the incision and the underlying skin experiences stretching. The flexible strap 1580 may in some cases potentially slip from the spindle 1520 and become loose if the two base panels 1510*a* are further compressed by external forces brought together without any stretching of the underlying skin. To prevent such slippage from occurring, the flexible wrapping member 1580 can be slideably contained or anchored within an element 1590 anchored on the base strip 1510*a*. FIGS. 15E and 15F show the flexible element 1580 threaded through a tube 1590 which in turn is attached or anchored to the base panel 1510*a*. When the base panels 1510*a*, 1510*b* are brought closer together, the flexible strap element 1580 will still be captured and will continue to provide the necessary closure function. In other embodiments, the spool features 1590 shown in FIGS. 15E and 15F may have holes through the center which the strap 1590 slides through. The flexible strap 1580 and element 1590 it slides through may preferably be designed to minimize friction between the elements 1580 and 1590.

Experimentation was performed and showed that where the base B is 12 mm and the height H is determined by the distance between the strap connecting points on the two base panels 1510*a*, 1510*b* after the incision is closed (typically about 16 mm), flexing of the appliance 1500 on a human knee resulted in the height H decreasing by 5% in the areas where the elongation of the skin S was maximum. It should be noted that the decrease in height may be dependent on a number of factors such as base of the triangle, level of elongation of the underlying skin and distance between the two bases on either side of the incision. The connecting "straps" between the anchors 1540 and the locks 1550 may need to be at least partially flexible to allow looping around the pulley. In preferred embodiments, a monofilament plastic thread is integrated with features that engage into a locking mechanism. Such features could be rounded "teeth" that engage in a ratchet-like mechanism within the lock. Such a plastic can be used to achieve the desired flexibility, longitudinal rigidity, low propensity to harbor bacteria, and allow for extrusion and/or injection molding processes. A braided suture (preferably coated to limit harboring of bacteria) can also be used to create flexible yet un-stretchable connectors. A round wire or tubing made out of flexible material like silicone can also be used to achieve the flexibility. The strap of the pulley could be a composite of materials such as molded plastic and braided suture. In other embodiments, the strap of the pulley can be formed by necking a molded strap. Pulling a molded strap beyond its yield point can reduce the cross-section of the strap permanently and make it more flexible when it elongates. Heat can be used in the necking process to facilitate elongation and reduction in the cross-sectional area. Alternative mechanisms shown in FIGS. 16A-16B can be used for locking strap materials such as suture and softer plastic once desired closure is achieved. FIG. 16A shows a locking mechanism comprising a slot for sliding 1610 and an anchoring frame 1620. FIG. 16B shows a locking mechanism comprising a locking tooth 1630. FIG. 16C shows a locking mechanism comprising a slot for sliding 1640 and an anchoring frame 1650. FIG. 16D shows a locking mechanism comprising a cylindrical tube 1660 and locking teeth 1670.

Figure 17:
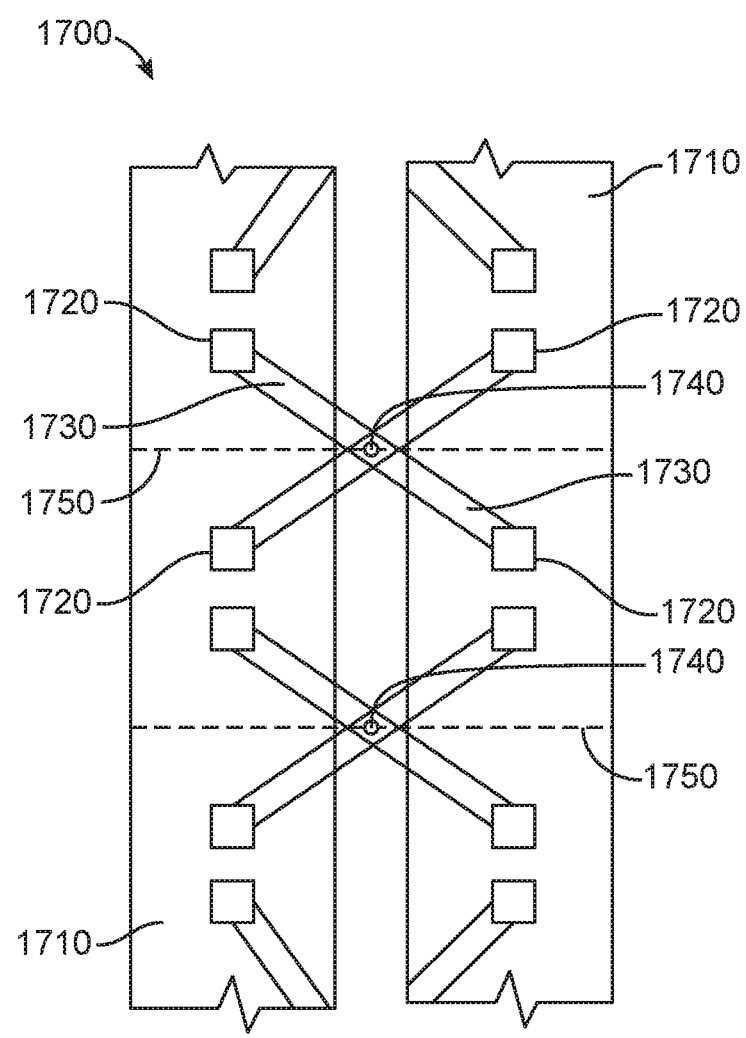
FIG. 17 shows a hinging mechanism for incision closure appliances in accordance with the principles of the present invention.

The additional closure force across the incision when the knee flexes may be achieved by using a hinging mechanism 1700 as shown in FIG. 17. As shown in FIG. 17, the four points on either side of the incision (two anchor points 1720 on each side or base panel 1710 of the incision closure appliance) may be connected with non-stretching arms 1730 in the shape of an X, with hinging provided at the intersection 1740. As the knee flexes and the distance between two points on the same side of the incision increases, the distance between the segments on either side of the incision may decrease, resulting in additional closure force. As shown in FIG. 17, the base panels 1710 may also be provided with a plurality of perforations 1750 to facilitate axial stretching to the base panel 1710 or its separation into discrete segments upon axial stretching.

Figure 18:
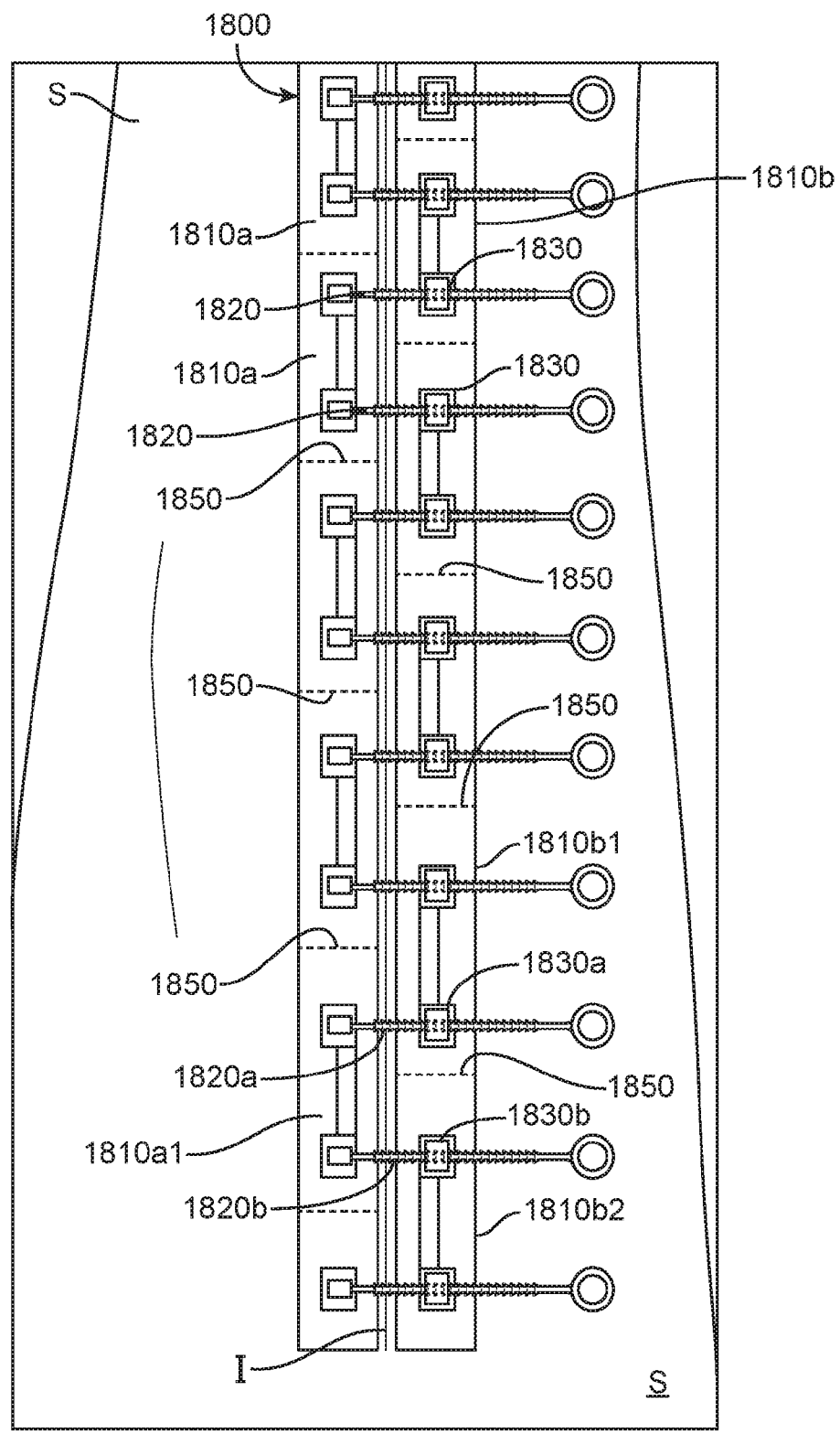
FIG. 18 is a top view of an incision closure appliance similar to that of FIG. 14A and placed on the knee of a subject according to the present invention.

As shown in FIG. 18, the straps and locks of an incision closure appliance 1800 according to many embodiments can be configured to form an S-shaped or serpentine connection or arrangement across the entire length of the incision I on the skin S of a knee. The incision closure appliance 1800 may be similar in many respects to the incision closure appliance 1400 described above. The segments 1810*a*, 1810*b* of the device 1800 are connected to each other by connecting each segment 1810*a* on one side of the incision I with two adjacent segments 1810*b* on the opposite side of the incision. This may be achieved by mounting a pair of straps 1820 in each segment 1810*a* and a pair of locks 1830 on the corresponding segments 1810*b* on the other side. Each pair of locks 1830 and straps 1820 may be connected with each other. During closure of the wound or incision I, one of the straps 1820 (e.g., strap 1820*a*) of a base panel segment 1810*a* (e.g., 1810*a* 1) may be connected with a lock 1830 (e.g., 1830*a*) on a segment 1810*b* (e.g., segment 1810*b* 1) on the other side of the incision I and the second strap 1820 (e.g., strap 1820*b*) may connected with a lock 1830 (e.g., 1830*b*) in the segment 1810 (e.g., segment 1810*b* 2) on the opposite side of the incision I adjacent to segment 1810*b* (e.g., 1810*b* 1) in which the previous paired strap 1820 (e.g., strap 1820*a*) was connected. The aforementioned connections form a single loop of the S-shaped or serpentine arrangement of base panel segments 1810, straps 1820, and locks 1830. Perforation lines 1850 may separate axially adjacent base panel segments 1810*a* and 1810*b*. The perforation lines 1850 on one side (e.g., with base panel segments 1810*a*) may be staggered with the perforation lines 1850 on the other side (e.g., with base panel segments 1810*b*). Similar to FIG. 15A, in preferred embodiments, the adhesive panel on each side of the incision may be 12 mm wide, and the perforations within a given panel may be spaced about 18 mm apart.

Figure 19:
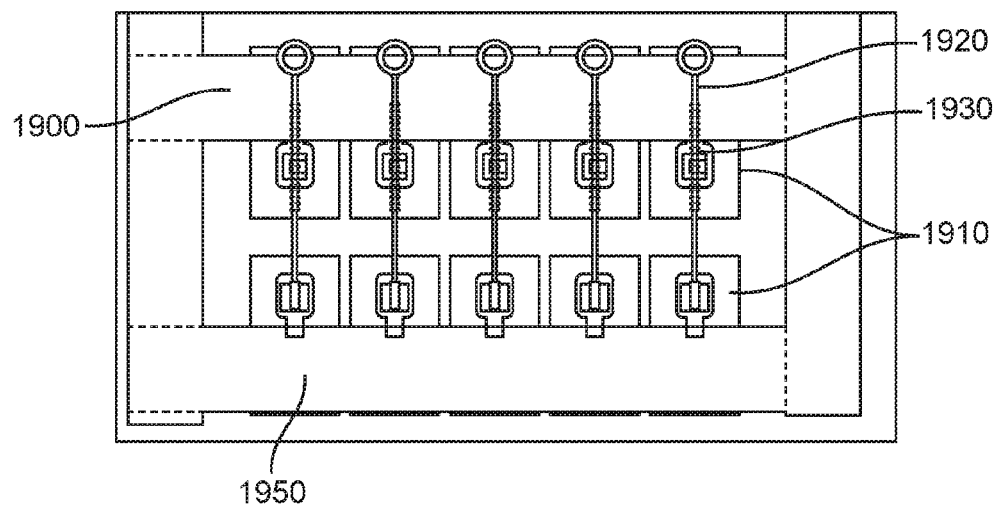
FIG. 19 shows an incision closure appliance comprising individual pairs of base panel segments according to the present invention.

Incision closure appliances or devices as described herein may be applied in many ways. FIG. 19 shows an example incision closure appliance 190 according to some embodiments. Here, individual base pair segments 1910 arranged in pairs may be provided on individual carrier/release liners. Each base panel segment 1910 pair comprises a strap 1920 and lock 1930 that may be independently aligned with the incision and adhered to skin adjacent to each other. Individual segments 1910 may be held together in relation to one another with a release liner and outer carrier tape 1950. The release liner 1950 may be removed to expose the adhesive, but the entire device 1900 or grouped portions of the device 1900 may be linked with the outer carrier tape. Upon application to the skin, the carrier tape 1950 may be removed, leaving adhesive segments 1910 which are aligned with one another but can move independently.

Perforated segments of base panel upper layers, typically comprising polyurethane, may be held together with a continuous layer of the adhesive bottom layer, typically comprising a hydrocolloid adhesive, to allow laying down on the skin in one continuous motion. The incision closure appliances 1400, 1500, and 1800 of FIGS. 14A-14B, 15A-15C, and 18, respectively, may be provided with such a continuous adhesive bottom layer.

The base assembly or base panels of the incision closure appliances described herein preferably may be covered with a flexible adhesive film material at the end of a wound or incision closure. This film area preferably may be larger than the base incision closure panel elements such that it overlaps the elements onto the skin. The film may help prevent migration of the anchors and may prevent any accidental movements of the anchors and locking mechanisms. The cover film may be made from stretchable materials like rubber, latex, polyurethane, silicone or thermoplastic elastomer, etc. In preferred embodiments, a thin cover (e.g., laminate of 0.001" urethane and 0.002" thick acrylic adhesive), will have a greater compliance than the composite structure of the base panel elements. As a result, the cover may offer some strain relief between the exposed skin and the base segments. The cover may also be transparent to allow visual inspection of the incision. The cover may completely seal across the incision (e.g., as a barrier to infection) or there may be openings in the cover that are aligned with the incision line to allow passage of any exudates from the wound. The cover may also serve to improve the apposition of the incision edges by bridging the base panels and adhering to the skin edges between the base strips. The cover may also be constructed with additional reinforcing elements that improve the tensile strength between the base panel elements but allow for compliance along the incision length. A preferred embodiment may comprise a series of polyethylene adhesive tape strips applied to the cover.

While the user may apply the cover after the base assembly and panels are placed on the skin, it is also conceived that the cover material may be supplied as a "skirt" extending around the outer perimeter of the base segments. Thus, alignment of the cover materials relative to the base may not be dependent on the user placement. These same cover materials may provide the effects of preventing exposure of the hydrocolloid adhesive to patient clothing, limitation of migration of the hydrocolloid or other adhesive lower layer, providing strain relief for the tension on the base segments, etc.

In many embodiments, a hydrocolloid adhesive is used for tensioning skin for incision closure. The hydrocolloid may be prevented from creep by one or more of (1) using a laminate on the surface to limit creep or (2) applying an adhesive cover across the skin and the hydrocolloid adhesive to prevent creep and to provide strain relief to the skin to prevent skin damage.

In many embodiments, a cover as used with the base assembly may include one or more of perforations or openings to allow removal of wound exudate (as well as any applied bandages/absorbant material) without removal of the adhered base assembly.

In many embodiments, the cover comprises a composite of flexible urethane and reinforced strips. The composite construction may provide strength across the incision as well as provide for compliance along the incision length.

In many embodiments, the cover in combination with the base assembly aligns the skin incision edges or significantly prevents subsequent misalignment of the skin edges, in both the axial and lateral directions.

In many embodiments, cover liner configurations are provided such that part of the cover can be applied to the skin first, which then aids in the removal of other liners and thus may help control the thin materials so they lay out evenly with minimal wrinkling.

In many embodiments, the removal of a first liner may allow visualization during placement and may prevent the remainder of the device from sticking to the user.

Figure 20A:
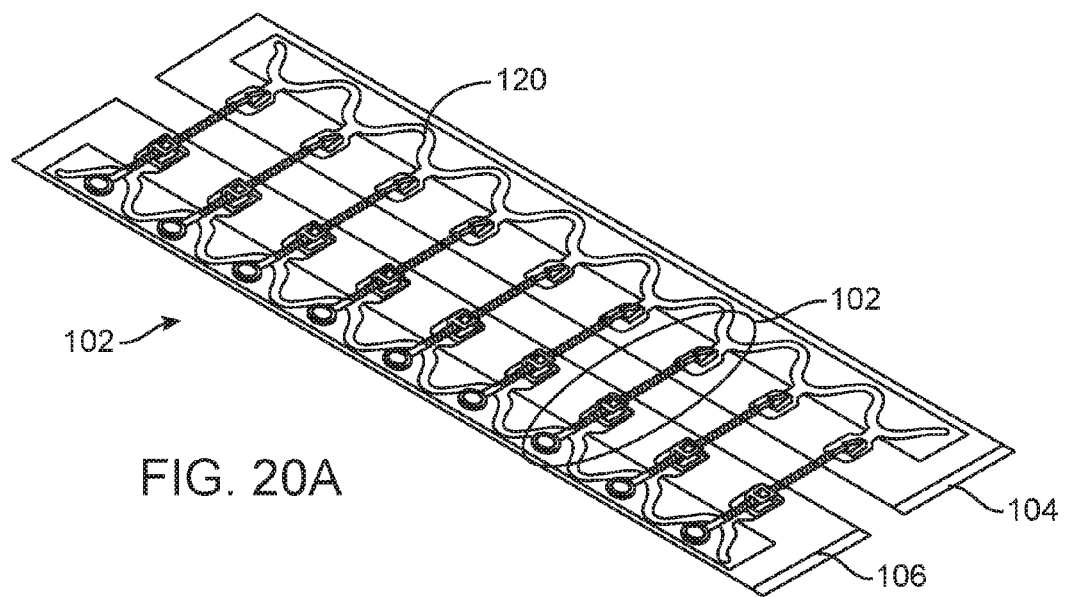
FIG. 20A shows a perspective view of the incision closure appliance similar to that of FIGS. 9 and 10 in accordance with the principles of the present invention.
Figure 20B:
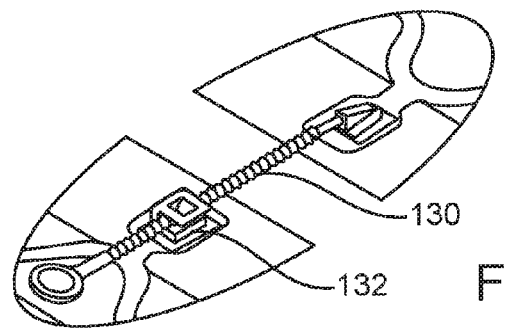
FIG. 20B shows a magnified view of the lateral tie assembly of the incision closure appliance of FIG. 20A.

Referring back to FIGS. 9 and 10, two adhesive panels 104, 106 are in many preferred embodiments applied to either side of a surgical incision (either before or after the incision is made). A closure mechanism may be mounted on top of the adhesive panels 104, 106 and may be preferably attached to a component 120 which helps to distribute the closure forces between attachment points of the closure mechanism. As shown in FIGS. 9 and 10 as well as FIGS. 20A and 20B, this closure mechanism may comprise a strap 130 and a lock 132. The strap 130 may comprise an elongated component with engagement teeth. The lock 132 may comprise a feature for capturing the engagement teeth of the strap 130. The strap 130 may be tightened in the lock 132 to pull the adhesive panels 104, 106 (and thus the incision edges) together. The user may disengage and re-engage the strap 130 in the lock 132 as necessary to properly adjust the amount of skin closure. Together, the incision closure appliance illustrated in FIG. 20A may be described as the base or base assembly 102.

The skin adhesive used for each panel 104, 106 may preferably comprise a hydrocolloid adhesive. Alternatively or in combination, the skin adhesive may comprise one of many acrylic formulations known in the art. Hydrocolloid adhesives may have the benefit of being very tacky and able to absorb moisture and shedding skin cells. Thus, hydrocolloid adhesives may be particularly suited for long-term wear applications (e.g., up to 14 days). In at least some instances, the hydrocolloid structure may be soft, however, and may be prone to creep under tension unless reinforced in some manner such as by covering the hydrocolloid adhesive layer with stiffer base panels 102, 104 or other covering structures disclosed herein.

Figure 21:
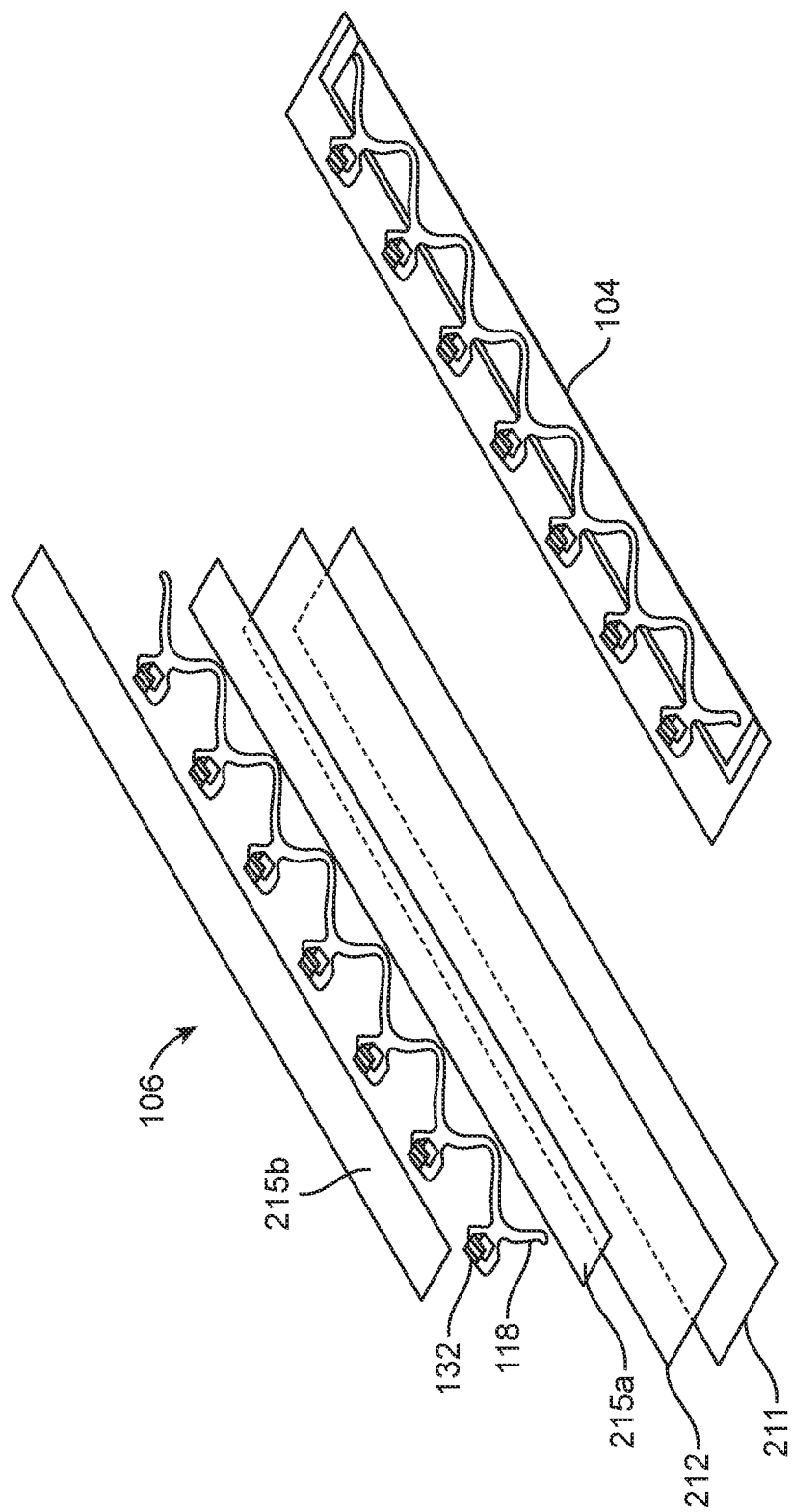
FIG. 21 shows an exploded view of a portion of the incision closure appliance of FIG. 21.

Accordingly, a further aspect of the present invention also provides various means of reinforcing and protecting the adhesive layer in the base assemblies of the incision closure appliances described herein as well as additional means of holding the skin edges together, particularly in the axial direction. In at least some cases, the hydrocolloid adhesive alone has very low tensile strength and may require a means of reinforcement to prevent it from tearing or creeping during use. As illustrated in FIG. 21, the adhesive layer 211 used in the base panels 104, 106 may be laminated with a thin layer of a compliant plastic or polymer 212, such as urethane, preferably 0.001 inch thick, with a potential range up to 0.010" thick, that may helps to maintain its structure during clinical use. The adhesive layer itself may nominally be 0.010 inch thick, but may range between 0.005 inch and 0.020 inch thick. Because tensioning elements comprising straps 130 or locks 132 attached to a load distribution component 118 may be mounted to the top of the adhesive structure 211, the possibility exists that the material could creep over time. The laminate 212 as well as any other adhesive laminates 215a, 215b between the adhesive layer 211 and the load distribution component 118 may help provide the structure to prevent creep of the adhesive layer.

Figure 22A:
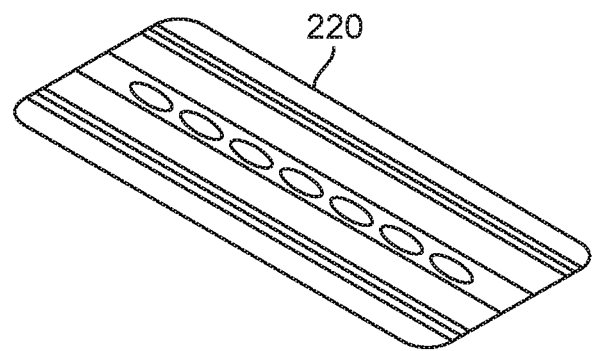
FIG. 22A shows a perspective view of a cover for the incision closure appliances disclosed herein in accordance with the principles of the present invention.
Figure 22B:
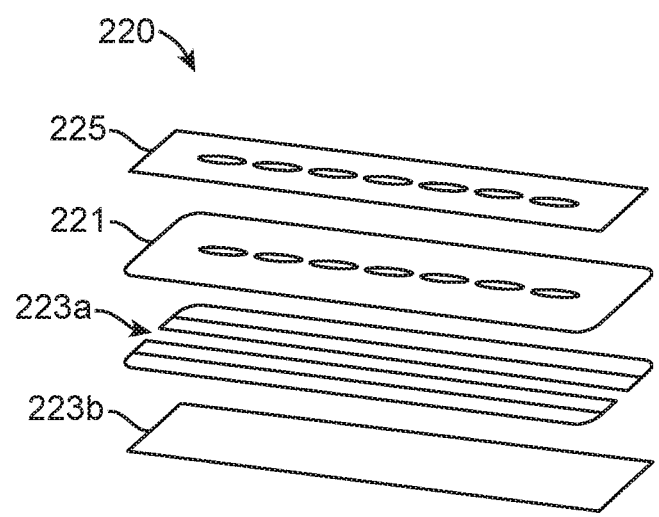
FIG. 22B shows an exploded view of the cover of FIG. 22A.

To further prevent migration of the adhesive panel 211, a cover 220 may also be applied over the panels 104, 106 as shown in FIG. 22A. As shown in FIG. 22B, the cover 220 may comprise a thin, adhesive coated compliant elastomer 221. In many embodiments, the cover 220 further comprises a thin urethane layer (preferably 0.001 inch thick) coated with a skin adhesive, such as an acrylic adhesive (preferably 0.002 inch thick), which may be provided on one or more release liners 223a, 223b. The cover may further comprise reinforcing features 225.

Figure 23A:
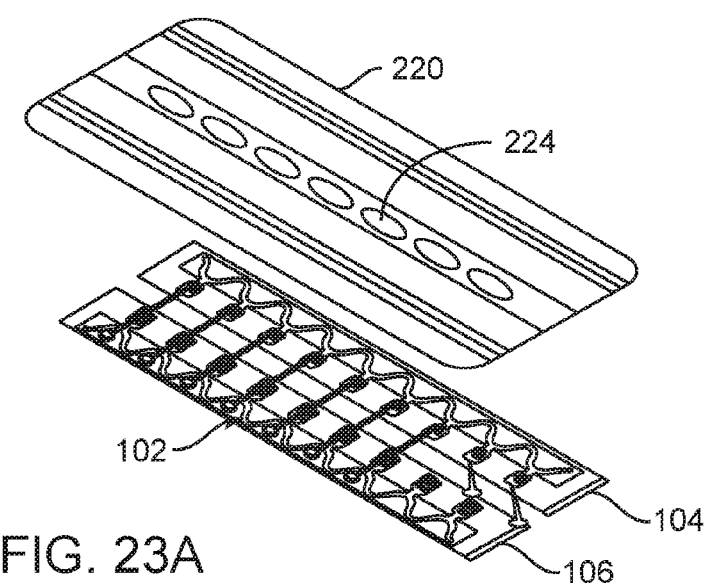
FIG. 23A shows an exploded view of an incision closure appliance assembly comprising the incision closure appliance of FIG. 21 and the cover of FIG. 22A in accordance with the principles of the present invention.
Figure 23B:
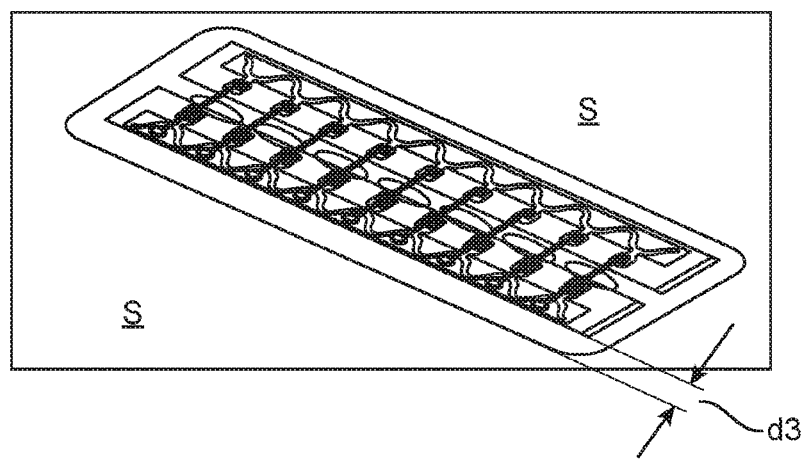
FIG. 23B shows a perspective view of the incision closure appliance assembly of FIG. 23A adhered onto the skin of a patient.

As shown in FIGS. 23A and 23B, the cover 220 may be constructed such that it may extend beyond the base panels 104, 106, thereby bridging a distance, d3, between the skin S and the panels 104, 106. A typical minimum necessary distance, d3, may be 8 mm but could range 2-15 mm. Besides helping prevent creep of the adhesive layer of the base panels 104, 106, the urethane skin adhesive of the cover 220 may also help to strain relieve the tension applied to the base panels 104, 106 from movement of the surrounding skin S. This may serve to prevent skin damage (e.g., from erosion or blistering) at the base panel 104, 106 edges. It should be noted, however, that the compliant nature of the hydrocolloid offers local protection from blistering by itself being able to move with the skin S and thus resist damage to the skin S. In many embodiments, even with stiffer structures mounted to the outer surface of the adhesive layers, the compliance within the nominal 0.010" thickness of the adhesive layers down to the skin surface may provide resistance to skin damage.

Figure 23C:
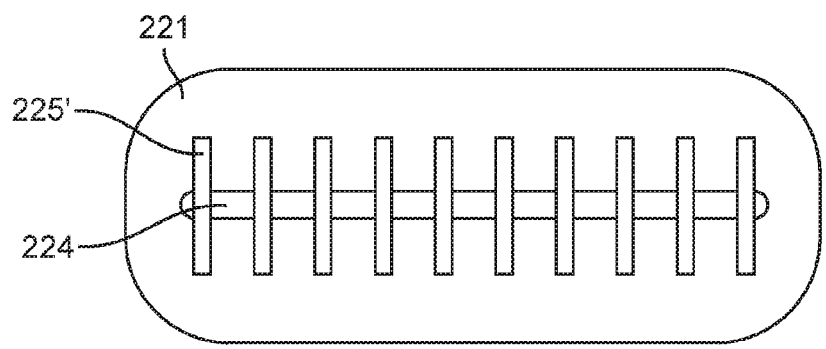
FIG. 23C shows a top view of the elastomeric reinforcement layer of the cover of FIG. 22A.

Besides stabilizing and strain relieving the base panel structures, the cover 220 may serve other purposes. By covering the location where a strap 130 would engages a lock 132, the cover 220 may prevent the patient from tampering with the locks 132 to the point where the straps 130 could be disengaged. As shown in FIGS. 23A-23C, the cover 220 may be fitted with openings 224, 224' along the length of the region overlapping an incision, such that externally applied gauze may absorb wound exudate. In other embodiments, the cover 220 may not have openings in order to protect the wound from sources of infection. The cover 220 itself may have reinforcing features 225, 225' to provide the base 102 with additional resistance to the incision opening, particularly in regions between the straps 130. FIG. 23C shows a particular embodiment where the reinforcing features 225' could be rectangular strips of adhesive tape. The tape 225' may preferably be stiffer perpendicular to the skin incision than the surrounding compliant urethane layer 221. The tape 225' may be constructed from any combination of adhesive coated woven fabric, polymer fibers, polyethylene, polypropylene, nylon, PET, hydrocolloid, or other materials known in the art. The reinforcing features 225' may also add "body" or stiffness to the cover 220 to aid in its placement. The urethane layer 210 may be constructed of such materials to give it a bi-directional stretch.

The spacing of the reinforcing features 225, 225' may be important to ensure the longitudinal (parallel to the incision line) compliance of the cover 220 (e.g., due to the compliant thin urethane). This may serve to improve patient comfort and the resistance to skin damage by allowing the cover 220 and the underlying base assembly 102 to move with motions of the body. This effect may be from the cover 220 alone or as a composite effect with features on the base assembly 102 which may allow longitudinal compliance. The reinforcements 225, 225' may also be of a uniform construct, but perforated, slit, or otherwise mechanically interrupted to allow stretch and/or controlled tearing with body motion. The thin urethane layer(s) of the cover 220 may also be mechanically interrupted to the same effect. In at least some cases, the reinforcing features 225, 225' of the cover 220 may not extend the entire width (perpendicular to incision) of the cover 220. This limited covering width may help ensure strain relief to the body motion away from the base assembly 102 perpendicular to the incision I. In preferred embodiments, the region of the cover 220 reinforced by the reinforcement members 225, 225' extends 10 mm in each direction away from the incision edge, but this may range from 2-50 mm.

Figure 24A:
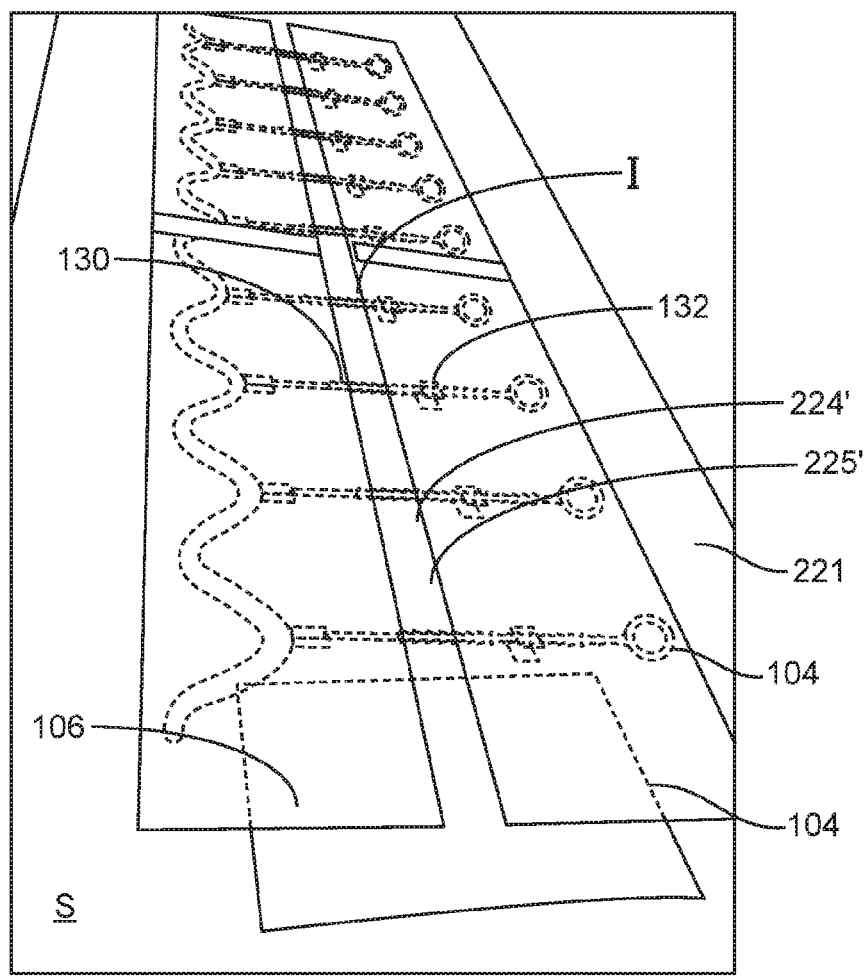
FIG. 24A shows a perspective view of the incision closure appliance assembly of FIG. 23A adhered onto the skin of a patient in accordance with the principles of the present invention.
Figure 24B:
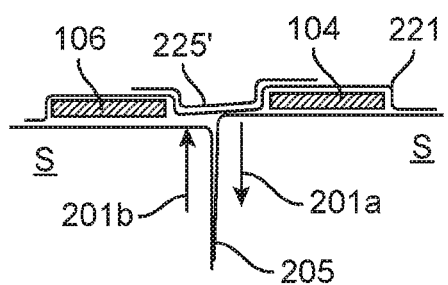
FIG. 24B shows a sectional schematic diagram of the incision closure appliance of FIG. 23A adhered onto the skin of a patient in accordance with the principles of the present invention.

Another feature of the cover 220 may be to be able to add control to the incision edge, particularly between the tensioning elements 130, 132 of the base assembly. As illustrated in FIG. 24A, the tensioning elements 130, 132 combined with the base panels 104, 106 may serve to approximate the incision edges 205 together. Once the skin S is approximated, it may be important that the skin edges be aligned vertically (perpendicular to the skin surface). Vertical misalignment may lead to slower healing and visible "step-off", or ledge, in the incision that may result in poor scar cosmesis. By having portions of the cover 220 adhere to each edge of the base panels 104, 106 along the incision, each edge may held under tension in vertical alignment as shown by arrows 201*a*, 201*b*. Adhesive on portions of the cover 220 crossing the incision I may also adhere directly to the skin S at the incision edge, further shortening the distance between the adhered incision edges and further enhancing vertical skin alignment. In preferred embodiments, the portions of the cover 220 crossing the incision I are rectangular strips 225' of adhesive tape as shown in FIG. 23C. The width of each strip 225' and the axial gap between the strips 225' may be optimized for incision edge control, incision visibility, and the escape of wound exudate. A preferred embodiment may comprise a strip 12 mm wide and spaced 6 mm apart, with the straps located between each strip. Other widths and spacing are also contemplated. By not bridging/tenting over each strap 130, the strip 225 may lay flatter against the skin S for better adhesion and edge control.

In some embodiments, the reinforcing features 225, 225' may be constructed to limit the amount of bending at the incision site. The reinforcing features 225, 225' in these embodiments may be stiffer than the skin S, and preferably stiffer than the surrounding elements of the base panels 104, 106. In this way, and bending or compression of the skin S through normal patient motion would be isolated, or the propagation limited, around the incision site. While this motion isolation or limitation would help strengthen the incision site in tension, a greater benefit may be to prevent the incision edges from significantly or unevenly inverting, everting, or shifting in a direction perpendicular to the skin surface. Reinforcing materials discussed above may be used, with the thickness tailored to create the desired stiffness. Preferably, the composite of the base assembly 102 and cover 220 may be constructed to create a smooth transition in stiffness and compliance from the surrounding skin to the isolated incision site.

Figure 25A:
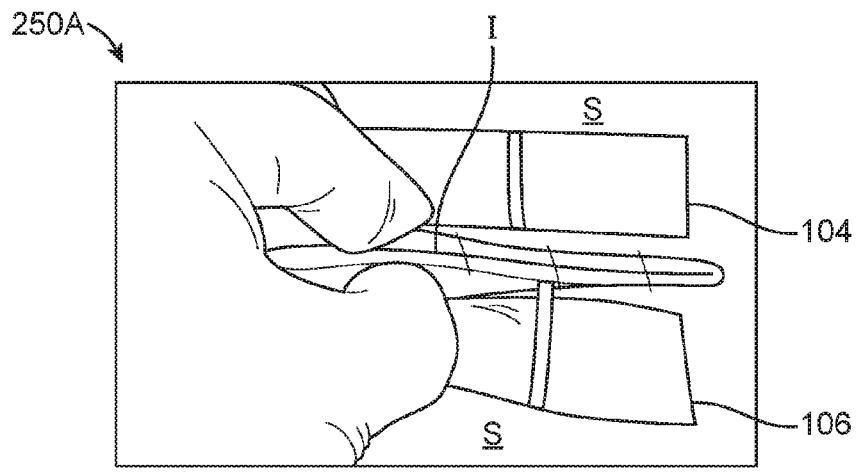
FIGS. 25A-25C illustrate a method of applying the incision closure appliance assembly of FIG. 23A on the skin of a patient in accordance with the principles of the present invention.
Figure 25B:
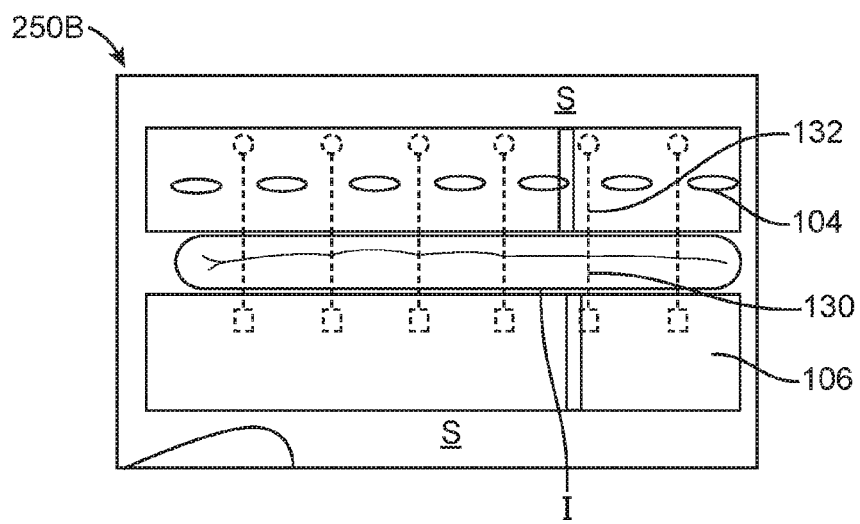
Figure 25C:
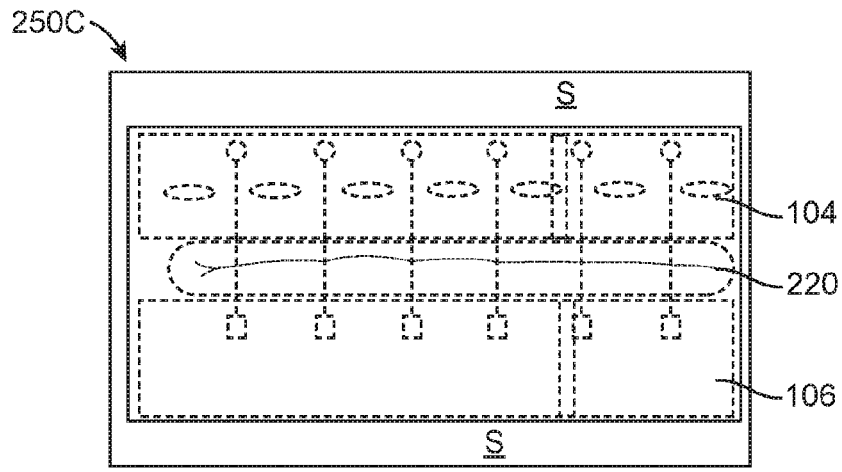

In particular methods of use, after initial closure of the incision using the base assembly 102 to approximate the skin edges, the base panels 104, 106 may be pushed together further to "pooch" the closed incision I upward to slightly evert the edges and/or compress the skin S around the incision edges to relieve tension. FIGS. 25A-25C illustrate an embodiment of this method in an in-vivo tissue model. FIG. 25A shows a step 250A in which the base panels 104, 106 are adhered to the skin S adjacent an incision I and are pushed together to "pooch" the closed incision I upward. The base panels 104, 106 may be then pulled together further to hold the tissue in this orientation. These methods may be enhanced by positioning the base panels 104, 106 away from the incision edge by 5-10 mm. In a step 250B shown by FIG. 25B, the base panels 104, 106 may be locked in place relative to one another with the straps 130 and the locks 132. In a step 250C shown by FIG. 25C, the cover 220 may then be applied to lock in the relative location of the base panels 104, 106 and "pooched" incision I. The incision I could be further reinforced with the reinforcing elements 225, 225' discussed above.

A given cover 220 may in many embodiments be fitted with release liners to aid in user handling of the cover 220 before and during application to the patient. As shown in FIGS. 22A and 22B, the cover 220 may have release liners 223*a*, 223*b* applied in a three-part configuration. The user may first remove a longitudinal center liner 223*b* to apply the center exposed adhesive to the base assembly 102 and skin incision region. Removal of this liner 223*b* first, in combination with visualization through the clear plastic and/or openings in the center of the base 220, may allow the user to see the base assembly 102 underneath such that the cover 220 can be properly aligned with the base assembly 102 as the cover 220 is applied. This may also help provide regions of the cover 220 that do not stick to the user until the cover 220 is initially secured to the base assembly 102 and/or the skin S. Next, the side release liners 223*a* may be removed in a direction perpendicular to the incision I. The liners 223*a* hold and tension the very thin urethane to keep it from substantially wrinkling as it is applied to the skin S. Also, by sticking the center of the cover 220 to the base assembly 102 and/or the skin S first, the cover 220 may be held in place such that sufficient tension and control may be applied to the side release liners 223*a* for smooth application of the remainder of thin adhesive coated cover 220 to the patient. Alternatively or in combination, the liners may be constructed such that the first liner is removed to expose a narrow strip over the full width of the cover 220 (perpendicular to the incision I) to allow initial placement on the base assembly 102 and/or skin S, followed by removal of one or two additional liners in a direction parallel to the incision I. The first liner may be in the middle of the length, on either end, or somewhere in between. If not on the end, two additional liners may be required, each removed in a direction from the location of the first liner outward along the length of the device. If the first liner was on one end, a second single liner may be removed from the location of the first liner out toward the end of the device.

Another release liner configuration may be to have a single liner which could be completely removed from the bottom of the cover 220 before application. This type of liner may require an outer film, or casting sheet, be lightly adhered to the outer surface of the cover 220 to help the thin urethane hold its shape and provide the user with locations at the sides and/or ends which do not have adhesive and thus would not stick to the user's hands during application. The outer film could be over the entire outer surface or just a particular width surrounding the perimeter of the cover 220. The film and/or the release liner could also have an area extending beyond that of the thin urethane in the cover 220. Once the cover adhesive is attached to the base assembly 102 or skin S, the casting sheet may be easily removed from the outside of the cover 220.

As described herein, flexible wound dressings and wound or incision closure devices or appliances are typically flexible and stretchable to follow the contour of curved parts of the body (e.g., arm, longer incisions that are curvilinear, etc.) or the areas that undergo stretching (e.g., knee). To assist the draping of such devices, a backing material may be used which assists in maintaining the dressing shape during the application. Such temporary backing material described herein may have a number of advantages. The backing material may be clear to enable the visual of the wound. The material may be non-stretchable to prevent elongation of the dressing or closure device or appliance during application. The backing may be easily removable after the application of the wound dressing or closure device or appliance so as to not affect the adhesion of the actual dressing on the wound site. The backing material may also assist in the handling of the dressing during manufacturing process. In many embodiments, the backing material may couple to a dressing or closure device with peel-off release liners on the adhesive side of the dressing to enable easy and reliable removal of the backing material.

Figure 26A:
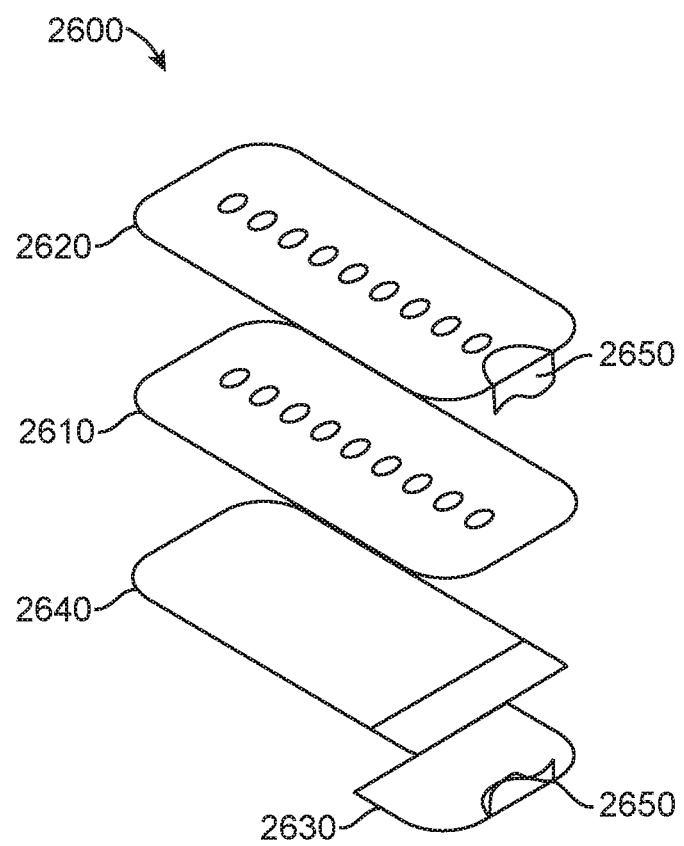
FIGS. 26A-26E illustrate embodiments of a cover for wound dressings and incision closure appliances in accordance with the principles of the present invention.

Referring now to FIG. 26A, a wound dressing cover 2600 may comprise a flexible sheet 2610 made of a flexible material like rubber, urethane, silicone, etc. The flexible material 2610 may laminated on a relatively stiffer material in the form of a casting sheet or carrier layer 2620. The casting sheet 2620 prevents the flexible material 2610 from rolling onto itself and becoming unusable. The flexible sheet 2610 may have an adhesive on one side (e.g., the bottom side) and a relatively rigid (stiff) carrier layer or casting sheet 2620 on the other side. The adhesive side is protected by two liners 2630, 2640 that can be sequentially removed to expose the adhesive in a controlled manner. To apply the dressing 2600 on the wound or incision, a small strip of adhesive is exposed by removing one of the release liners, usually the smaller release liner 2630. This release liner 2630 may be attached to the casting sheet 2620 using a tape 2650. The exposed part of the flexible sheet 2610 may then be adhered at one end of the wound or incision. The flexible cover 2600 then follows the contour of the wound or incision and the curvature on the body as the second release liner 2640 is slowly removed to expose the adhesive sequentially.

The first release liner 2630 which is typically still attached to the casting sheet 2620 with the tape 2650 may then be used to lift the casting sheet 2620 from the flexible dressing 2610.

A manufacturing process for the wound dressing cover 2600 and associated liners 2630, 2640 may be to use a single die to cut a common profile (perimeter) of the laminate of the release liners 2630, 2640, the flexible dressing (with adhesive) 2610, and the casting sheet 2620. Upon removal of the liners 2630, 2640 and application of the dressing sheet 2610 to the skin, the casting sheet 2620 may remain on the dressing sheet 2610. Removal of the casting sheet 2620 may require initiation by delaminating and peeling back an edge of the casting sheet 2620 from the dressing sheet 2610. Once initiated, the continued peel and removal of the casting sheet 2620 may be straightforward. Initiation and lift of the edge of the casting sheet 2620 may not always be intuitive and may requires a free edge connected to the casting sheet 2620 to help identify the lift point and begin the peel. The tape 2650 may be used to bridge the casting sheet 2620 to the release liner 2630 and may provide an easily identifiable tab which can be used to initiate the peel.

Alternative configurations of the casting sheet 2620 may be used to initiate the peel of the casting sheet 2620 as shown in FIGS. 26B-26E.

Figure 26B:
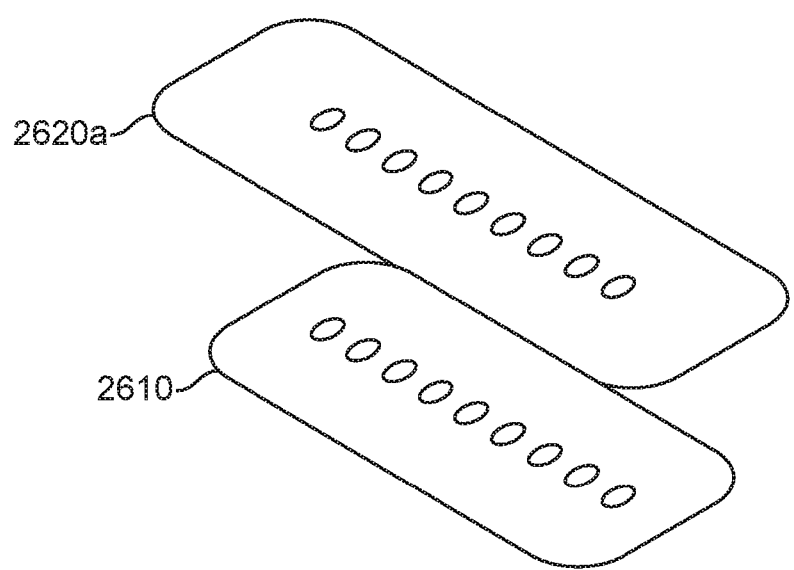

As shown in FIG. 26B, the casting sheet die may be cut such that the casting sheet 2620a extends axially beyond the flexible dressing sheet 2610 (e.g., the liners 2630, 2640 and urethane material of the flexible dressing sheet 2610 may be "kiss cut" to the surface of the casting sheet 2620a).

Figure 26C:
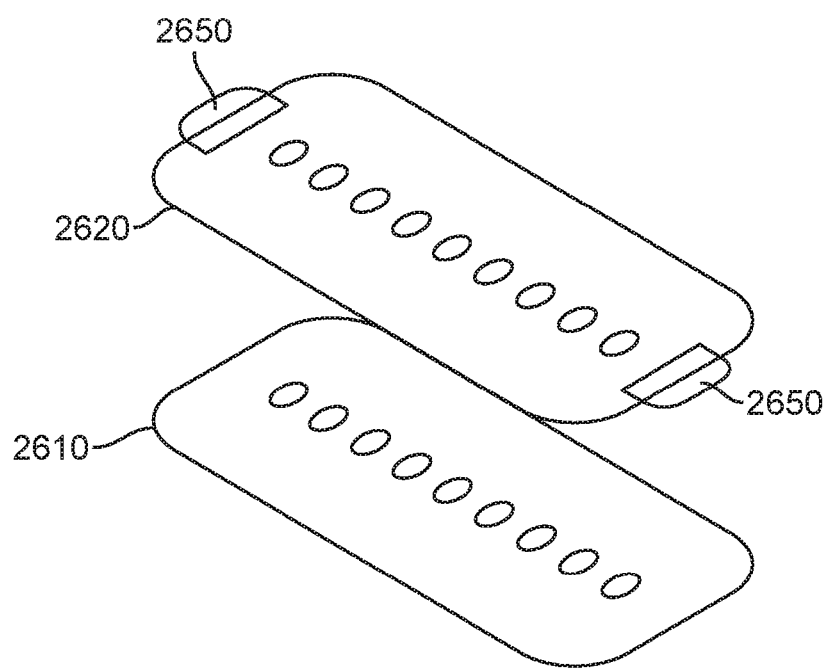

As shown in FIG. 26C, the casting sheet 2620 may have tape 2650 applied to either one or both axial sides to extend beyond the casting sheet. The tape 2650 may not necessarily be attached to the release liner 2630.

Figure 26D:
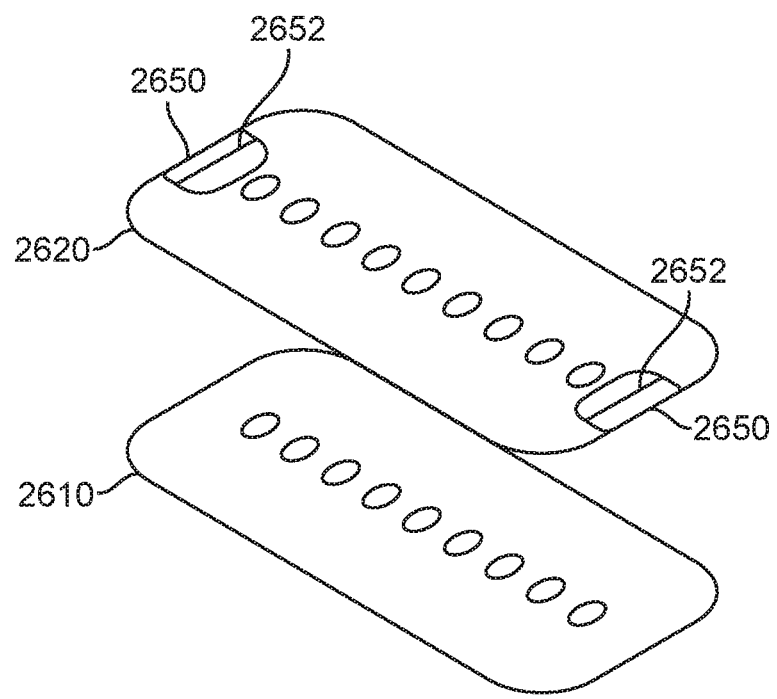

As shown in FIG. 26D, casting sheet tape 2650 may be attached at or near the axial edge(s) of the casting sheet 2620 and also extends inside the profile of the casting sheet 2620, with a loose non-adherent edge 2652 for the user to grasp.

Figure 26E:
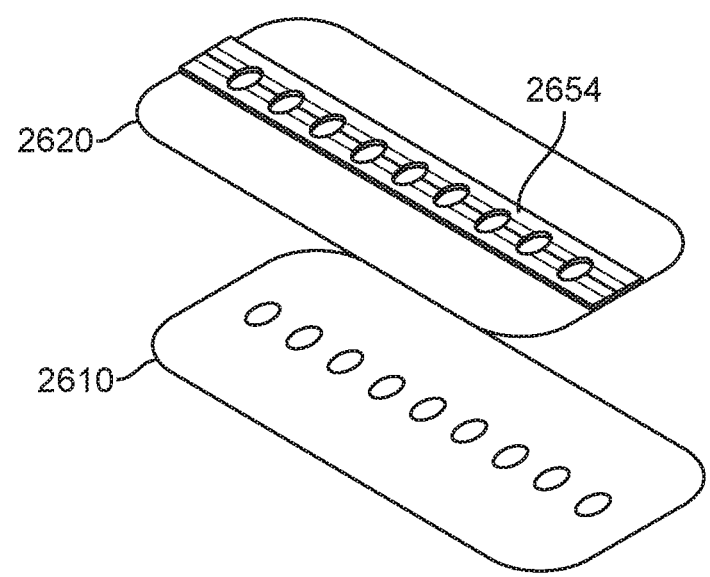

As shown in FIG. 26E, the casting sheet die may be cut (e.g., kiss cut such that the casting sheet 2620 is not cut into the flexible dressing sheet 2610) from one axial edge to a partial or full-length distance to another axial edge of the casting sheet 2620. The cut casting sheet 2620 may be separated with a "pinch" by the user to create an edge to grasp. The interior die cut edge may also have a tape or similar tab 2654 applied to one or both of the interior edges to grasp and peel as shown in FIG. 26E.

In many embodiments, the casting sheet 2620, 2620a and/or tape 2650, 2652, 2654 may be of a different color or have markings to distinguish from the flexible dressing sheet 2610 and release liners 2630, 2640.

One or more of the components of the incision closure appliances or incision closure appliance assemblies disclosed herein, including one or more of the various base assemblies, base panels, force distribution structures, axial supports, lateral supports, closure components, tie assemblies, straps, locks, adhesive layers, adhesive layers, covers, cover structures, drapes, etc., may be comprised of, be coated with, or otherwise incorporate one or more of an antifungal, antibacterial, antimicrobial, antiseptic, or medicated material. For example, such materials may be incorporated into the hydrocolloid adhesive layer, as another layer or coating between the skin and the adhesive layer (covering at least a portion of the adhesive layer), incorporated into the base assembly cover or at least its adhesive layer, etc. One or more wells, grooves, openings, pores, or similar structures may be provided on the device or apparatus components to facilitate such incorporation. In many embodiments, such materials may comprise one or more of silver, iodide, zinc, chlorine, copper, or natural materials such as tea tree oil as the active agent. Examples of such antifungal, antibacterial, antimicrobial, antiseptic, or medicated materials include, but are not limited to, the Acticoat™ family of materials available from Smith & Nephew plc of the U.K., the Acticoat® Moisture Control family of materials available from Smith & Nephew plc of the U.K., the Contreet® Foam family of materials available from Coloplast A/S of Denmark, the UrgoCell® Silver family of materials available from Urgo Limited of the U.K. (a subsidiary of Laboratoires URGO of France), the Contreet® Hydrocolloid family of materials available from Smith & Nephew plc of the U.K., the Aquacel® Ag family of materials available from ConvaTec Inc. of Skillman, N.J., the Silvercel® family of materials available from Kinetic Concepts, Inc. of San Antonio, Tex., Actisorb® Silver 220 available from Kinetic Concepts, Inc. of San Antonio, Tex., the Urgotul® SSD family of materials available from Urgo Limited of the U.K. (a subsidiary of Laboratoires URGO of France), the Inadine® family of materials available from Kinetic Concepts, Inc. of San Antonio, Tex., the Iodoflex® family of materials available from Smith & Nephew plc of the U.K., the Sorbsan Silver™ family of materials available from Aspen Medical Europe Ltd. of the U.K., the Polymem Silver® family of materials available from Ferris Mfg. Corp. of Burr Ridge, Ill., the Promogram™ family of materials available from Kinetic Concepts, Inc. of San Antonio, Tex., the Promogram Prisma™ family of materials available from Kinetic Concepts, Inc. of San Antonio, Tex., and the Arglaes® family of materials available from Medline Industries, Inc. of Mundelein, Ill. Components of the closure devices described in commonly owned U.S. Pat. Nos. 8,313,508, 8,323,313, and 8,439,945; U.S. Patent Publication No. 2013/0066365; and PCT application nos. US 2010/000430, US 2011/139912, US 2011/40213, US 2011/34649, and US 2013/067024 may also be comprised of, be coated with, or otherwise incorporate one or more of an antifungal, antibacterial, antimicrobial, antiseptic, or medicated material, including but not limited to one or more of the materials listed above.

In many embodiments, topical medicinal agents are incorporated directly into the wound closure appliances described herein. Because a wound closure device is often applied in close proximity to a wound or incision in need of medicinal protection, the incorporation of such medicines directly into the closure device may be beneficial. In wounds at risk of infection, incorporation of anti-microbial agents may be beneficial, for example. Anti-microbial agents may include antibiotic medicines as well as antiseptic metal ions and associated compounds which may include silver, iodine, copper, and chlorine, or natural materials such as tea tree oil. In wounds prone to fungus, medicinal agents such as zinc may be warranted, for example. Combinations of any of these agents may also be of benefit and thus may be incorporated into wound closure appliances.

Topical medicinal agents may be incorporated into the closure devices in a way to give the closure devices the ability to wick exudate away from the wound (e.g., to direct unwanted organisms away from the wound and/or prevent skin maceration), while keeping the wound sufficiently hydrated for improved healing.

Figure 27A:
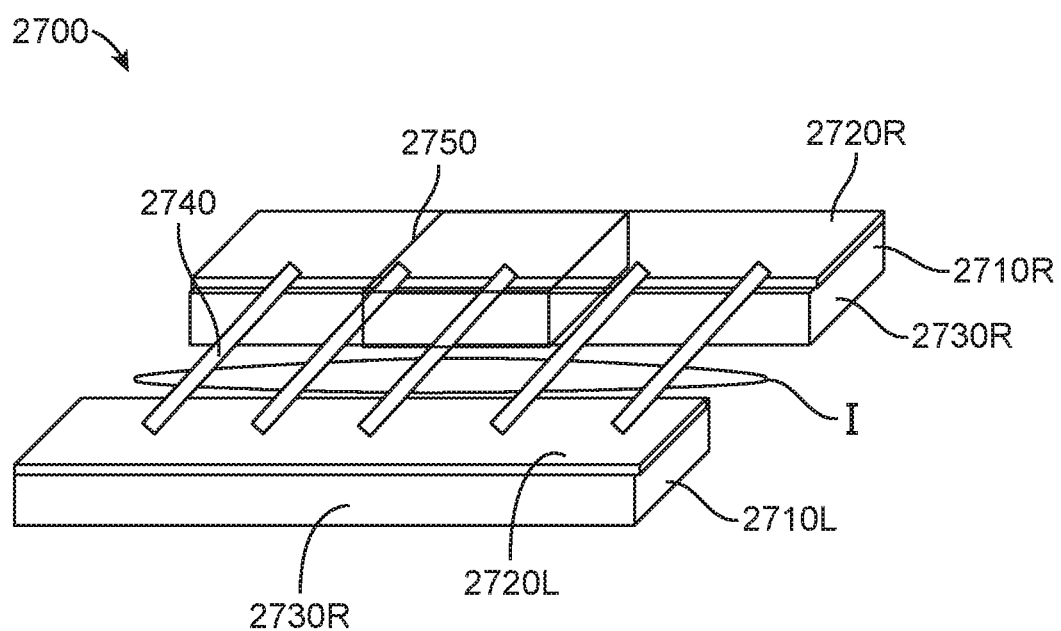
FIGS. 27A-27E illustrate embodiments of a wound closure appliance having a medicinal agent incorporated thereon in accordance with the principles of the present invention.

Referring now to FIG. 27A, a wound or incision closure appliance 2700 comprises a base comprising two base panels 2710R, 2710L comprising upper polymer layers 2720R, 2720L and lower adhesive layers 2730R, 2730L applied in close proximity to each side of a surgical incision I. Features of the panels 2710R, 2710L, such as straps 2740, may allow the skin on either side of the incision I to be drawn together and held in place during the healing period. The adhesive may preferably comprise a hydrocolloid formulation, but may comprise acrylic or other adhesives known in the art. The upper polymer layers 2710R, 2710L (e.g., 1 mil polyurethane) are preferably applied to the top of the adhesive layers 2720R, 2720L to isolate the adhesive layers 2720R, 2720L. Medicinal agents may be incorporated into the structure of the base panels 2710R, 2710L. At a minimum, the agents may inhibit growth of unwanted organisms where they contact the skin from the base panes 2710R, 2710L. The agents may be released from the base panels 2710R, 2710L and may migrate to regions within or in close proximity to the wound. The agents may be contained with carrier structures, such as adhesive layers 2730R, 2730L, which are able to absorb fluid and aid in the release of the agents. Such structures may include hydrocolloids, hydrofibers (such as those containing sodium carbomethylcellulose), hydrogels, collagen, alginates, foams of polyurethane or silicone, or other related materials known in the art. The carrier could alternatively or in combination be an ointment, cream, gel, or powder. The medicinal agent (such as silver ions) may alternatively or in combination be applied to metals or polymers (for example, in mesh form) via a solvent coating process or vapor deposition. Such mesh-like products may be bonded or imbedded in the structure of a closure device.

In exemplary embodiments, a medicinal agent comprising a silver compound such as silver sulfate may be incorporated into the base panels 2710R, 2710L. As the base panels 2710R, 2710L come into contact with wound exudate and/or sweat or external fluids, the agents may be carried toward the wound. As fluid is absorbed into the base panels 2710R, 2710L, the base panels 2710R, 2710L may be able to release the silver ions which interfere with bacterial growth. Examples of how an agent such as silver may be incorporated into the base panels are shown in FIGS. 28A-28B, which show various embodiments of sample segment 2750 of the right base panel 2710R in FIG. 27. These examples may also apply for the left base panel 2710L.

Figure 27B:
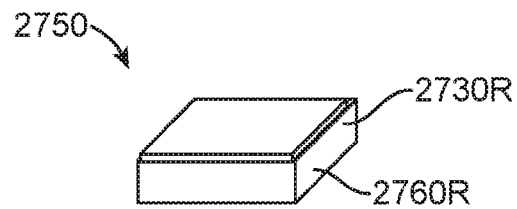
Figure 28A:
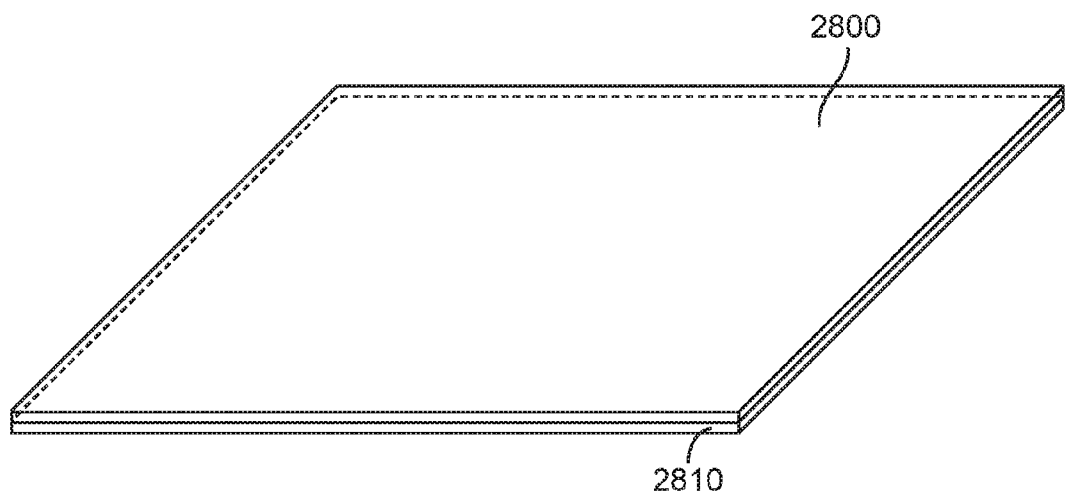
FIGS. 28A-28E illustrate embodiments of a wound closure appliance cover having a medicinal agent incorporated thereon in accordance with the principles of the present invention.
Figure 28B:
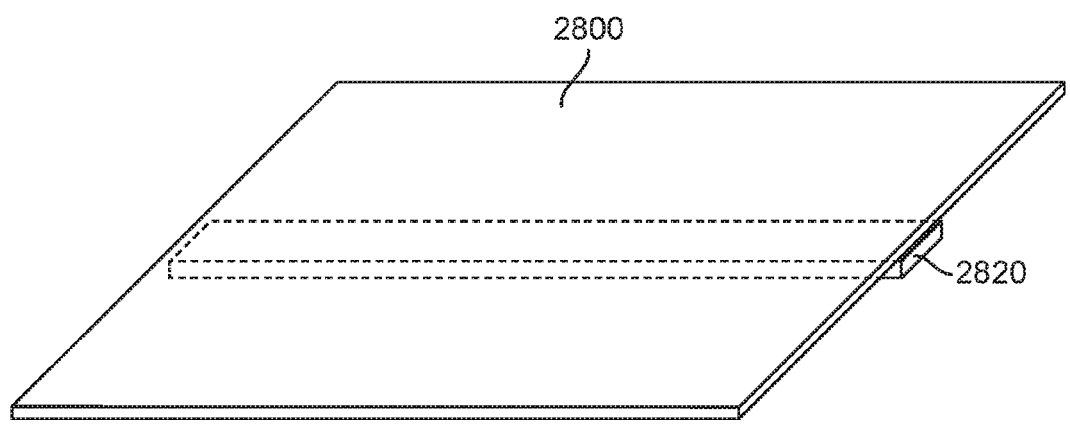

FIG. 27B shows a medicinal agent 2760R blended directly into the adhesive layer 2730R in the sample segment 2750. The adhesive is typically a hydrocolloid, which may be able to absorb a significant percent of its weight in fluid, thereby aiding the release of the agents.

Figure 27C:
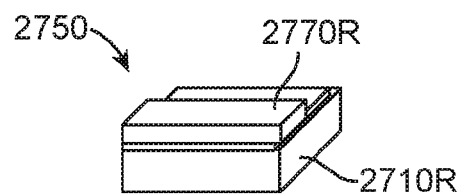

FIG. 27C shows another embodiment of the sample segment 2750 of the base panel 2710R in which the medicinal agent is incorporated into a carrier structure 2770R which is incorporated on top of the base panel 2710R, preferably concentrated on the part of the base panel 2710R near the incision I. Further features may be incorporated to strip away (and replace as needed) the carrier structure 2770R if it becomes saturated with exudate or other fluids, and/or the concentration of the medicinal agent drops below and effective level.

Figure 27D:
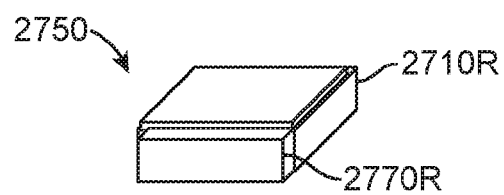

FIG. 27D shows an embodiment similar to that of FIG. 27C in which the carrier structure 2770R comprising the medicinal agent is incorporated on the inside edge of the base panel 2710R.

Figure 27E:
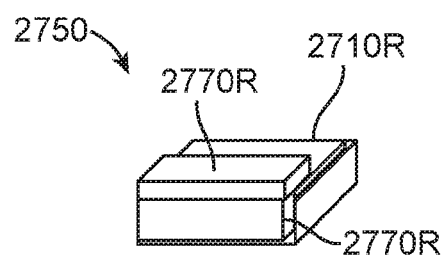

FIG. 27E illustrates how the carrier 2770R could be incorporated onto both the top and inside edge of the base panel 2710R. In these examples, the carrier structure 2770R on either or each inside edge of the base panel 2710R may be compressed over the wound or incision I to aid in its stability over the wound or incision I.

Medicinal agents and their carrier structures may alternatively or in combination be incorporated into the cover for the incision closure appliance. As described above, the cover is typically applied over the base panels of the incision closure appliances to help secure the appliance to the skin and protect the skin. As shown in FIG. 28A, a cover 2800 could have the medicinal agent 2810 incorporated into the entire surface of the cover 2800 with or without a carrier structure, such as adhesive layer 2810 mixed with the medicinal agent. Alternatively or in combination, the agent may be incorporated into a discreet portion of the cover 2800, preferably within a carrier structure 2820 lying directly over the wound site as shown in FIG. 28B.

Figure 28C:
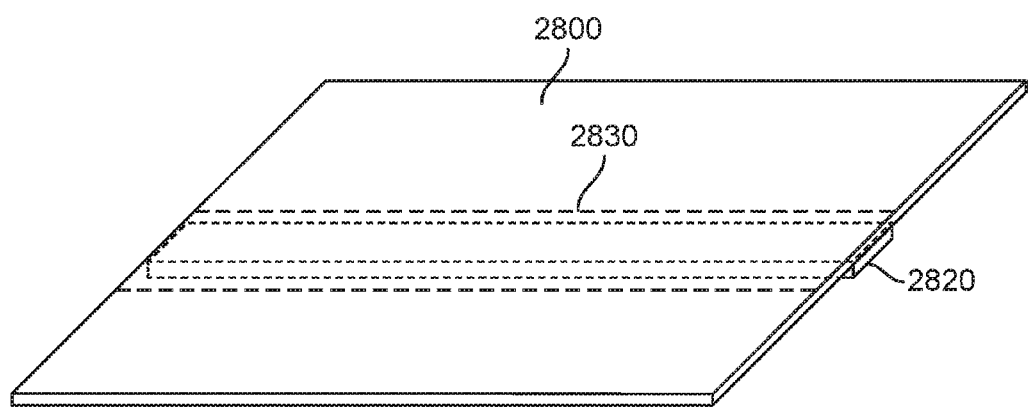
Figure 28D:
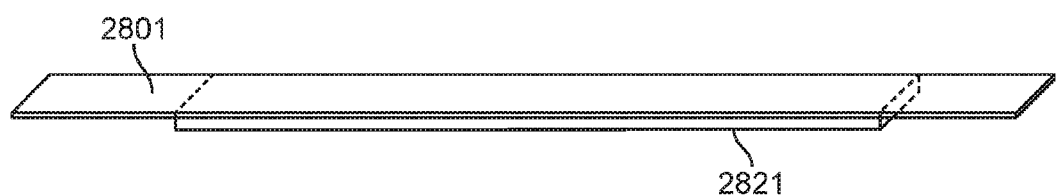
Figure 28E:
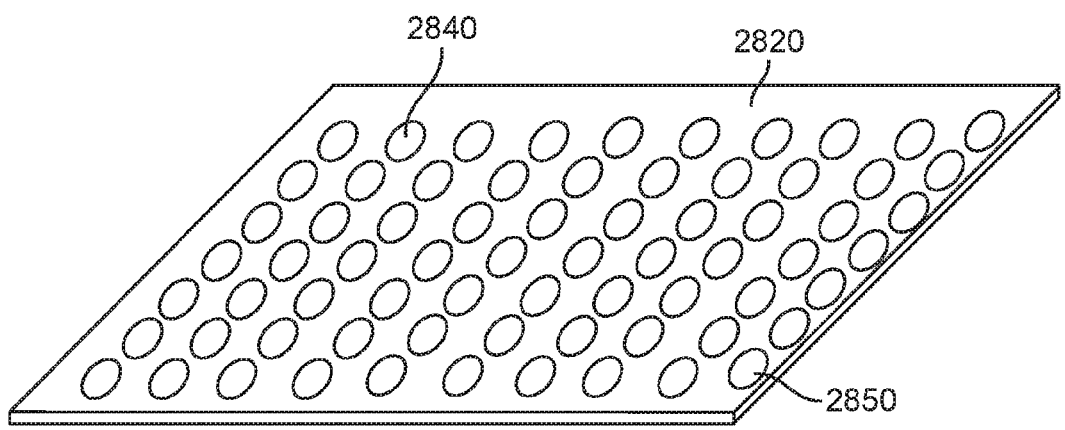

In at least some instances, the carrier structure 2820 may become saturated over time and/or lose its medicinal strength, and replacing the medicinal structure 2820 will be of benefit. As shown in FIG. 28C, the medicinal structure 2820 could be removable (e.g., through tear-away perforations 2830 in the cover 2800) and optionally replaced with another medicinal structure 2821 coupled to the narrow cover strip 2801 shown in FIG. 28D. In the narrow cover strip 2801, the adhesive portion of the cover 2801 may extend beyond the medicinal structure 2821 to hold the structure 2821 against the skin. The narrow strip 2801 may alternatively be applied to the wound site before the cover 2800 is applied. The cover 2800 may be designed to cover the narrow strip 2801, or the may have perforations 2830 to allow removal of the underlying strip.

For either or both the base panels 2710R, 2710L and the cover 2800, the carrier structures 2770R or 2820 (with or without the medicinal agent), or the medicinal agent alone, could be patterned with the adhesive layer of the respective structure. A patterned construction may comprise a repeating shape (e.g., circles, ovals, polygon, slots, etc.) of adhesive material adjacent a similar repeating shape (or remainder of the matrix) of the carrier structure. This would help ensure adhesion of the base panels 2710R, 2710L or cover 2800 while integrating the medicinal agent within the carrier structure 2770R or 2820. A simple example is shown in FIG. 29E in which the carrier structure 2820 comprises a repeating shape 2850. The medicinal agent and carrier structure 2820 could also be applied to the base straps 2740 which cross the incision I.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An incision closure apparatus comprising:
a first base panel for being adhered to a first side of an incision or wound, the first base panel comprising a longitudinal axis, an upper surface, and a tissue adherent lower surface;
a second base panel for being adhered to a second side of the incision or wound opposite the first side, the second base panel comprising a longitudinal axis, an upper surface, and a tissue adherent lower surface, the second base panel being discrete from the first base panel; and
a plurality of lateral ties coupling the first and second base panels to one another,
wherein the first and second base panels are each unitary, and
wherein the first and second base panels are each longitudinally stretchable and each comprise a plurality of preferentially separating regions distributed along the longitudinal axes thereof, the plurality of preferentially separating regions facilitating separation of one or more of the first or second base panels into discrete segments along the longitudinal axes thereof while an entirety of the incision closure apparatus is connected as a single unit.

2. The incision closure apparatus of claim 1, wherein the preferentially separating regions comprise one or more perforations through the first or second base panels.

3. The incision closure apparatus of claim 2, wherein the one or more perforations comprise a plurality of perforations disposed along a lateral line across the first or second base panel.

4. The incision closure apparatus of claim 1, wherein the plurality of preferentially separating regions allow the unitary first and second base panels to tear or separate into a plurality of longitudinally adjacent base panel segments disposed along the longitudinal axes thereof when longitudinally stretched beyond a threshold.

5. The incision closure apparatus of claim 1, wherein at least some of the plurality of preferentially separating regions are positioned along a lateral edge of the first or second base panel to reduce stress as underlying skin stretches radially outward from the incision or wound.

6. The incision closure apparatus of claim 1, further comprising a first plurality of longitudinally spaced-apart supports coupled to the upper surface of the first base panel and a second plurality of longitudinally spaced-apart supports coupled to the upper surface of the second base panel, the first and second pluralities of longitudinally spaced-apart supports being distributed along the longitudinal axes of the first and second base panels, respectively.

7. The incision closure apparatus of claim 6, wherein one or more of the first or second plurality of longitudinally spaced-apart supports comprise force distribution structures.

8. The incision closure apparatus of claim 6, wherein at least some of the preferentially separating regions are longitudinally disposed between longitudinally adjacent supports on the first or second base panel.

9. The incision closure apparatus of claim 6, wherein one or more supports of the first or second plurality of longitudinally spaced apart supports is disposed longitudinally adjacent an inner edge of the first or second base panel, respectively.

10. The incision closure apparatus of claim 6, wherein the supports comprise flexible, non-distensible materials.

11. The incision closure apparatus of claim 6, wherein the supports are embedded in or laminated to the upper surface of each panel.

12. The incision closure apparatus of claim 6, wherein one or more of the supports are C-shaped.

13. The incision closure apparatus of claim 1, wherein the plurality of lateral ties reversibly and adjustably couple the first and second base panels to one another such that a spacing between the first and second base panels is adjustable.

14. The incision closure apparatus of claim 13, wherein the lateral ties each have one end fixed to one of the first or second base panels and an opposite end adjustably attached to one of the opposite base panel, thereby allowing the lateral ties to draw the first and second base panels together to compress a wound or incision covered by the incision closure apparatus.

15. The incision closure appliance of claim 14, wherein the opposite end of each lateral tie is releasably attached to a lock, and wherein the lateral tie and lock together form a ratchet tightening mechanism.

16. The incision closure apparatus of claim 1, wherein one or more of the first or second base panels comprise an elastic matrix.

17. The incision closure apparatus of claim 16, wherein the elastic matrix comprises an elastomeric membrane, a woven fabric, a spun fabric, rubber, latex, urethane, polyurethane, silicone, or a thermo plastic elastomer (TPE).

18. The incision closure apparatus of claim 17 wherein the elastic matrix comprises a fabric woven from elastic elements and having inelastic elements along lateral edges of the one or more of the first or second base panels and extending laterally thereacross.

19. The incision closure apparatus of claim 1, wherein the tissue adherent lower surface of one or more of the first or second base panels comprises a hydrophilic adhesive material.

20. The incision closure apparatus of claim 19, wherein the hydrophilic adhesive material comprises one or more of a hydrocolloid, a hydrogel, an acrylic polymer, or poly (ethylene glycol).

21. The incision closure apparatus of claim 1, further comprising a securing layer adapted to be placed over an assembly of the first and second base panels and the lateral ties after the assembly has been secured over the incision or wound.

22. The incision closure apparatus of claim 21, wherein the securing layer has an inner self-adhesive surface.

23. The incision closure apparatus of claim 21, wherein the securing layer is configured to laterally extend beyond an outer lateral edge of the first or second base panel.

24. The incision closure apparatus of claim 21, wherein the securing layer has one or more preferentially separating regions to allow the securing layer to at least partially stretch longitudinally in response to longitudinal stretching of the incision or wound and surrounding tissue the incision closure appliance is placed over.

* * * * *